US009790478B2

(12) United States Patent
Muerhoff et al.

(10) Patent No.: US 9,790,478 B2
(45) Date of Patent: Oct. 17, 2017

(54) HCV NS3 RECOMBINANT ANTIGENS AND MUTANTS THEREOF FOR IMPROVED ANTIBODY DETECTION

(71) Applicant: Abbott Laboratories, Abbott Park, IL (US)

(72) Inventors: A. Scott Muerhoff, Kenosha, WI (US); Christopher Marohnic, Kenosha, WI (US); Larry Birkenmeyer, Glenview, IL (US); John Prostko, Kenosha, WI (US); M. Felisha Bogdan, Gurnee, IL (US); Robin Gutierrez, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/139,053

(22) Filed: Dec. 23, 2013

(65) Prior Publication Data

US 2014/0272932 A1   Sep. 18, 2014

Related U.S. Application Data

(60) Provisional application No. 61/784,822, filed on Mar. 14, 2013, provisional application No. 61/899,514, filed on Nov. 4, 2013.

(51) Int. Cl.
| | |
|---|---|
| *G01N 33/569* | (2006.01) |
| *C12N 9/14* | (2006.01) |
| *G01N 33/576* | (2006.01) |
| *C07K 14/005* | (2006.01) |

(52) U.S. Cl.
CPC ............. *C12N 9/14* (2013.01); *C07K 14/005* (2013.01); *G01N 33/5767* (2013.01); *C07K 2319/20* (2013.01); *C07K 2319/21* (2013.01); *C12N 2770/24222* (2013.01); *C12N 2800/22* (2013.01); *G01N 2469/20* (2013.01)

(58) Field of Classification Search
None
See application file for complete search history.

(56) References Cited

U.S. PATENT DOCUMENTS

| | | |
|---|---|---|
| 4,338,397 A | 7/1982 | Gilbert et al. |
| 4,425,437 A | 1/1984 | Riggs |
| 4,431,739 A | 2/1984 | Riggs |
| 4,526,938 A | 7/1985 | Churchill |
| 4,554,101 A | 11/1985 | Hopp |
| 4,816,397 A | 3/1989 | Boss |
| 4,816,567 A | 3/1989 | Cabilly |
| 4,880,078 A | 11/1989 | Inoue et al. |
| 4,946,778 A | 8/1990 | Ladner |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner |
| 5,225,539 A | 7/1993 | Winter |
| 5,241,070 A | 8/1993 | Law |
| 5,242,828 A | 9/1993 | Bergstrom |
| 5,258,498 A | 11/1993 | Huston |
| 5,290,540 A | 3/1994 | Prince et al. |
| 5,294,404 A | 3/1994 | Grandone et al. |
| 5,350,671 A | 9/1994 | Houghton et al. |
| 5,352,803 A | 10/1994 | Mattingly |
| 5,359,093 A | 10/1994 | Adamczyk et al. |
| 5,399,346 A | 3/1995 | Anderson et al. |
| 5,403,484 A | 4/1995 | Ladner |
| 5,427,908 A | 6/1995 | Dower |
| 5,468,646 A | 11/1995 | Mattingly et al. |
| 5,496,925 A | 3/1996 | Mattingly |
| 5,516,637 A | 5/1996 | Huang |
| 5,530,101 A | 6/1996 | Queen |
| 5,543,524 A | 8/1996 | Mattingly et al. |
| 5,565,332 A | 10/1996 | Hoogenboom |
| 5,565,352 A | 10/1996 | Hochstrasser |
| 5,571,698 A | 11/1996 | Ladner |
| 5,573,904 A | 11/1996 | Mattingly |
| 5,580,717 A | 12/1996 | Dower |
| 5,585,089 A | 12/1996 | Queen |
| 5,593,896 A | 1/1997 | Adamczyk et al. |
| 5,624,821 A | 4/1997 | Winter |

(Continued)

FOREIGN PATENT DOCUMENTS

| | | |
|---|---|---|
| CA | 2450710 | 1/2003 |
| EP | 086631 | 8/1983 |

(Continued)

OTHER PUBLICATIONS

PCT, Notification of Transmittal of the International Search Report and the Written Opinion of the International Searching Authority, or the Declaration, in International application No. PCT/US13/77487, dated Apr. 22, 2014 (23 pages).
Kim, D. et al., Mulational Analysis of the Hepatitis C Virus RNA Helicase, Journal of Virology, Dec. 1997, vol. 71, No. 12; pp. 9400-9409; p. 9402, left column, third paragraph; Table 2 ( pages).
Kim, M., Template Requirements for De Novo RNA Synthesis by Hepatitis C Virus Nonstructural Protein 5B Polymerase on the Viral X RNA, Journal of Virology, Jul. 2002, vol. 76, No. 14, pp. 6944-6945, left column, second paragraph. DOI: 10.1128/JVI.76.14.6944-6956. 2002. (14 pages).
Tai, C. Structure-Based Mulational Analysis of the Hepatitis C Virus NS3 Helicase, Journal of Virology, Sep. 2001. vol. 75, No. 17; pp. 8289-8297; p. 8292, Table 2. DOI: 10.1128/JVI.75.17.8289-8297. 2001. (10 pages).
Beckett et al., "A minimal peptide substrate in biotin holoenzyme synthetase-catalyzed biotinylation," Protein Sci., 8 (1999) (4):921-929.

(Continued)

*Primary Examiner* — Agnieszka Boesen
(74) *Attorney, Agent, or Firm* — Lisa V. Mueller; Michael Best & Friedrich LLP

(57) ABSTRACT

The present disclosure relates to polypeptides, including fusions thereof, nucleic acids, vectors, host cells, immunodiagnostic reagents, kits, and immunoassays for use detecting the presence of HCV antibodies. More specifically, the present invention describes specific NS3 antigens that can be used for the detection of anti-HCV antibodies.

29 Claims, 1 Drawing Sheet

(56) References Cited

U.S. PATENT DOCUMENTS

| | | | |
|---|---|---|---|
| 5,627,052 A | 5/1997 | Schrader |
| 5,641,870 A | 6/1997 | Rinderknecht |
| 5,648,260 A | 7/1997 | Winter |
| 5,658,727 A | 8/1997 | Barbas |
| 5,679,377 A | 10/1997 | Bernstein et al. |
| 5,688,688 A | 11/1997 | Luciw et al. |
| 5,693,762 A | 12/1997 | Queen |
| 5,698,426 A | 12/1997 | Huse |
| 5,705,330 A | 1/1998 | Shah et al. |
| 5,714,350 A | 2/1998 | Co et al. |
| 5,714,352 A | 2/1998 | Jakobovits |
| 5,723,323 A | 3/1998 | Kauffman |
| 5,733,743 A | 3/1998 | Johnson |
| 5,750,753 A | 5/1998 | Kimae |
| 5,753,430 A | 5/1998 | Mehta et al. |
| 5,763,192 A | 6/1998 | Kauffman |
| 5,766,886 A | 6/1998 | Studnicka |
| 5,780,225 A | 7/1998 | Wigler |
| 5,783,699 A | 7/1998 | Mattingly et al. |
| 5,795,784 A | 8/1998 | Arnquist et al. |
| 5,807,715 A | 9/1998 | Morrison et al. |
| 5,814,476 A | 9/1998 | Kauffman |
| 5,817,483 A | 10/1998 | Kauffman |
| 5,821,047 A | 10/1998 | Garrard |
| 5,824,514 A | 10/1998 | Kauffman |
| 5,855,913 A | 1/1999 | Hanes et al. |
| 5,856,194 A | 1/1999 | Arnquist et al. |
| 5,874,064 A | 2/1999 | Edwards et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hori |
| 5,934,272 A | 8/1999 | Lloyd et al. |
| 5,939,598 A | 8/1999 | Kucherlapati |
| 5,969,108 A | 10/1999 | McCafferty |
| 5,976,862 A | 11/1999 | Kauffman |
| 5,985,309 A | 11/1999 | Edwards et al. |
| 5,985,320 A | 11/1999 | Edwards et al. |
| 5,985,615 A | 11/1999 | Jakobovits |
| 5,989,463 A | 11/1999 | Tracy et al. |
| 5,989,905 A * | 11/1999 | Houghton et al. ......... 435/320.1 |
| 5,998,209 A | 12/1999 | Jokobovits |
| 6,019,968 A | 2/2000 | Platz et al. |
| 6,075,181 A | 6/2000 | Kucherlapati |
| 6,091,001 A | 7/2000 | Jakobovits |
| 6,096,319 A | 8/2000 | Seidel |
| 6,114,598 A | 9/2000 | Kucherlapati |
| 6,130,364 A | 10/2000 | Jakobovits |
| 6,172,189 B1 | 1/2001 | Devare |
| 6,180,370 B1 | 1/2001 | Queen |
| 6,194,222 B1 | 2/2001 | Buechler et al. |
| 6,204,023 B1 | 3/2001 | Robinson |
| 6,225,047 B1 | 5/2001 | Hutchens et al. |
| 6,306,579 B1 * | 10/2001 | Seidel et al. ..................... 435/5 |
| 6,329,209 B1 | 12/2001 | Wagner et al. |
| 6,350,861 B1 | 2/2002 | Co et al. |
| 6,555,114 B1 | 4/2003 | Leroux-Roels et al. |
| 6,623,921 B2 | 9/2003 | Aoyagi |
| 6,699,658 B1 | 3/2004 | Wittrup |
| 6,727,092 B2 | 4/2004 | Shah |
| 6,846,905 B2 | 1/2005 | Hackett et al. |
| 6,914,128 B1 | 7/2005 | Salfeld |
| 7,101,683 B2 | 9/2006 | Shah et al. |
| 7,285,418 B2 | 10/2007 | Katrukha et al. |
| 7,371,383 B2 | 5/2008 | Reed et al. |
| 7,462,354 B2 * | 12/2008 | Sette et al. ................. 424/184.1 |
| 7,521,542 B2 | 4/2009 | Johnson et al. |
| 7,612,181 B2 | 11/2009 | Wu |
| 7,858,752 B2 | 12/2010 | Tu |
| 7,871,625 B2 | 1/2011 | Chien et al. |
| 7,888,004 B2 * | 2/2011 | Coit et al. ........................ 435/5 |
| 8,030,026 B2 | 10/2011 | Brophy |
| 8,193,318 B2 | 6/2012 | Koenig et al. |
| 8,865,398 B2 | 10/2014 | Rodgers et al. |
| 9,194,873 B2 | 11/2015 | Dawson et al. |
| 2002/0037868 A1 | 3/2002 | Budkowska |
| 2002/0137134 A1 | 9/2002 | Gerngross |
| 2003/0152948 A1 | 8/2003 | Shah et al. |
| 2003/0170881 A1 | 9/2003 | Davis et al. |
| 2003/0186374 A1 | 10/2003 | Hufton |
| 2004/0018577 A1 | 1/2004 | Campbell et al. |
| 2004/0018590 A1 | 1/2004 | Gemgross et al. |
| 2004/0072267 A1 | 4/2004 | Rieunier et al. |
| 2005/0054078 A1 | 3/2005 | Miller et al. |
| 2006/0018897 A1 | 1/2006 | Lee et al. |
| 2006/0160164 A1 | 7/2006 | Miller et al. |
| 2008/0020401 A1 | 1/2008 | Grenier et al. |
| 2008/0113339 A1 | 5/2008 | Rodgers et al. |
| 2008/0248493 A1 | 10/2008 | Mattingly et al. |
| 2010/0297607 A1 | 11/2010 | Zheng |
| 2012/0009196 A1 | 1/2012 | Muerhoff |
| 2012/0046188 A1 | 2/2012 | Berland et al. |
| 2014/0272931 A1 | 9/2014 | Ziemann |
| 2014/0272933 A1 | 9/2014 | Dawson et al. |
| 2015/0024457 A1 | 1/2015 | Brophy |

FOREIGN PATENT DOCUMENTS

| | | |
|---|---|---|
| EP | 0229246 | 7/1987 |
| EP | 0239400 | 9/1987 |
| EP | 0424634 | 5/1991 |
| EP | 0471293 | 2/1992 |
| EP | 0519596 | 12/1992 |
| EP | 0592106 | 4/1994 |
| EP | 0967485 | 12/1999 |
| EP | 1176195 | 1/2002 |
| EP | 1308507 | 5/2003 |
| EP | 1310796 | 5/2003 |
| EP | 2099825 | 6/2008 |
| EP | 2014302 | 1/2009 |
| FR | 2779526 | 12/1999 |
| WO | WO 90/01443 | 2/1990 |
| WO | WO 90/05144 | 5/1990 |
| WO | WO 90/05370 | 5/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09630 | 5/1991 |
| WO | WO 91/09967 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/03461 | 3/1992 |
| WO | WO 92/09690 | 6/1992 |
| WO | WO 92/11272 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | 93/00365 | 1/1993 |
| WO | WO 93/01288 | 1/1993 |
| WO | WO 93/06213 | 4/1993 |
| WO | WO 93/11236 | 6/1993 |
| WO | 94/01778 | 1/1994 |
| WO | WO 94/02602 | 2/1994 |
| WO | WO 94/18219 | 8/1994 |
| WO | WO 95/15982 | 6/1995 |
| WO | WO 95/20401 | 8/1995 |
| WO | WO 96/20698 | 7/1996 |
| WO | WO 96/33735 | 10/1996 |
| WO | WO 96/34096 | 10/1996 |
| WO | WO 97/20032 | 6/1997 |
| WO | WO 97/29131 | 8/1997 |
| WO | WO 97/32572 | 9/1997 |
| WO | WO 97/44013 | 11/1997 |
| WO | WO 98/16654 | 4/1998 |
| WO | WO 98/24893 | 6/1998 |
| WO | WO 98/31346 | 7/1998 |
| WO | WO 98/31700 | 7/1998 |
| WO | 98/37200 | 8/1998 |
| WO | WO 98/50433 | 11/1998 |

(56) References Cited

FOREIGN PATENT DOCUMENTS

| WO | 99/09148 | 2/1999 |
|---|---|---|
| WO | WO 99/06834 | 2/1999 |
| WO | WO 99/15154 | 4/1999 |
| WO | WO 99/20253 | 4/1999 |
| WO | WO 99/45031 | 9/1999 |
| WO | 99/51773 | 10/1999 |
| WO | WO 99/51773 | 10/1999 |
| WO | WO 99/53049 | 10/1999 |
| WO | WO 99/54342 | 10/1999 |
| WO | WO 99/66903 | 12/1999 |
| WO | WO 00/07023 | 2/2000 |
| WO | WO 00/09560 | 2/2000 |
| WO | WO 00/37504 | 6/2000 |
| WO | 00/56934 | 9/2000 |
| WO | WO 00/56772 | 9/2000 |
| WO | WO 00/56943 | 9/2000 |
| WO | 01/09609 | 2/2001 |
| WO | 01/21189 | 3/2001 |
| WO | 01/38360 | 5/2001 |
| WO | 01/38360 A2 | 5/2001 |
| WO | WO 01/83525 | 11/2001 |
| WO | 01/96875 | 12/2001 |
| WO | WO 02/072636 | 9/2002 |
| WO | 03/002749 | 1/2003 |
| WO | WO 03/016466 | 2/2003 |
| WO | WO 03/035835 | 5/2003 |
| WO | WO 03/086458 | 10/2003 |
| WO | 2004/070387 | 8/2004 |
| WO | WO 2005/000901 | 1/2005 |
| WO | WO 2005/010049 | 2/2005 |
| WO | WO 2005/035575 | 4/2005 |
| WO | WO 2005/068503 | 7/2005 |
| WO | WO 2005/100584 | 10/2005 |
| WO | WO 2008/028686 | 3/2008 |
| WO | 2008/051762 | 5/2008 |
| WO | WO 2008/120202 | 10/2008 |
| WO | WO 2010/060186 | 6/2010 |
| WO | 2011/163558 | 12/2011 |

OTHER PUBLICATIONS

Dijkema et al., "Cloning and expression of the chromosomal immune interferon gene of the rat," EMBO J., 4 (1985) (3):761-767.
Gorman et al., "The Rous sarcoma virus long terminal repeat is a strong promoter when introduced into a variety of eukaryotic cells by DNA-mediated transfection," Proc. Natl. Acad. Sci. USA, 79(22):6777-6781 (1982).
Gu et al., "Three conformational snapshots of the hepatitis C virus NS3 helicase reveal a ratchet translocation mechanism," Proc. Natl. Acad. Sci. USA, 107(2):521-528 (2010).
Huston et al., "Protein engineering of antibody binding sites: recovery of specific activity in an anti-digoxin single-chain Fv analogue produced in *Escherichia coli*," Proc. Natl. Acad. Sci. USA, 85(16):5879-5883 (1988).
Jay et al., "Chemical synthesis of a biologically active gene for human immune interferon-gamma. Prospect for site-specific mutagenesis and structure-function studies," J. Biol. Chem., 259(10):6311-6317 (1984).
Jayaraman et al., "Polymerase chain reaction-mediated gene synthesis: synthesis of a gene coding for isozyme c of horseradish peroxidase," Proc. Natl. Acad. Sci. USA, 88(10):4084-4088 (1991).
Ogata et al., "Nucleotide sequence and mutation rate of the H strain of hepatitis C virus," Proc. Natl. Acad. Sci. USA, 88(8):3392-3396 (1991).
Queen et al., "A humanized antibody that binds to the interleukin 2 receptor," Proc. Natl. Acad. Sci. USA, 86 (24):10029-10033 (1989).
Sallberg et al., "Immunogenicity and antigenicity of the ATPase/helicase domain of the hepatitis C virus non-structural 3 protein," J. Gen. Virol., 77(Pt 11):2721-2728 (1996).
Wallemacq et al., "Evaluation of the New AxSYM Cyclosporine Assay: Comparison with TDx Monoclonal Whole Blood and Emit Cyclosporine Assays," Clin. Chem., 45(3):432-435 (1999).
Yatscoff et al., "Abbott TDx Monoclonal Antibody Assay Evaluated for Measuring Cyclosporine in Whole Blood," Clin. Chem., 36(11):1969-1973 (1990).
International Search Report for Application No. PCT/US13/77487 dated Apr. 22, 2014.
Kim et al., "Mutational analysis of the hepatitis C virus RNA helicase," Journal of Virology, 71(12):9400-9409 (1997).
Kim et al., "Template Requirements for De Novo RNA Synthesis by Hepatitis C Virus Nonstructural Protein 5B Polymerase on the Viral X RNA," Journal of Virology, 76(14):6944-6956 (2002).
Tai et al., "Structure-Based Mutational Analysis of the Hepatitis C Virus NS3 Helicase," Journal of Virology, 74 (17):8289-8207 (2001).
Co-pending U.S. Appl. No. 15/079,013, filed Mar. 23, 2016, Robert Ziemann.
United States Patent Office Notice of Allowance for U.S. Appl. No. 14/138,991 dated Feb. 23, 2016 (7 pages).
United States Patent Office Action for U.S. Appl. No. 14/461,082 dated Apr. 15, 2016 (7 pages).
U.S. Appl. No. 14/851,471, filed Sep. 11, 2015, Dawson et al.
Aach, R.D. et al., "Hepatitis C virus infection in post-transfusion hepatitis. An analysis with first- and second-generation assays," N. Engl. J. Med. (1991) 325(19):1325-1329.
Adamczyk et al., "Chemiluminescence quenching of pteroic acid-N-sulfonyl-acridinium-9-carboxamide conjugates by folate finding protein," Bioorg. Med. Chem. Lett. (2004) 14(9):2313-2317.
Adamczyk et al., "Chemiluminescent acridinium-9-carboxamide boronic acid probes: application to a homogenous glycated hemoglobin assay," Bioorg. Med. Chem. Lett (2006) 16(5):1324-1328.
Adamczyk et al., "Homogenous chemiluminescent assays for free choline in human plasma and whole blood," Anal. Chim. Acta (2006) 579(1):61-67.
Adamczyk et al., "Intrinsic factor-mediated modulation of cyanocobalain-N-sulfonyl-acridinium-9-carboxamide chemiluminescence," Biorg. Med. Chem. Lett. (2004) 14(15):3917-3921.
Adamczyk et al., "Linker-mediated modulation of the chemiluminescent signal from N(10)-(3-sulfopropyl)-N-sulfonylacridinium-9-carboxamide tracers," Bioconjug. Chem. (2000) 11(5):714-724.
Adamczyk et al., "Modulation of the chemiluminescent signal from N10-(3-sulfopropyl)-N-sulfonylacridinium-9-carboximides," Tetrahedron (1999) 55:10899-10914.
Adamczyk et al., "Neopentyl 3-triflyloxypropanesulfonate. A reactive sulfopropylation reagent for the preparation of chemiluminescent labels," J. Org. Chem. (1998) 63:5636-5639.
Adamczyk et al., "Regiodependent luminescence quenching of biotinylated N-sulfonyl-acridinium-9-carboxamides by avidin," Org. Lett (2003) 5(21):3779-3782.
Adamczyk et al., "Synthesis of a chemiluminescent acridinium hydroxylamine (AHA) for the direct detection of abasic sites in DNA," Org. Lett (1999) 1(5):779-781.
Alter et al., "The natural history of community-acquired heptatitis C in the United States. The Sentinel Counties Chronic non-A, non-B hepatitis study team," N. Eng. J. Med. (1992) 327(27):1899-1905.
Altschul, S.F. et al., "Gapped BLAST and PSI-BLAST: a new generation of protein database search programs," Nucleic Acids Res. (1997) 25:3389-3402.
Ames et al., "Conversion of murine Fabs isolated from a combinatorial phage display library to full length immunoglobulins," J. Immunol. Methods (1995) 184(2):177-186.
Anthony et al., "Racapitulation of IVIG anti-inflammatory activity with a recombinant IgG Fc," Science (2008) 320(5874):373-376.
Azzazy et al., "Phage display technology: clinical applications and recent innovations," Clin. Biochem. (2002) 35(6):425-445.
Babcook et al., "A novel strategy for generating monoclonal antibodies from single, isolated lymphocytes producing antibodies of defined specificities," Proc. Natl. Acad. Sci. USA (1996) 93(15):7843-7848.
Barbas et al., "Assembly of combinatorial antibody libraries on phage surfaces: the gene III site," Proc. Natl. Acad. Sci. USA (1991) 88(18):7978-7982.

(56) References Cited

OTHER PUBLICATIONS

Barbas et al., In vitro evolution of a neutralizing human antibody to human immunodeficiency virus type 1 to enhance affinity and broaden strain cross-reactivity, Proc. Natl. Acad. Sci. USA (1994) 91(9):3809-3813.
Better et al., "*Escherichia coli* secretion of an active chimeric antibody fragment," Science (1988) 240(4855): 1041-1043.
Beidler et al., "Cloning and high level expression of a chimeric antibody with specificity for human carcinoembryonic antigen," J. Immunol. (1988) 141(11):4053-4060.
Biewenga et al., "IgA1 half olecules in human multiple myeloma and the in vitro production of similar fragments from intact IgA1 molecules," Clin. Exp. Immunol. (1983) 51(2):395-400.
Bird et al., "Single-chain antigen-binding proteins," Science (1988) 242(4877):423-426.
Bodor, G.S. et al., "Development of monoclonal antibodies for an assay of cardiac Troponin-I and preliminary results in suspected cases of myocardial infarction," Clinical Chem. (1992) 38:2203-2214.
Boder, E.T. et al., "Yeast surface display for screening combinatorial polypeptide libraries," Nature Biotech. (1997) 15:553-557.
Boulant et al., "Hepatitis C virus core protein is a dimeric alpha-helical protein exhibiting membrane protein features," J. Virol. (2005) 79(17):11353-11365.
Bresters et al., "Enhanced sensitivity of a second generation ELISA for antibody to hepatitis C virus," Vox Sang (1992) 62(4):213-217.
Brinkmann et al., "Phage display of disulfide-stabilized Fv fragments," J. Immunol. Methods (1995) 182(1):41-50.
Buchwald, H. et al., "Long-term, continuous intravenous heparin administration by an implantable infusion pump in ambulatory patients with recurrent venous thrombosis," Surgery (1980) 88:507-516.
Burton et al., "Human antibodies from combinatorial libraries," Adv. Immunol. (1994) 57:191-280.
Busch et al., "Committee report. Nucleic acid amplification testing of blood donors for transfusion-transmitted infectious diseases: Report of the Interorganizational Task Force on Nucleic Acid Amplification Testing of Blood Donors," Transfusion (2000) 40(2):143-159.
Carter et al., "Humanization of an anti-p185HER2 antibody for human cancer therapy," Proc. Natl. Acad. Sci. USA (1992) 89(10):4285-4289.
Choo et al., "Isolation of a cDNA clone derived from a blood-forne non-A, non-B viral hepatitus genome," Science (1989) 244(4902):359-362.
Chothia, C. et al., "Canonical structures for the hypervariable regions of immunoglobulins," J. Mol. Biol. (1987) 196(4):901-917.
Chothia, C. et al., "Conformations of immunoglobulin hypervariable regions," Nature (1989) 342(6252):877-883.
Chothia, C. et al., "Structural repertoire of the human VH segments," J. Mol. Biol. (1992) 227:799-817.
Clackson et al., "Making antibody fragments using phage display libraries," Nature (1991) 352(6336):624-628.
Cleek et al., "Biodegradable polymeric carriers for a bFGF antibody for cardiovascular application," Pro. Int. Symp. Control. Rel. Bioact. Mater. (1997) 24:853-854.
Co, M.S. et al., "Genetically engineered deglycosylation of the variable domain increases the affinity of an anti-CD33 monoclonal antibody," Mol. Immunol (1993) 30:1361-1367.
Colman, P.M., "Effects of amino acid sequence changes on antibody-antigen interactions," Research in Immunology (1994) 145:33-36.
Conrouce et al., "Anti-hepatitis C virus (anti-HCV) seroconversion in patients undergoing hemodialysis: comparison of second- and third-generation anti-HCV assays," Transfusion (1994) 34(9):790-795.
Conrouce et al., "Significance of NS3 and NS5 antigens in screening for HCV antibody," Lancet (1994) 343(8901);853-854.

Cummins, B. et al., "Cardiac-specific troponin radioimmunoassay in the diagnosis of acute myocardial infarction," Am. Heart Journal (1987) 113:1333-1344.
Dall'Acqua et al., "Contribution of domain interface residues to the stability of antibody CH3 domain homodimers," Biochem. (1988) 37(26):9266-9273.
During et al., "Controlled release of dopamine from a polymeric brain implant: in vivo characterization," Ann. Neurol. (1989) 25:351-356.
Eng et al., "Internal initiation stimulates production of p8 minicore, a member of a newly discovered family of hepatitis C virus yore protein isoforms," J. Virol. (2009) 83(7):3104-3114.
Erikkson, S. et al., "Comparison of cardiac troponin. Immunoassays variably affected by circulating autoantibodies," Clin. Chem. (2005) 51(5):848-855.
Ferns et al., "Characterisation of a panel of monoclonal antibodies raised against recombinant 1, 6-9, and 19 HCV core protein," J. Med. Virol. (1996) 50(3):221-229.
Filatov, V.L. et al., "Epitope mapping of anti-troponin I monoclonal antibodies," Biochem. Mol. Biol. Int. (1998) 45(6):1179-1187.
Foote, J. et al., "Antibody frame work residues affecting the confirmation of the hypervariable loops," J. Mol. Biol. (1992) 224:487-499.
Fuchs et al., "Targeting recombinant antibodies to the surface of *Escherichia coli*: fusion to a peptidoglycan associated lipoprotein," Biotechnology (1991) 9:1370-1372.
Garrard et al., "FAB assembly and enrichment in a monovalent phage display system," Biotechnology (1991) 9:1373-1377.
Gavilondo et al., "Antibody engineering at the millennium," Biotechniques (2000) 29(1):128-145.
Giege, R. et al., "An introduction to the crystalligenesis of biological macromolecules," Crystallization of Nucleic Acids and Proteins, a Practical Approach, 2nd Edition, Oxford University Press, New York (1999) 20 1-16.
Gillies et al., "High-level expression of chimeric antibodies using adapted cDNA variable region cassettes," J. Immunol. Methods (1989) 125:191-202.
Goodson, J.M. et al., Medical Applications of Controlled Release, Chapter 6, Dental Applications (1984) 2:115-138.
Gram, H. et al., "In vitro selection and affinity maturation of antibodies from a naïve combinatorial immunoglobulin library," Proc. Natl. Acad. Sci. (1992) 89(8):3576-3580.
Green et al, "Antigen-specific human monoclonal antibodies from mice engineered with human Ig heavy and light chain YACs," Nat. Genet. (1994) 7(1):13-21.
Green et al., "Regulation of B cell development by variable gene complexity in mice reconsituted with human immunoglobulin yeast artificial chromosomes," J. Exp. Med. (1998) 188(3):483-495.
Griffiths et al., "Human anti-self antibodies with high specificity from phage display libraries," EMBO J.(1993) 12(2):725-734.
Hawkins et al., "Selection of phage antibodies by binding affinity. Mimicking affinity maturation," J. Mol. Biol. (1992) 226(3):889-896.
Hay, B.N. et al., "Bacteriophage cloning and *Escherichia coli* expression of a human IgM fab," Hum. Antibodies Hybridomas (1992) 3(2):81-85.
Higgins et al., "Fast and sensitive multiple sequence alignments on a micro computer," Cabios (1989) 5(2):151153.
Hino, "Diagnosis of hepatitis C," Intervirology (1994) 37(2):77-86.
Holliger, P. et al., "Diabodies, small bivalent and bispecific antibody fragments," Proc. Natl. Acad. Sci. USA (1993) 90(14):6444-6448.
Hoogenboom et al., "Multi-subunit proteins on the surface of filamentous phage: methodologies for displaying antibody (Fab) heavy and light chains," Nucleic Acids Res. (1991) 19(15):4133-4137.
Hoogenboom et al., "natural and designer binding sites made by phage display technology," Immunol. Today (2000) 21(8):371-378.
Hoogenboom, "Designing and optimizing library selection strategies for generating high-affinity antibodies," Trends Biotechnol .(1997) 15(2):62-70.
Hope et al., "Sequence motifs required for lipid droplet association and protein stability are 1, 6-9, and 19 unique to the hepatitis C virus core protein," J. Gen. Virol. (2000) 81(Pt 8):1913-1925.

(56) References Cited

OTHER PUBLICATIONS

Howard, M.A. et al., "Intracerebral drug delivery in rats with lesion-induced memory deficits," J. Neurosurg. (1989) 71:105-112.
Huber et al., "Crystallographic structure studies of an IgG molecule and an Fc fragment," Nature (1976) 264(5585):415-420.
Huse et al., "Generation of a large combinatorial library of the immunoglobulin repertoire in phage lambda," Science (1989) 246(4935):1275-1281.
Huston et al., "Protein engineering of single-chain Fv analogs and fusion proteins," Methods Enzymol. (1991) 203:46-88.
Hytest 1999 Product Catalog, 3 pages.
Hytest 2000 General Product Catalog, 3 pages.
Hytest 2001 - 2002 General Product Catalog, 3 pages.
Hytest 2001 Cardiac Markers Panel, 4 pages.
Hytest 2003 General Product Catalog, 3 pages.
Hytest 2004 - 2005 General Product Catalog, 3 pages.
Hytest 2004 Cardiac Markers Panel, 4 pages.
Hytest 2005 - 2006 General Product Catalog, 3 pages.
Hytest 2005 Markers of Cardiovascular Diseases Catalog, 4 pages.
Hytest 2006-2007—General Product Catalog, 3 pages.
Hytest 2007-2008 General Product Catalog, 3 pages.
Hytest 2007 markers of Cardiovascular Diseases Catalog, 4 pages.
Hytest 2008-2009 General Product Catalog, 3 pages.
Hytest 2008 Markers of Cardiovascular Diseases and Metabolis Syndrome, 4 pages.
International Search Report and Written Opinion for Application No. Pc/US2013/77499 dated May 20, 2014 (21 pages).
International Search Report and Written Opinion for Application No. PCT/US2010/024979 dated May 6, 2010 (16 pages).
International Search Report and Written Opinion for Application No. PCT/US2013/077504 dated Jul. 1, 2014 (14 pages).
Jackson et al., "In vitro antibody maturation. Improvement of a high affinity, neutralizing antibody against IL-1 beta," J. Immunol. (1995) 154(7:3310-3319.
Jefferis, R. et al., "Glycosylation of recombinant antibody therapeutics," Biotechnol. Prog. (2005) 21:11-16.
Johnsson et al., "Comparison of methods for immobilization to carboxymethyl dextran sensor surfaces by analysis of the specific activity of monoclonal antibodies," J. Mol. Recognit. (1995) 8(1-2):125-131.
Johnsson et al., "Immobilization of proteins to a carboxymethyldextran-modified gold surface for biospecific interaction analysis in surface plasmon resonance sensors," Anal. Biochem. (1991) 198(2):268-277.
Jones et al. "Replacing the complementarity-determining regions in a human antibody with those from a mouse," Nature (1986) 321(6069):522-525.
Jonsson et al., "Introducing a biosensor based techology for real-time biospecific interaction analysis," Ann. Biol. Clin. (Paris) (1993) 51(1):19-26.
Jonsson et al., "Real-time biospecific interaction analysis using surface plasmon resonance and a sensor chip technology," Biotechniques (1991) 11(5):620-627.
Kabat et al, Sequences of Proteins of Immunological Interest, National Institutes of Health, Bethesda, Maryland (1987) and (1991), 4th Edition, 4 pages.
Kabat et al., "Attempts to locate complementarity-determining residues in the variable positions of light and heavy chains," Ann. NY Acad. Sci. (1971) 190:382-393.
Kabat et al., Sequences of Proteins of Immunological Interest, 5th Edition, Department of Health and Human Services, NIH Publication No. 91/3242 (1991), 11 pages.
Katrukha et al., "Degradation of cardiac troponin: implication for reliable immunodetection," Clin. Chem. (1998) 44(12):2433-2440.
Katrukha, "Troponin. Measurement: the concept of a precise immunoassay," Clin. Lab. Internat. (2006) 30(5): 14-16.
Katrukha, "New approach to standardization of human cardiac Troponin I (cTnI)," Scand. J. Clin. Lab. Invest (1999) 59(Suppl 230):124-127.
Katrukha, "Biochemical factors influencing measurement of cardiac troponin I in serum," Clin. Chem. Lab Med. (1999) 37(11/12):1091-1095.
Katrukha, "Antibody selection strategies in cardiac troponin assays," Cardiac Markers, Second Edition 173-185.
Kaufman, R.J. et al., "Amplification and expression of sequences cotransfected with a modular dihydrofolate reductase complementary DNA gene," Mol. Biol. (1982) 159:601-621.
Kellermann et al., "Antibody discovery: the use of transgenic mice to generate human monoclonal antibodies for therapeutics," Curr. Opin. Biotechnol. (2002) 13(6):593-597.
Kettleborough et al., "Isolation of tumor cell-specific single-chain Fv from immunized mice using phage-antibody libraries and the re-construction of whole antibodies from these antibody fragments," Eur. J. Immunol. (1994) 24(4):952-958.
Kim et al., "Identifying amino acid residues that influence plasma clearance of murine IgG1 fragments by site-directed mutagenesis," Eur. J. Immunol. (1994) 24(3):542-548.
Kipriyanov, S.M. et al., "Single-chain antibody streptavidin fusions: tetrameric bifunctional ScFv-complexes with biotin binding activity and enhanced affinity to antigen," Human Antibodies and Hybridomas (1995) 6:93-101.
Kipriyanov, S.M. et al., "Recombinant single-chain Fv fragments carrying c-terminal cysteine residues: production of bivalent and biotinylated miniantibodies," Mol. Immunol. (1994) 31:1047-1058.
Kleinman et al., "Increased detection of hepatitis C virus (HCV)-infected blood donors by a multiple-antigen HCV enzyme immunoassay," Transfusion (1992) 32(9):805-813.
Kohler et al., "Continuous cultures of fused cells secreting antibody of predefined specificity," Nature (1975) 256(5517):495-497.
Kontermann, Antibody Engineering, p. 790, Springer-Verlag, New York (2001).
Kuo et al., "An assay for circulating antibodies to a major etiologic virus of human non-A, non-B hepatitis," Science (1989) 244(4902):362-364.
Kyte et al., "A simple method for displaying the hydropathic character of a protein," J. Mol. Biol. (1982) 157(1):105-132.
Lam et al., "Microencapsulation of recombinant humanized monoclonal antibody for local delivery," Proc. Int'l Symp. Control Rel. Bioact. Mater. (1997) 24:759-760.
Langer et al., "Chemical physical structure of polymers as carriers for controlled release of bioactive agents: a review," J. Macromol. Sci. Rev. Macromol. Chem. (1983) 23:61-126.
Langer et al., "New methods of drug delivery," Science (1990) 249:1527-1533.
Laperche et al., "Simultaneous detection of hepatitis C virus (HCV) core antigen and anti-1, 6-9, and 19 HCV antibodies improves the early detection of HCV infection," J. Clin. Microbiol. (2005) 43(8):3877-3883.
Lee et al., "Increased detection of hepatitis C virus infection in commercial plasma donors by a third-generation screening assay," Transfusion (1995) 35(10):845-849.
Levy, R.J. et al "Inhibition of calcification of bioprosthetic heart valves by local controlled-release diphosphonate," Science (1985) 228:190-192.
Little et al., "Of mice and men: hybridoma and recombinant antibodies," Immunol. Today (2000) 21(8):364-370.
MacCallum et al., "Antibody-antigen interactions: contact analysis and binding site topography," J. Mol. Biol. (1996) 262(5):732-745.
Marchalonis et al., "Evolutionary factors in the emergence of the combinatorial germline antibody repertoire," Adv. Exp. Med. Biol. (2001) 484:13-30.
Marks et al., "By-passing immunization. building high affinity human antibodies by chain shuffling," Biotechnology (NY) (1992) 10(7):779-783.
Mattingly, "Chemiluminescent 10-methyl-acridinium-9-(N-sulphonylcarboxamide) salts> Synthesis and kinetics of light emission," J. Biolumin. Chemilumin (1991) 6(2):107-114.
McCafferty et al., "Phage antibodies: filamentous phage displaying antibody variable domains," Nature (1990) 348(6301):552-554.
McCapra et al., "Chemiluminescence involving peroxide decompositions," Photochemistry and Photobiology 1965) 4:1111-1121.

(56) References Cited

OTHER PUBLICATIONS

Medical Applicants of Controlled Release, Langer and Wise (eds), CRC Press, Boca Raton, Florida (1974).
Mendez et al., "Functional transplant of megabase human immunoglobulin loci recapitulates human antibody response in mice," Nat. Genet. (1997) 15(2):146-156.
Mimms et al., "Specificity of anti-HCV ELISA assessed by reactivity to three immunodominant HCV regions," Lancet (1990) 336(8730):1590-1591.
Mizushima et al., "pEF-BOS, a powerful mammalian expression vector," Nucleic Acids Research (1990) 18:5322-5323.
Morota et al., "A new sensitive and automated chemiluminescent microparticle immunoassay for quantitative determination of hepatitis C virus core antigen," J. Virol. Methods (2009) 157(1):8-14.
Morrison et al., "Numeric human antibody molecules: mouse antigen-binding domains with human constant region domains," Proc. Natl. Acad. Sci. (1984) 81:6851-6855.
Morrison, "Transfectomas provide novel chimeric antibodies," Science (1985) 229(4719):1202-1207.
Mullinax et al., "Expression of a heterodimeric Fab antibody protein in one cloning step," Biotequnicues (1992) 12(6):864-869.
Needleman et al., J. Mol. Biol. (1970) 48:443.
Neuberger et al., "Recombinant antibodies possessing novel effector functions," Nature (1984) 312:604-608.
Ning et al., "Intratumoral radioimmunotherapy of a human colon cancer xenograft using a sustained-released gel," Radiotherapy and Oncology (1996) 39:179-189.
Oellerich, "Enzyme-immunoassay: a review," J. Clin. Chem. Clin. Biochem. (1984) 22(12):895-904.
Oi et al., "Chimeric antibodies," BioTechniques (1986) 4(3):214-311.
Padlan et al., "A possible procedure for reducing the immunogenicity of antibody variable domains while preserving their ligand-binding properties," Mol. Immunol. (1991) 28(4-5):489-498.
Padlan et al., "Identification of specificity-determining residues in antibodies," FASEB J. (1995) 9(1):133-139.
Panina-Bordignon et al., "Universally immunogenic T cell epitopes: promiscuous binding to human MHC class II and promiscuous recognition by T cells," Eur. J. Immunol. (1989) 19(12):2237-2242.
Paul, Fundamental Immunology, 3rd Edition (1993) pp. 292-295, under the heading "FV Structure and Diversity in Three Dimensions".
Pearson et al., "Improved tools for biological sequence comparison," Proc. Natl. Acad. Sci. (1988) 85:2444-2448.
Peronnet et al., "Isoelectric point determination of cardiac troponin I forms present In plasma from patients with myocardial infarction," (2007) 377(1-2):243-247.
Persic et al., "An integrated vector system for the eukaryotic expression of antibodies or their fragments after selection from phage display libraries," Gene (1997) 187(1):9-18.
Poljak, "Production and structure of diabodies," Structure (1994) 2(12):1121-1123.
Presta et al., "Humanization of an antibody directed against IgE," J. Immunol. (1993) 151(5):2623-2632.
Quinn, F. et al., "36 Bulk Reagent Random-access analyzer: Architect; 2000," The Immunoassay Handbook, 2nd Edition (2001) 363-367.
Rama, D. et al., "Epitope localization of monoclonal antibodies used in human troponin I immunoenzymometric assay," Hybridoma (1997) 16(2):153-157.
Razavi et al., "Stable and versatile active acridinium esters I," Luminescence (2000) 15(4):239-244.
Razavi et al., "Stable and versatile active acridinium esters II," Luminescence (2000) 15(4):245-249.
Reverse Translate a Protein (1998) (www.vivo.colostae.edu/molkit/translate/index.html), 1 page.
Riechmann et al., "Reshaping human antibodies for therapy," Nature (1988) 332(6162):323-327.
Roberts et al., "RNA-peptide fusions for the in vitro selection of peptides and proteins," Proc. Natl. Acad. Sci. USA (1997) 94(23):12297-12302.
Roguska et al., "Human ization of murine monoclonal antibodies through variable domain resurfacing," Proc. Natl. Acad. Sci. USA (1994) 91(3):969-973.
Rudikoff et al., "Single amino acid substitution altering antigen-binding specificity," Proc. Natl. Acad. Sci USA (1982) 79(6):1979-1983.
Sambrook et al., A Laboratory Manual, Molecular Cloning, 2nd Edition, Cold Spring Harbor Laboratory Press, Cold Spring Harbor, New York (1989) 30 pages.
Saudek et al., "A preliminary trial of the programmable implantable medication system for insulin delivery," N. Engl. J. Med. (1989) 321:574-579.
Sawai et al., "Direct production of the Fab fragment derived from the sperm immobilizing antibody using polymerase chain reaction and cDNA expression vectors," Am. J. Reprod. Immunol. (1995) 34(1):26-34.
Schier et al., "Identification of functional and structural amino-acid residues by parsimonious mutagenesis," Gene (1996) 169(2):147-155.
Schiestl et al., "High efficiency transformation of intact yeast cells using single stranded nucleic acids as a carrier," Current Genetics (1989) 16(5-6):339-346.
Seligmann et al., "Immunochemical study of a human myeloma IgG1 half molecule," Ann. Immunol. (1978).
Shah et al., "Combination HCV core antigen and antibody assay on a fully automated chemiluminescence analyzer," Transfusion (2003) 43:1067-1074.
Shapiro et al., "DNA target motifs of somatic mutagenesis in antibody genes," Crit. rEv. Immunol. (2002) 22(3): 183-200.
Shavinskaya, A. et al., "The lipid droplet binding domain of hepatitis C virus core protein is a major determinant for efficient virus assembly," J. Biol. Chem. (2007) 282(51):37158-37169.
Shields, R.L. et al., "Lack of fucose on human IgG1 N-linked oligosaccharide improves binding to human FcyRIII and antibody dependent cellular toxicity," J. Biol. Chem. (2002) 277:26733-26740.
Shu et al., "Secretion of a single-gene-encoded immunoglobulin from myeloma cells," Proc. Natl. Acad. Sci. USA (1993) 90(17):7995-7999.
Sims et al., "A humanized CD18 antibody can block function without cell destruction," J. Immunol. (1993) 151(4):2296-2308.
Skerra et al., "Assembly of a functional immunoglobulin Fv fragment in *Escherichia coli*," Science (1988) 240(4855): 1038-1041.
Smith et al., "Comparison of biosequences," Appl. Math. (1981) 2:482-489.
Song et al., "Antibody mediated lung targeting of long-circulating emulsions," PDA Journal of Pharmaceutical Science and Technology (1995) 50:372-377.
Studnicka et al, "Human-engineered monoclonal antibodies retain full specific binding activity by preserving non-CDR complementarity-odulating residues," Protein Eng. (1994) 7(6):805-814.
Table Showing Codon-amino acid Abbreviations (www.hgmd.cfac.uk/docs/cd_amino.html), printed Jan. 23, 2013, 3 pages.
Takeda et al., "Constsruction of chimaeric processed immunoglobulin genes containing mouse variable and human constant region sequences," Nature (1985) 314:452-454.
Tamura et al., "MEGA5: molecular evolutionary genetics analysis using maximum likelihood, evolutionary distance, and maximum parsimony methods," Mol. Biol. Evol. (2011) 28(10):2731-2739.
Taylor et al., "A transgenic mouse that expresses a diversity of human sequence heavy and light chain immunoglobulins," Nucl. Acids Res. (1992) 20(23):6287-6295.
Thies et al., "Folding and association of the antibody domain CH3: prolyl isomerization preceeds dimerization," J. Mol. Biol. (1999) 293(1):67-79.
Thompson et al., "CLUSTAL W: improving the sensitivity of progressive multiple sequence alignment through sequence weighting, position-specific gap penalties and weight matrix choice," Nucl. Acids. Res. (1994) 22(22):4673-4680.

(56) References Cited

OTHER PUBLICATIONS

Umana et al., "Engineered glycoforms of an antineuro-blastoma IgG1 with optimized antibody-dependent cellular cytotoxic activity," Nat. Biotech. (1999) 17:176-181.

Urlaub et al., "Isolation of Chinese hamster cell mutants deficient in dehydrofolate reductase activity," Proc. Natl. Acad. Sci. (1980) 77:4216-4220.

Verhoeyen et al., "Reshaping human antibodies: grafting an antilysozyme activity," Science (1988) 239(4847): 1534-1536.

Wallemacq et al., "Evaluation of the new AxSYM cyclosporine assay: comparison with TDx monoclonal whole blood and EMIT cyclosporine assays," Clin. Chem. (1999) 45(3):432-435.

Wallick, S.C. et al., "Glycosylation of a VH residue of a monoclonal antibody against alpha(1-6) dextran increases its affinity for antigens," Exp. Med. (1988) 168:1099-1109.

Ward et al., "Binding activities of a repertoire of single immunoglobulin variable domains secreted from *Escherichia coli*," Nature (1989) 341(6242):544-546.

West et al., "Crystal structure and immunologbulin G binding properties of the human major histocompatibility complex-related Fc receptor," Biochem. (2000) 39(32):9698-9708.

Winnaker et al., From Genes to Cones, Verlagsgesellschaft, Weinheim, Germany (1987).

Wright, A. et al., "Antibody variable region glycosylation: position effects on antigen binding and carbohydrate structure," EMBO J. (1991) 10:2717-2723.

Wu et al, "Receptor-mediated in vitro gene transformation by a soluble DNA carrier system," J. Biol. Chem. (1987) 262:4429-4432.

Yelton et al., "Affinity maturation of the BR96 anti-carcinoma antibody by codon-based mutagenesis," J. Immunol. (1995) 155(4):1994-2004.

Ylikotila et al., "Utilization of recombinant fab fragments in a cTnI immunoassay conducted in spot wells," Clinc. Biochem. (2006) 39:843-850.

Zapata et al., "Engineering linear F(ab)2 fragments for efficient production in *Escherichia coli* and enhanced antiproliferative activity," Protein Eng. (1995) 8(10):1057-1062.

United States Patent Office Action for U.S. Appl. No. 14/138,991 dated Sep. 21, 2015 (9 pages).

United States Patent Office Action for U.S. Appl. No. 14/139,108 dated Jan. 21, 2015 (11 pages).

United States Patent Office Notice of Allowance for U.S. Appl. No. 14/139,108 dated Jul. 17, 2015 (5 pages).

United States Patent Office Action for U.S. Appl. No. 12/391,937 dated Feb. 24, 2011 (15 pages).

United States Patent Office Notice of Allowance for U.S. Appl. No. 12/391,937 dated Aug. 5, 2011 (13 pages).

United States Patent Office Notice of Allowance for U.S. Appl. No. 14/035,420 dated Feb. 27, 2015 (8 pages).

United States Patent Office Action for U.S. Appl. No. 14/035,420 dated Mar. 18, 2014 (9 pages).

United States Patent Office Action for U.S. Appl. No. 90/012,377 dated Feb. 6, 2013 (15 pages).

European Extended Search Report for Application No. 13878042.4 dated Sep. 29, 2016 (8 pages).

European Extended Search Report for Application No. 13880371.3 dated Oct. 10, 2016 (13 pages).

El-Emshaty et al., "Diagnostic performance of an immunoassay for simultaneous detection of HCV core antigen and antibodies among haemodialysis patients," Brazilian Journal of Microbiology (2011) 42: 303-309.

United States Patent Office Action for U.S. Appl. No. 14/851,471 dated Apr. 20, 2017 (14 pages).

\* cited by examiner

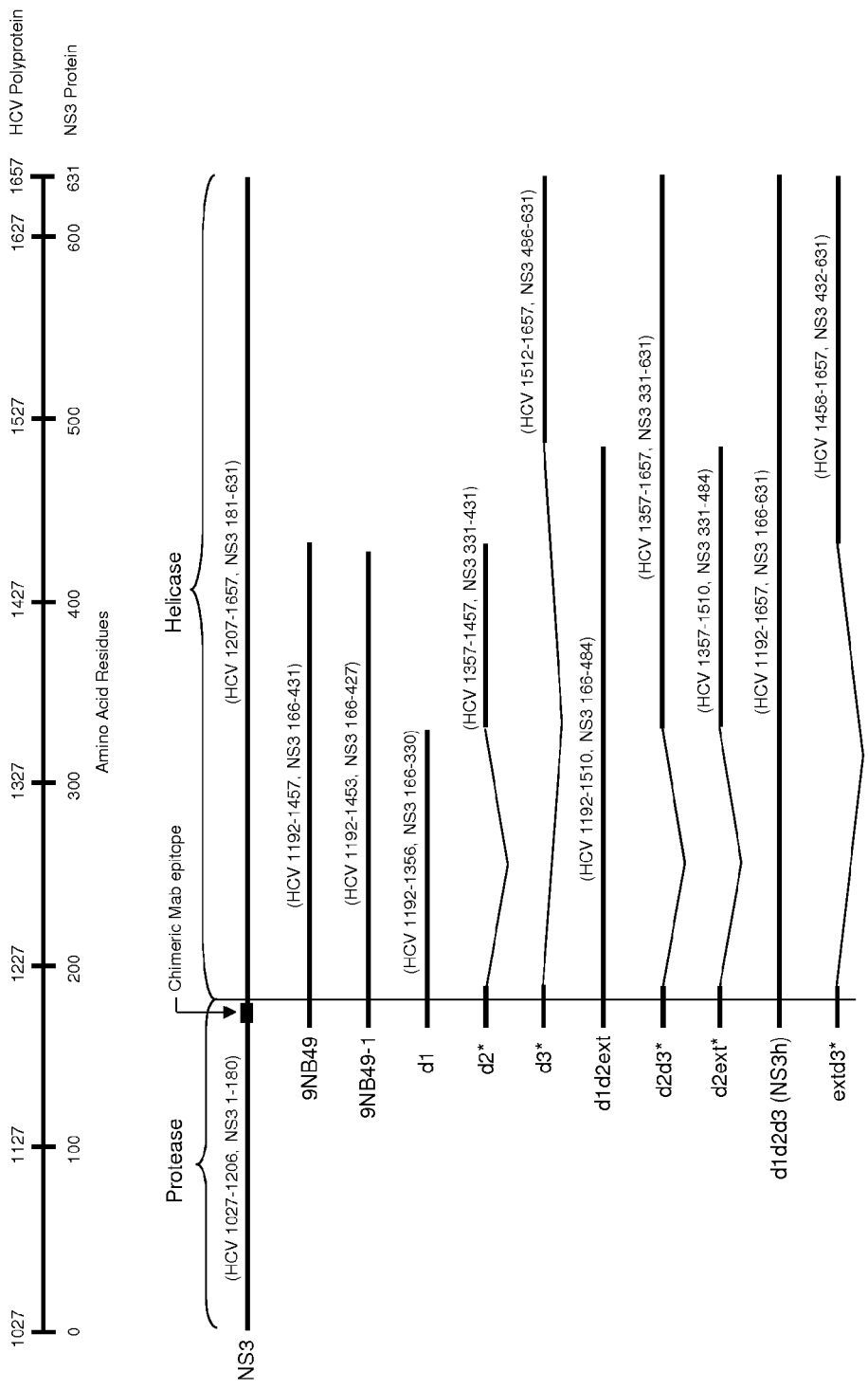

HCV NS3 RECOMBINANT ANTIGENS AND MUTANTS THEREOF FOR IMPROVED ANTIBODY DETECTION

CROSS-REFERENCE TO RELATED APPLICATION(S)

This claims priority to U.S. Provisional Patent Application No. 61/899,514, filed on Nov. 4, 2013, and U.S. Provisional Patent Application No. 61/784,822, filed on Mar. 14, 2013, the entire contents of all of which are fully incorporated herein by reference.

SEQUENCE LISTING

The instant application contains a Sequence Listing which has been submitted electronically in ASCII format and is hereby incorporated by reference in its entirety. Said ASCII copy, created on Jun. 16, 2015, is named 11949USO1_SL.txt and is 309,420 bytes in size.

FIELD OF THE INVENTION

The present disclosure relates to polypeptides, including fusions thereof, nucleic acids, vectors, host cells, immunodiagnostic reagents, kits, and immunoassays for use detecting the presence of HCV antibodies.

BACKGROUND OF THE INVENTION

According to WHO statistics, as many as 170 million people worldwide are infected by hepatitis C virus (HCV), a viral infection of the liver. 75 to 85% of persons infected with HCV progress to chronic infection, approximately 20% of these cases develop complications of chronic hepatitis C, including cirrhosis of the liver or hepatocellular carcinoma after 20 years of infection. The current recommended treatment for HCV infections is a combination of interferon and ribavirin drugs, however the treatment is not effective in all cases and liver transplantation is indicated in hepatitis C-related end-stage liver disease. At present, there is no vaccine available to prevent HCV infection, therefore all precautions to avoid infection must be taken.

Thus, patient care, as well as the prevention of transmission of Hepatitis C Virus (HCV) by blood and blood products or by close personal contact requires extreme vigilance using sensitive detection assays. This creates a need for specific methods for screening and identifying carriers of HCV and HCV-contaminated blood or blood products. Serological determination of HCV exposure relies on the detection of anti-HCV antibodies present in human blood plasma or sera. These anti-HCV antibodies are directed against a number of distinct structural and non-structural proteins encoded by the virus.

The HCV virus is a (+) sense single-stranded enveloped RNA virus in the Hepacivirus genus of the Flaviviridae family. The viral genome is approximately 10 kb in length and encodes a 3011 amino acid polyprotein precursor. The HCV genome has a large single open reading frame (ORF) coding for a unique polyprotein. This polyprotein is co- and post-translationally processed by cellular and viral proteases into three structural proteins, i.e., core, E1 and E2 and at least six non-structural NS2, NS3, NS4A, NS4B, NS5A and NS5B proteins. (Choo et al., Science 244: 359-362 (1989)).

There are commercially available assays that determine whether a subject has been exposed to HCV. These serological assays typically use an indirect format in which anti-HCV antibodies are captured by recombinant HCV antigens present on a solid phase, followed by detection of the anti-HCV antibody by a labeled anti-human antibody conjugate. While some of the antigenic regions of HCV have been identified, peptides and recombinant proteins from these regions exhibit a variable degree of sensitivity and selectivity in detection and diagnosis of HCV carriers.

For example, HC43 is one such recombinant protein used for the detection of HCV antibodies in human serum or plasma. HC43 contains the C33 region of the NS3 protein (HCV-1 amino acids 1192-1457) and the core or nucleocapsid structural protein (HCV-1 amino acids 1-150). HC43 is expressed in E. coli as a fusion protein by using a plasmid (pKRR826) containing the pL promoter of bacteriophage lambda (described in U.S. Pat. No. 6,846,905), utilizing a codon-optimized sequence from the HCV H strain (i.e., HCV-1; Ogata et al., PNAS USA 88: 3392-3396 (1991)). Two non-HCV coding amino acids separate the NS3 and core sequences. There are commercially marketed anti-HCV assays using such a fusion protein. The expression of this fusion protein in E. coli via a temperature inducible system results in the formation of insoluble inclusion bodies. These must be solubilized with urea, reductant and SDS in order to obtain pure, monomer protein for use in the immunoassay (as solid phase antibody capture reagent). Derivatives of this protein (e.g. 9MB31) disclosed in US patents owned by Abbott comprise truncated core protein sequences and are expressed in temperature inducible systems yielding protein that is insoluble.

Another such recombinant protein used for the detection of anti-HCV antibodies is C100. This recombinant protein is derived from the NS3 and NS4 regions of the HCV genome (HCV amino acids 1569-1931), and is expressed in yeast with an N-terminal superoxide dismutase (SOD) fusion of 527 amino acids (see, e.g., U.S. Pat. No. 5,350,671). Although 363 amino acids of the HCV genome are present in the recombinant protein, studies have demonstrated that the majority of antibody binding occurs in two smaller regions within the NS4 region. The first region is the 5-1-1 region, which comprises HCV amino acids 1691-1733, and the second is the C100 region made up of HCV amino acids 1921-1940.

Other NS3 helicase constructs used for immunoassay development have been described by Jin and Petersen (Archives or Bioch Biophys, 1995, 323:47-53; Sallberg et al., 1996, J Gen Virol, 77:2721-2728; Chien et al. 1998, Hepatology, 28:219-224) but these constructs encompass residues 1207-1612 and do not included the full length helicase (1207-1657). In addition, the aforementioned proteins are again expressed in insoluble form and purified under denaturing conditions and require protein refolding techniques in order to regain enzymatic activity, prior to their use in immunoassays.

Many HCV diagnostic assays make use of an NS3 antigen, in different forms. HCV NS3 is a multifunctional protein, containing a serine protease domain within its N-terminal third and an NTPase/helicase domain within its C-terminal two-thirds. Polynucleotide-stimulated NTPase activity, capable of hydrolyzing all NTPs and dNTPs, has been shown, while RNA helicase activity, requiring ATP and a divalent ion, has also been identified: the NS3 C-terminal domain is capable of unwinding RNA-RNA, RNA-DNA and DNA-DNA substrates in a 3'-5' direction.

Crystal structure analysis of the HCV NS3 helicase has shown that this enzyme is composed of three domains. Domain I (approximately residues 181-326 of NS3) and Domain II (approximately residues 327-481 of NS3) have little sequence identity, but share similarities in structure being composed of a large central β-sheet flanked by α-helices, and are homologous in structure to the central region of the RecA protein. Domain III (approximately residues 482-631 of NS3) is mostly α-helical and contains part of the single-stranded nucleic acid binding site. Domains I and III share a more extensive interface than either share with Domain II. Therefore, Domains I and III form a rigid unit, whereas Domain II is connected to Domains I and III by solvent-exposed polypeptide segments capable of supporting large scale, relative rotations of Domain II. In particular, an unusual molecular feature is a long antiparallel β-loop that extends from the central β-sheet of Domain II to Domain III where the end of the loop becomes an integral part of the domain III structure. Thus, similar to other helicases, domain motions are characteristic for the activity of the HCV helicase (see Gu & Rice, PNAS, 2010, 107: 521-528 and references therein).

While there are some commercially available assays for serological determination of HCV infection using NS3 antigens these assays still need improvement to allow their use for detection earlier within the HCV infection window. Thus, there remains a need for additional assays having increased sensitivity by reducing the HCV antibody seroconversion window. The present invention addresses this need by providing improved sensitivity of anti-NS3 detection in such serological assays.

BRIEF SUMMARY OF THE INVENTION

In preferred embodiments, the present invention is directed to a recombinant HCV NS3 antigen comprising a NS3 helicase sequence that comprises each of domains I, II and III of said helicase, wherein said antigen has increased immunoreactivity against HCV antibodies from serum as compared to C33 antigen, wherein said recombinant HCV NS3 antigen comprises one or more of the characteristics selected from the group consisting of:

diminished ATP-binding activity as compared to the ATP-binding activity of wild-type NS3 helicase diminished ATPase activity as compared to wild-type NS3 as compared to the ATP-binding activity of wild-type NS3 helicase, and increased redox stability as compared to the redox stability of wild-type NS3 helicase.

Particularly preferred antigens of the invention further comprises addition of at least one cysteine residue in the C-terminus end of said NS3 helicase. In the context of the present invention, the wild-type HCV NS3 comprises a sequence of SEQ ID NO: 87 and wherein the recombinant antigen of the invention comprises at least one mutation as compared to the sequence of SEQ ID NO:87. More particularly, the mutation comprises a mutation of one or more of the cysteine residues of said SEQ ID NO:87 to any other amino acid. More specifically, the mutation comprises a mutation of said one or more cysteine residues to corresponding serine residues. In more particular embodiments, the mutation comprises one or more of the mutations of the cysteine residues from Domain III of HCV NS3 helicase. Even more specifically, in preferred embodiments, the cysteine residue mutation comprises a mutation of one or more of the cysteine residues selected from the group consisting C292, C368, C374, C499, and C525 of SEQ ID NO:87. In some antigens of the invention, the HCV NS3 mutant is one in which at least two of said cysteine residues are replaced by corresponding serine residues.

In another aspect of the invention, the HCV NS3 antigen further comprises addition of at least one cysteine residue at the C-terminus end of said NS3 helicase. In certain specific embodiments, the HCV NS3 antigen comprises two additional cysteine residues at the C-terminus end of said NS3 helicase. In additional embodiments, the NS3 antigen comprises a mutation that diminishes ATP binding or diminishes ATPase activity is a replacement of one or more of the amino acid residues selected from the group consisting of K210, S211, T212, Y241, D290, E291, H293, T419, Q460, R464, R467 and W501 of SEQ ID NO:87 with any other amino acid residue. Exemplary mutations include but are not limited to a mutation selected from the group consisting of K210N, S211A, T212E, Y241S, D290N, E291Q, H293A, T419G, Q460H, R464A, R467K and W501A as compared to SEQ ID NO:87.

In any of the embodiments in which the mutation comprises a mutation of K210, S211, T212, Y241, D290, E291, H293, T419, Q460, R464, R467 and W501 of SEQ ID NO:87 with another amino acid, the antigen may further comprise a mutation of one or more of the cysteine residues of SEQ ID NO:87 to any other amino acid. More specifically, the one of more mutation of one or more of the cysteine residues of said SEQ ID NO:87 comprises a mutation of one or more of the cysteine residues selected from the group consisting C292, C368, C374, C499, and C525 of SEQ ID NO:87. The antigen may advantageously further comprise addition of at least one additional cysteine residue at the C-terminus end of said NS3 helicase. For example, such an additional cysteine residue may be introduced by addition of a cysteine residue at the C-terminus end of said NS3 helicase comprises addition of a sequence selected from the group consisting of GGCSGGA (SEQ ID NO: 82), DECHSTD (SEQ ID NO: 84), and SKKKCDE (SEQ ID NO: 86) to the C-terminus end of said NS3 helicase. In other specific embodiments, the antigen may comprise two additional cysteine residues. In specific embodiments, the two additional cysteine residues are introduced by addition of a sequence selected from the group consisting of GSGSGH-HHHHHHHGGCSGGARSGC (SEQ ID NO: 89); GSGS-GHHHHHHHHDECHSTDRSGC (SEQ ID NO: 90); and GSGCGHHHHHHHHGGCSGGA (SEQ ID NO: 91). Other exemplary additional cysteine residues are introduced by a C-terminal sequence comprising GSGSGHHHHHHHHG-GCSGGA (SEQ ID NO: 92), GSGSGHHHHHHHHDECH-STD (SEQ ID NO: 93), GSGSGHHHHHHHHSKKKCDE (SEQ ID NO: 94), and GSGSGHHHHHHHHSKK-KCDERSGC (SEQ ID NO: 95).

In further embodiments, the C-terminus sequence may be modified by conjugation to a signal generating moiety.

In still additional embodiments, the antigen may further comprise a histidine tag. More specifically, the histidine tag may be located between the C-terminus of SEQ ID NO:87 and the N-terminus of said added sequence.

Any of the preferred antigens of the present invention may be biotinylated. Preferably, the biotinylation is at the N-terminus or alternatively at the C-terminus of said antigen. In alternative embodiments, the biotinylation is site-specific biotinylation.

A further aspect of the invention relates to an isolated nucleic acid encoding a recombinant HCV antigen of the present invention. In addition the invention further comprises an expression vector comprising such an isolated nucleic acid. Additionally, the invention comprises a host cell transformed or transfected with such an expression vector, for examples the host cell may be an *E. coli* cell.

The invention further is related to an immunodiagnostic reagent, one or more of them comprising the recombinant HCV antigens of the present invention. In some embodiments, the immunodiagnostic reagent may further comprise a solid support. For example, the solid support may be a microparticle and the recombinant antigen is coated on said microparticle.

In additional embodiments, the recombinant antigen may be detectably labeled with, but not limited to, a colorimetric, chemiluminescent or fluorescent label.

Any one or more of the antigens of the present invention may be provided in a kit comprising an immunodiagnostic reagent and further comprising an additional isolated HCV antigen comprising an epitope that is immunoreactive with an anti-HCV antibody. In exemplary embodiments, the additional HCV antigen is an HCV core antigen. In specific embodiments, kits comprise a recombinant HCV NS3 antigen of the invention and an additional HCV antigen co-coated on the same solid phase. In other embodiments, the recombinant HCV NS3 antigen of the invention and the core antigen are coated on the separate solid phases.

Kits of the invention preferably further comprise antibodies for detection of human antibodies. Additionally, kits may further comprise anti-HCV antibodies, optionally comprising a detectable label.

Also contemplated by the present invention is an immunoassay method of determining the presence of anti-HCV antibodies in a test sample, comprising contacting said test sample with an immunodiagnostic agent of the invention under conditions to allow a complex to form between said recombinant HCV NS3 antigen and said anti-HCV antibodies in said test sample, and detecting the presence of said complex, wherein presence of said complex is indicative of anti-HCV antibodies in said test sample. In preferred embodiments, the detection of the complex formation is detected by determining binding of labeled (for example, fluorescently labeled) anti-human antibodies to the complex. In specific embodiments the fluorescent label preferably is acridinium.

In preferred embodiments, the recombinant HCV NS3 antigen is coated on microparticles.

In the immunoassays of the invention, the method may further comprise assaying the test sample to determine the presence of antibodies against HCV core antigen. In the immunoassays of the invention, the antigens of the present invention as well as additional antigens, such as e.g., core antigens are co-coated onto the same microparticle or alternatively such antigens may be coated on separate microparticles.

Any of the immunoassays of the invention may be used on test samples wherein the test sample is obtained from a patient and the method further comprises diagnosing, prognosticating, or assessing the efficacy of a therapeutic/prophylactic treatment of the patient, wherein, if the method further comprises assessing the efficacy of a therapeutic/prophylactic treatment of the patient, the method optionally further comprises modifying the therapeutic/prophylactic treatment of the patient as needed to improve efficacy.

Any of the immunoassays employing the antigens of the invention may readily be adapted for use in an automated system or a semi-automated system.

In preferred embodiments, the present invention also relates to recombinant HCV NS3 antigen comprising a NS3 helicase sequence that comprises each of Domains I, II and III of said helicase, wherein said antigen has increased immunoreactivity against HCV antibodies from serum as compared to C33 antigen, wherein said recombinant HCV NS3 antigen comprises increased redox stability as compared to the redox stability of wild-type NS3 helicase.

In yet another embodiment a preferred antigen is a recombinant HCV NS3 antigen comprising a NS3 helicase sequence that comprises each of Domains I and II of said helicase, wherein said antigen has increased immunoreactivity against HCV antibodies from serum as compared to C33 antigen, and wherein said recombinant HCV NS3 antigen comprises increased redox stability as compared to the redox stability of wild-type NS3 helicase.

BRIEF DESCRIPTION OF SEVERAL VIEWS OF THE DRAWINGS

FIG. 1 shows the position of HCV NS3 recombinant antigens of the present invention.

DETAILED DESCRIPTION OF THE INVENTION

As discussed above, there is a need to produce additional reagents for sensitive serological assays that may be used for the detecting HCV infection of a sample. The present invention describes recombinant antigens comprised of sequences encoded by the helicase of HCV1 NS3 and methods for expression in *E. coli* in soluble form. The antigens contain polyhistidine tags at their C-termini to facilitate purification via immobilized affinity metal chromatography.

In particular embodiments, the present invention creates specific mutants of HCV1 NS3 that possess amino acid sequences at either the N-terminus or the C-terminus that are targets for covalent attachment of biotin via an enzymatic process. The in vivo biotinylation of these tags occurs inside the cell wherein a biotin ligase enzyme is coexpressed and biotin is added to the culture medium. In this manner the antigens of the invention may be bound to a solid support, precipitated or otherwise monitored through the use of an avidin (or streptavidin, neutravidin, anti-biotin antibody or biotin-binding fragment thereof, or any biotin capture moeity) interaction with the biotin.

In additional embodiments, mutants of the NS3 gene were created in which the cysteine codons were replaced by serine codons either singly or in combination. The creation of cysteine-serine mutants allows for resistance of the antigen to oxidation thereby preserving epitope presentation and hence immunoreactivity.

In addition, at least one of these Cys-to-Ser mutations and other mutants are created that disrupt the ability of full length helicase enzyme (HCV amino acid 1207-1657) to bind nucleotide triphosphates (e.g. ATP) thereby maintaining the protein in an open or extended conformation (see Gu & Rice, PNAS, 2010, 107:521-528 and references therein); some of these mutants demonstrate enhanced immunoreactivity as compared to the wild type full length helicase. Without being bound to a particular theory or mechanism of action, it is possible that by solvent exposure which produces the extended conformation of the helicase yields a more immunoreactive protein. Hence, by modification of the cysteine residues to serine residues or via other mutations, the helicase may be produced in the more immunoreactive extended conformation which better presents the epitopes for binding to the antibodies within the sample being assayed.

In addition, the present invention contemplates an additional series of mutants that comprise short amino acid tag sequences containing one or more cysteine residues added to the C-terminus of the full-length helicase protein. An addition of at least one such additional cysteine residue at the C-terminal end of the antigen allows for conjugation of signal-generating moieties in a site-specific or site-preferential fashion. It has been found that surprisingly, the addition of amino acid tag sequences that comprise two cysteine residues results in enhanced post-purification stability of the recombinant antigen. The antigen produced with such additional cysteine residues is advantageously a protein that is essentially monomeric and possesses thiols for subsequent conjugation to a signal generating moiety. In this manner, the antigens can be directly labeled with the signal generating moiety, using well known techniques, such as maleimide chemistry. The additional sites for signal-generating moieties created by the presence of the extra accessible cysteine residues allow an increased signal to be generated from the antigen. Moreover, the inclusion of these highly solvent exposed cysteine-containing sequence tags at the C-terminus of the helicase allows for site-specific labeling thereby avoiding labeling at other sites that may possess critical epitopes which could be rendered immunologically inert by the non-specific labeling. The particularly preferred tags that include a His-tag for use in introduction of the two additional cysteine residues are:

GSGSGHHHHHHHHGGCSGGARSGC (SEQ ID NO: 89);
GSGSGHHHHHHHHDECHSTDRSGC (SEQ ID NO: 90);
and
GSGCGHHHHHHHHGGCSGGA (SEQ ID NO: 91).

It is noted that purified recombinant proteins for use as antigens in the present invention are labeled with acridinium or via acridinylated-BSA using a heterobifunctional linker containing a maleimide and NHS active groups. In order to achieve high conjugation reaction efficiency, the purified NS3 antigen proteins must be chemically reduced and desalted prior to conjugation. In size exclusion chromatography studies it was seen that the compositions of the invention having the additional cysteine residues at the C-terminus have a low degree of aggregation (or multimerization) as compared to HCV NS3h constructs possessing a single cysteine in the C-terminal tag. This absence of oligomers (multimers or aggregates) is advantageous for maximum sensitivity (no masked epitopes) and specificity (lesser nonspecific binding) and stability (no time-dependent multimerization, oligomerization, aggregation). Without being bound to a particular theory or mechanism of action, it is possible that the introduction of the terminal thiols of the cysteine side chains within the C-terminal tag allow for formation of an intrachain disulfide bond thereby protecting each thiol from oxidation (i.e. reaction with molecular oxygen). This disulfide bond is readily reduced prior to oxidation, thereby rendering the thiols available for labeling using for example direct labeling techniques such as maleimide chemistry.

Unlike all previous assays describing the use of NS3-based antigens, the NS3 antigens described herein are site-specifically biotin labeled, soluble, and monomeric and exhibit reduced oxidation sensitivity yet retains sufficient immunoreactivity to be used in antibody detection assays. Furthermore, the present invention comprises the entire helicase protein region encoded by the C-terminal portion of NS3. This is the first demonstration of the use of the full-length soluble helicase protein for antibody detection for improved seroconversion sensitivity. These NS3 antigens described herein and their soluble expression and purification in the absence of chaotropes or detergents allows for efficient and well controlled conjugation. These antigens are then amenable for use in highly potent (i.e. sensitive) immunoassays for detection of antibodies directed to HCV NS3 helicase by using the full length helicase protein as described below.

The expressed antigens were purified in a two-step process using IMAC and ion exchange chromatography. Due to the soluble expression of the majority of the NS3 proteins and mutants, denaturing conditions (e.g. use of urea, SDS or the like) were not required. In addition, it was discovered that immunoreactivity of the antigens containing cysteine residues could be preserved by inclusion of divalent cation chelator (EDTA or DTPA) during purification and storage of the protein. Without being bound to a particular theory or mechanism of action, it is demonstrated that the antigens of the present invention are more readily detected (i.e., are more immunoreactive) by antibodies in the test sample than the C33 antigen. It is believed that this increased immunoreactivity of the antigens of the present invention is due to their solubility and/or to their modifications/mutations herein. For example, the mutations of the present invention produce one or more of the following characteristics in the antigens which render the antigens more immunoreactive: (a) presence of cysteine to serine mutations in the helicase domain allows resistance of the antigen to oxidation thereby preserving epitope presentation and hence immunoreactivity; (b) addition of domains to expand the inventory of epitopes; and (c) enhancement of existing epitope recognition. Mutation of other cysteine residues that are not specific for immunoreactivity helps restrict site-specific modification of the protein via chemical conjugation using maleimide reagents.

DEFINITIONS

The present invention provides reagents for the detection of anti-HCV antibodies in a test sample. Throughout the specification certain terms are frequently used and as such the following section provides additional definitions of those terms. The term "antibody" (Ab) and "antibodies" (Abs) refer to monoclonal antibodies (mAb (singular) or mAbs (plural)), polyclonal antibodies (pAbs (plural)), multispecific antibodies, human antibodies, humanized antibodies (fully or partially humanized; a polypeptide comprising a modified variable region of a human antibody wherein a portion of the variable region has been substituted by the corresponding sequence from a non-human sequence and wherein the modified variable region is linked to at least part of the constant region of a human antibody), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies (cAb; a polypeptide comprising all or a part of the heavy and light chain variable regions of an antibody from one host species linked to at least part of the antibody constant regions from another host species), single chain antibodies, single domain antibodies, Fab fragments, F(ab') fragments, Fab'-SH fragments, F(ab')2 fragments, Fd fragments, Fv fragments, single-chain Fv fragments ("scFv"), disulfide-linked Fv fragments ("sdFv"), dAb fragments, diabodies, an isolated complementarity determining region (CDR), and anti-idiotypic ("anti-Id") antibodies, bifunctional or dual-domain antibodies (e.g., dual variable domain antibodies, or DVD-IgGs), and functionally active, epitope-binding fragments (or antigenically reactive fragments) of any of the above. In particular, antibodies include immunoglobulin molecules and immunologically active (or antigenically reactive) fragments of immunoglobulin molecules, namely, molecules that contain an analyte-binding site as further described in (n) herein, and variants as further described in (ac) herein Immunoglobulin molecules can be of any type (for example, IgG, IgE, IgM, IgD, IgA and IgY), class (for example, IgG1, IgG2, IgG3, IgG4, IgA1 and IgA2), or subclass. An antibody, whose affinity (namely, KD, kd or ka) has been increased or improved via the screening of a combinatory antibody library that has been prepared using bio-display, is referred to as an "affinity maturated antibody." For simplicity sake, an antibody against an analyte is frequently referred to herein as being either an "anti-analyte antibody" or merely an "analyte antibody" (e.g., an anti-HCV antibody or an HCV antibody). A variant of an antibody is as described in (x) herein.

In the present invention the assay "component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide as described herein, which is optionally immobilized on a solid support. Some components can be in solution or lyophilized for reconstitution for use in an assay.

In conducting the assays of the present invention, it may be useful to use a control. "Control" refers to a composition known to not contain anti-HCV antibody ("negative control") or to contain anti-HCV antibody ("positive control"). A positive control can comprise a known concentration of anti-HCV antibody. "Control," "positive control," and "calibrator" may be used interchangeably herein to refer to a composition comprising a known concentration of anti-HCV antibody. A "positive control" can be used to establish assay performance characteristics and is a useful indicator of the integrity of reagents (e.g., analytes).

The NS3 antigens of the present invention are useful in serological assays for the detection of anti-HCV antibodies in a test sample because such antibodies recognize epitopes contained within the NS3 antigens of the present invention. "Epitope," "epitopes" and "epitopes of interest" refer to a site(s) on any molecule (in this case the NS3 antigens described herein) that is recognized and can bind to a complementary site on a specific binding partner, such as an antibody or antigenically reactive fragment thereof. An epitope consists of the precise amino acid residues of a region of an antigen (or fragment thereof) known to bind to the complementary site on the specific binding partner. An antigenic fragment can contain more than one epitope.

In the assays that are described herein, one or other component of the assay may comprise a detectable label. The terms "label" and "detectable label" mean a moiety attached to a specific binding partner, such as an antibody or an analyte, to render the reaction between members of a specific binding pair, such as an antibody and an analyte, detectable, and the specific binding partner, e.g., antibody or analyte, so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

"Linking sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine residues (His tags), such as a 6xHis tag (SEQ ID NO: 122), which contains six histidine residues, are useful as linking sequences to facilitate the isolation and purification of polypeptides and antibodies of interest. (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, an mAb, for example, can contain a linking sequence, such as a His tag, an enterokinase cleavage site, or both.

"Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human at risk for HCV infection or a human infected with HCV.

In analysis of the results of the immunoassays described herein it may be useful to include certain levels of detection as cutoff levels. "Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

As described below, it may be desirable in some embodiments of the invention to provide a pretreatment of the test sample. "Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., anti-HCV antibody) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

The assays also may be subject to rigorous quality control. "Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

The terms "sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Preferably, the sample is urine, serum or plasma.

In some assays, it may be desirable to provide calibration of the assay. "Series of calibrating compositions" refers to a plurality of compositions comprising a known concentration of anti-HCV antibody, wherein each of the compositions differs from the other compositions in the series by the concentration of anti-HCV antibody.

Throughout the present specification, it is noted that the NS3 antigens and/or other reagents may be bound to a solid support or solid phase, both of which terms are used interchangeably. The term "solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

In certain descriptions of the assays described herein it may be useful to refer to either the NS3 antigen or the HCV antibody as a specific binding partner. "Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced. The term "specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to a given antigen (or a fragment thereof) and not bind specifically to other entities.

Antigens of the Present Invention

The HCV NS3 protein and mutants thereof to be described herein refers principally to two main proteins, the first corresponds to amino acids 1192-1457 per the HCV polyprotein numbering of P26664 (Genbank, reproduced herein as SEQ ID NO:88; Choo et al., PNAS 1991;) also known as C33 (as described originally by Chiron) or as "9NB49H". The second main NS3 protein corresponds to amino acids 1192-1657 also known as NS3 helicase or "NS3h".

The C33 antigen has previously been used in commercial immunoassays. However, it has been recognized that the C33 antigen is thermally instable. This thermal instability is thought to be due to the fact that the C33 antigen undergoes protein degradation, aggregation (in solution and/or on the beads) and conformational changes or combinations of all three. Hence, C33 is not adequate as an antigen for immunoassays designed to determine the presence of NS3-binding antibodies in a test sample. The antigens of the present invention have an increased stability and immunoreactivity to antibodies in a test sample as compared to C33, and hence produce a more sensitive assay.

Variants of the C33 and the NS3 helicase proteins were created in which the N-termini or C-termini sequences were modified. In some embodiments, antigens were created that included cysteine to serine mutations. These mutations allowed for increased resistance of the antigen to oxidation thereby preserving epitope presentation and hence immunoreactivity. Furthermore, at least some of the cysteine to serine substituted mutants, and other non-cysteine mutants, disrupt the ability of full length helicase enzyme (HCV aa1192-1657) to bind nucleotide triphosphates (e.g. ATP). This maintains the protein in an open or extended conformation (see Gu & Rice, PNAS, 2010, 107:521-528 and references therein) and is shown in the present invention to produce enhanced immunoreactivity.

Additionally, the antigens of the invention were further modified to encode biotinylation tags (bt) at either the carboxy or the amino terminus. These tags were designated as "Cbt" or "Nbt" wherein the tags are located at the C-terminus or N-terminus respectively. For production purposes, the recombinant proteins were expressed in *E. coli* BL2L(DE3) cells via an IPTG induction system at 25° C. In situ biotinylation at the Cbt or Nbt tags is accomplished by co-transformation of the BL21(DE3) cells with the HCV NS3 expression plasmid and a second plasmid containing the BirA gene which encodes the biotin ligase enzyme from *E. coli* (Weiss et al. (1994) Protein Expression & Purif, 14:751-755; Schatz et al. (1993) Biotechnology, 11:1138-1143). Final purification of the NS3 proteins is performed in the presence of divalent cation chelators that are shown to prevent metal-catalyzed oxidation and aggregation of the protein. Protein stability is significantly improved when EDTA or related divalent cation chelator is added to the buffers used during purification and to the final storage buffer or buffers used in the immunoassay.

The biotinylation is one method used for the capture of molecules of interest in the assays of the present invention. As noted herein throughout the methods of the invention typically are immunoassay methods. In exemplary embodiments, such methods include methods for isolating a molecule of interest (such as for example a specific antibody that is present in a test sample, or a specific antigen that may be present in the test sample). In order to facilitate such isolation, the molecule of interest comprises or is attracted to a purification tag that contacts a tag binding partner. The association of the purification tag and the tag binding partner thus may be used to separate the molecule of interest from a mixture of molecules. Purification tags can comprise moieties with the same or similar structures. In certain embodiments, the tagging moiety of an affinity tag can be associated with a functional tag directly by a single bond or via a linkage of stable chemical bonds, in linear, branched or cyclic arrangements, optionally including single, double, triple bond, aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and any combination thereof. In certain embodiments, the association between the tagging moiety and functional tag comprises ether, thioether, carboxamide, sulfonamide, urea or urethane moieties. In preferred embodiments, the linkage comprises a polyalkylene chain, i.e., a linear or branched arrangement of carbon-carbon bonds. In other embodiments, the linkage comprises a polyalkylene oxide chain, including a polyethylene glycol moiety. Examples, of affinity tags include, but are not limited to, biotin, digoxigenin (Dig), dinitrophenol (DNP), zinc fingers, fluorinated polymers, and polypeptide sequences such as polyhistidine motifs.

The affinity tags are in some embodiments advantageously used to isolate the molecule of interest by relying on the binding or attraction of the affinity tag and a functional group that is attracted to or binds the affinity tag. In some embodiments, solid substrates having an affinity for the tag in that the solid substrate is derivatized with the tag binding partner. In some embodiments, the binding partner may be immobilized on an affinity substrate. The term "affinity substrate" can refer to an immobile matrix or support bound to a binding partner that is capable of forming a strong and preferably reversible interaction with the purification tag of a molecule. An affinity substrate can include a resin, a bead, a particle, a membrane, a gel. The binding partner recognizes or binds to the purification tag specifically. Specific binding partners will depend on the affinity tag, but include charged moieties and one member of a binding pair such as receptor-ligand, antibody-antigen, carbohydrate-lectin, and biotin-streptavidin (or avidin, neutravidin or an anti-biotin antibody).

The following Table 1 shows exemplary modified NS3h antigens of the present invention:

TABLE 1

| Antigen designation | Antigen | Sequence |
|---|---|---|
| A | K210N | avdfipven lettmrspvf tdnssppvvp qsfqvahlha ptgsgNstkv paayaaqgyk vlvlnpsvaa tlgfgaymsk ahgidpnirt gvrtittgsp itystygkfl adgg*C*sggay diii*cdeC*hs *t*datsilgig tvldqaetag arlvvlatat ppgsvtvphp nieevalstt geipfygkai plevikggrh lif*c*hskkk*C* *d*elaaklval ginavayyrg ldvsviptsg dvvvvatdal mtgytgdfds vid*c*nt*c*vtq tvdfsldptf tietitlpqd avsrtqrrgr tgrgkpgiyr fvapgerpsg mfdssvl*cec* ydag*c*awyel tpaettvrlr aymntpglpv cqdhlefweg vftglthida hflsqtkqsg enlpylvayq atv*c*araqap ppswdqmwk*c* lirlkptlhg ptpllyrlga vgneitlthp vtkyimtcms adlevvt (SEQ ID NO: 105) |
| B | S211A | avdfipven lettmrspvf tdnssppvvp qsfqvahlha ptgsgkAtkv paayaaqgyk vlvlnpsvaa tlgfgaymsk ahgidpnirt gvrtittgsp itystygkfl adgg*C*sggay diii*cdeC*hs *t*datsilgig tvldqaetag arlvvlatat ppgsvtvphp nieevalstt geipfygkai plevikggrh lif*c*hskkk*C* *d*elaaklval ginavayyrg ldvsviptsg dvvvvatdal mtgytgdfds vid*c*nt*c*vtq tvdfsldptf tietitlpqd avsrtqrrgr tgrgkpgiyr fvapgerpsg mfdssvl*cec* ydag*c*awyel tpaettvrlr aymntpglpv cqdhlefweg vftglthida hflsqtkqsg enlpylvayq atv*c*araqap ppswdqmwk*c* lirlkptlhg ptpllyrlga vgneitlthp vtkyimtcms adlevvt (SEQ ID NO: 106) |

TABLE 1-continued

| Antigen designation | Antigen | Sequence |
|---|---|---|
| C | T212E | avdfipven lettmrspvf tdnssppvvp gsfqvahlha ptgsgksEkv paayaaqgyk vlvlnpsvaa tlgfgaymsk ahgidpnirt gvrtittgsp itystygkfl ad*ggcsggay* diii*c*d*e**c*hs *t*datsilgig tvldqaetag arlvvlatat ppgsvtvphp nieevalstt geipfygkai plevikggrh lif*c*hskkkc *d*elaaklval ginavayyrg ldvsviptsg dvvvvatdal mtgytgdfds vid*c*nt*c*vtq tvdfsldptf tietitlpqd avsrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 107) |
| D | Y241S | avdfipven lettmrspvf tdnssppvvp gsfqvahlha ptgsgkstkv paayaaqgyk vlvlnpsvaa tlgfgaSmsk ahgidpnirt gvrtittgsp itystygkfl ad*ggcsggay* diii*c*d*e**c*hs *t*datsilgig tvldqaetag arlvvlatat ppgsvtvphp nieevalstt geipfygkai plevikggrh lif*c*hskkkc *d*elaaklval ginavayyrg ldvsviptsg dvvvvatdal mtgytgdfds vid*c*nt*c*vtq tvdfsldptf tietitlpqd aysrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 108) |
| E | D290N | avdfipven lettmrspvf tdnssppvvp qsfqvahlha ptgsgkstkv paayaaqgyk vlvlnpsvaa tlgfgaymsk ahgidpnirt gvrtittgsp itystygkfl ad*ggcsggay* diii*c*Ne**c*hs *t*datsilgig tvldqaetag arlvvlatat ppgsvtvphp nieevalstt geipfygkai plevikggrh lif*c*hskkkc *d*elaaklval ginavayyrg ldvsviptsg dvvvvatdal mtgytgdfds vid*c*nt*c*vtq tvdfsldptf tietitlpqd avsrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 109) |
| F | E291Q | avdfipven lettmrspvf tdnssppvvp qsfqvahlha ptgsgkstkv paayaaqgyk vlvlnpsvaa tlgfgaymsk ahgidpnirt gvrtittgsp itystygkfl ad*ggcsggay* diii*c*dQ*c*hs *t*datsilgig tvldqaetag arlvvlatat ppgsvtvphp nieevalstt geipfygkai plevikggrh lif*c*hskkkc *d*elaaklval ginavayyrg ldvsviptsg dvvvvatdal mtgytgdfds vid*c*nt*c*vtq tvdfsldptf tietitlpqd avsrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 110) |
| G | H293A | avdfipven lettmrspvf tdnssppvvp qsfqvahlha ptgsgkstkv paayaaqgyk vlvlnpsvaa tlgfgaymsk ahgidpnirt gvrtittgsp itystygkfl ad*ggcsggay* diii*c*d*e*cAs *t*datsilgig tvldqaetag arlvvlatat ppgsvtvphp nieevalstt geipfygkai plevikggrh lif*c*hskkkc *d*elaaklval ginavayyrg ldvsviptsg dvvvvatdal mtgytgdfds vid*c*nt*c*vtq tvdfsldptf tietitlpqd avsrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 111) |
| H | T419G | avdfipven lettmrspvf tdnssppvvp gsfqvahlha ptgsgkstkv paayaaqgyk vlvlnpsvaa tlgfgaymsk ahgidpnirt gvrtittgsp itystygkfl ad*ggcsggay* diii*c*d*e**c*hs *t*datsilgig tvldqaetag arlvvlatat ppgsvtvphp nieevalstt geipfygkai plevikggrh lif*c*hskkkc *d*elaaklval ginavayyrg ldvsviptsg dvvvvatdal mtgyGgdfds vid*c*nt*c*vtq tvdfsldptf tietitlpqd avsrtqrrgr tgrgkpgiyr fvapgerpsg mfdssvlcec ydagcawyel tpaettvrlr aymntpglpv cqdhlefweg |

TABLE 1-continued

| Antigen designation | Antigen | Sequence |
|---|---|---|
| | | vftglthida hflsqtkqsg enlpylvayq atvcaraqap ppswdqmwkc lirlkptlhg ptpllyrlga vgneitlthp vtkyimtcms adlevvt (SEQ ID NO: 112) |
| I | Q460H | avdfipven lettmrspvf tdnssppvvp gsfqvahlha ptgsgkstkv paayaaggyk vlvlnpsvaa tlgfgaymsk ahgidpnirt gvrtittgsp itystygkfl adggCsggay diiicdeChs *t*datsilgig tvldqaetag arlvvlatat ppgsvtvphp nieevalstt geipfygkai plevikggrh lifch*skkk*c *d*elaaklval ginavayyrg ldvsviptsg dvvvvatdal mtgytgdfds vidcntcvtq tvdfsldptf tietitlpqd avsrtHrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vgneitlthp vtkyimtc**ms adlevvt (SEQ ID NO: 113) |
| J | R464A | avdfipven lettmrspvf tdnssppvvp gsfqvahlha ptgsgkstkv paayaaggyk vlvlnpsvaa tlgfgaymsk ahgidpnirt gvrtittgsp itystygkfl adggCsggay diiicdeChs *t*datsilgig tvldqaetag arlvvlatat ppgsvtvphp nieevalstt geipfygkai plevikggrh lifch*skkk*c *d*elaaklval ginavayyrg ldvsviptsg dvvvvatdal mtgytgdfds vidcntcvtq tvdfsldptf tietitlpqd avsrtqrrgA tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vgneitlthp vtkyimtc**ms adlevvt (SEQ ID NO: 114) |
| K | R467K | avdfipven lettmrspvf tdnssppvvp gsfqvahlha ptgsgkstkv paayaaggyk vlvlnpsvaa tlgfgaymsk ahgidpnirt gvrtittgsp itystygkfl adggCsggay diiicdeChs *t*datsilgig tvldqaetag arlvvlatat ppgsvtvphp nieevalstt geipfygkai plevikggrh lifch*skkk*c *d*elaaklval ginavayyrg ldvsviptsg dvvvvatdal mtgytgdfds vidcntcvtq tvdfsldptf tietitlpqd avsrtqrrgr tgKgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vgneitlthp vtkyimtc**ms adlevvt (SEQ ID NO: 115) |
| L | W501A | avdfipven lettmrspvf tdnssppvvp qsfqvahlha ptgsgkstkv paayaaggyk vlvlnpsvaa tlgfgaymsk ahgidpnirt gvrtittgsp itystygkfl adggCsggay diiicdeChs *t*datsilgig tvldqaetag arlvvlatat ppgsvtvphp nieevalstt geipfygkai plevikggrh lifch*skkk*c *d*elaaklval ginavayyrg ldvsviptsg dvvvvatdal mtgytgdfds vidcntcvtq tvdfsldptf tietitlpqd avsrtqrrgr tgrgkpgiyr fvapgerpsg mfdssvlcec ydagcaAyel tpaettvrlr aymntpglpv cqdhlefweg vftglthida hflsqtkqsg enlpylvayq atvcaraqap ppswdqmwkc lirlkptlhg ptpllyrlga vgneitlthp vtkyimtc**ms adlevvt (SEQ ID NO: 116) |
| M | | Any combination of two mutations selected from the group consisting of K210N, S211A, T212E, Y241S, D290N, E291Q, H293A, T419G, Q460H, R464A, R467K and W501A |
| N | | Any combination of three mutations selected from the group consisting of K210N, S211A, T212E, Y241S, D290N, E291Q, H293A, T419G, Q460H, R464A, R467K and W501A |
| O | | Any combination of four mutations selected from the group consisting of K210N, S211A, T212E, Y241S, D290N, E291Q, H293A, T419G, Q460H, R464A, R467K and W501A |
| P | | Any combination of five mutations selected from the group consisting of K210N, S211A, T212E, Y241S, D290N, E291Q, H293A, T419G, Q460H, R464A, R467K and W501A |
| Q | | Any combination of six mutations selected from the group consisting of K210N, S211A, T212E, Y241S, D290N, E291Q, H293A, T419G, Q460H, R464A, R467K and W501A |

TABLE 1-continued

| Antigen designation | Antigen Sequence |
|---|---|
| R | Any combination of seven mutations selected from the group consisting of K210N, S211A, T212E, Y241S, D290N, E291Q, H293A, T419G, Q460H, R464A, R467K and W501A |
| S | Any combination of eight mutations selected from the group consisting of K210N, S211A, T212E, Y241S, D290N, E291Q, H293A, T419G, Q460H, R464A, R467K and W501A |
| T | Any combination of nine mutations selected from the group consisting of K210N, S211A, T212E, Y241S, D290N, E291Q, H293A, T419G, Q460H, R464A, R467K and W501A |
| U | Any combination of ten mutations selected from the group consisting of K210N, S211A, T212E, Y241S, D290N, E291Q, H293A, T419G, Q460H, R464A, R467K and W501A |
| V | Any combination of eleven mutations selected from the group consisting of K210N, S211A, T212E, Y241S, D290N, E291Q, H293A, T419G, Q460H, R464A, R467K and W501A |
| W | Any combination of twelve mutations selected from the group consisting of K210N, S211A, T212E, Y241S, D290N, E291Q, H293A, T419G, Q460H, R464A, R467K and W501A |
| X | avdfipven lettmrspvf tdnssppvvp qsfqvahlha ptgsgkstkv paayaaqgyk vlvlnpsvaa tlgfgaymsk ahgidpnirt gvrtittgsp itystygkfl adgg*c*sgg*a*y diii*cde*C*hs *t*datsilgig tvldqaetag arlvvlatat ppgsvtvphp nieevalstt geipfygkai plevikggrh lif*c*hskkk*c* delaaklval ginavayyrg ldvsviptsg dvvvvatdal mtgytgdfds vid*cnt*c*vtq tvdfsldptf tietitltlpqd aysrtqrrgr tgrgkpgiyr fvapgerpsg mfdssvl*cec* ydagSawyel tpaettvrlr aymntpglpv *c*qdhlefweg vftglthida hflsqtkqsg enlpylvayq atv*c*araqap ppswdqmwk*c* lirlkptlhg ptpllyrlga vqneitlthp vtkyimtcms adlevvt (SEQ ID NO: 117) |
| Y | avdfipven lettmrspvf tdnssppvvp qsfqvahlha ptgsgkstkv paayaaqgyk vlvlnpsvaa tlgfgaymsk ahgidpnirt gvrtittgsp itystygkfl adgg*c*sgg*a*y diii*cde*C*hs *t*datsilgig tvldqaetag arlvvlatat ppgsvtvphp nieevalstt geipfygkai plevikggrh lif*c*hskkk*c* delaaklval ginavayyrg ldvsviptsg dvvvvatdal mtgytgdfds vid*cnt*c*vtq tvdfsldptf tietitltlpqd avsrtqrrgr tgrgkpgiyr fvapgerpsg mfdssvl*cec* ydagcawyel tpaettvrlr aymntpglpv Sqdhlefweg vftglthida hflsqtkqsg enlpylvayq atv*c*araqap ppswdqmwk*c* lirlkptlhg ptpllyrlga vqneitlthp vtkyimtcms adlevvt (SEQ ID NO: 118) |
| Z | avdfipven lettmrspvf tdnssppvvp qsfqvahlha ptgsgkstkv paayaaqgyk vlvlnpsvaa tlgfgaymsk ahgidpnirt gvrtittgsp itystygkfl adgg*c*sgg*a*y diii*cde*S*hs *t*datsilgig tvldqaetag arlvvlatat ppgsvtvphp nieevalstt geipfygkai plevikggrh lif*c*hskkk*c* delaaklval ginavayyrg ldvsviptsg dvvvvatdal mtgytgdfds vid*cnt*c*vtq tvdfsldptf tietitltlpqd avsrtqrrgr tgrgkpgiyr fvapgerpsg mfdssvl*cec* ydagcawyel tpaettvrlr aymntpglpv cqdhlefweg vftglthida hflsqtkqsg enlpylvayq atv*c*araqap ppswdqmwk*c* lirlkptlhg ptpllyrlga vqneitlthp vtkyimtcms adlevvt (SEQ ID NO: 119) |
| A1 | avdfipven lettmrspvf tdnssppvvp qsfqvahlha ptgsgkstkv paayaaqgyk vlvlnpsvaa tlgfgaymsk ahgidpnirt gvrtittgsp itystygkfl adgg*c*sgg*a*y diii*cde*C*hs *t*datsilgig tvldqaetag arlvvlatat ppgsvtvphp nieevalstt geipfygkai plevikggrh lifShskkk*c* delaaklval ginavayyrg ldvsviptsg dvvvvatdal mtgytgdfds vid*cnt*c*vtq tvdfsldptf tietitltlpqd aysrtqrrgr tgrgkpgiyr fvapgerpsg mfdssvl*cec* ydagcawyel tpaettvrlr aymntpglpv cqdhlefweg vftglthida hflsqtkqsg enlpylvayq atv*c*araqap ppswdqmwk*c* lirlkptlhg ptpllyrlga vqneitlthp vtkyimtcms adlevvt (SEQ ID NO: 120) |
| A2 | avdfipven lettmrspvf tdnssppvvp qsfqvahlha ptgsgkstkv paayaaqgyk vlvlnpsvaa tlgfgaymsk ahgidpnirt gvrtittgsp itystygkfl adgg*c*sgg*a*y diii*cde*C*hs *t*datsilgig tvldqaetag arlvvlatat ppgsvtvphp nieevalstt geipfygkai plevikggrh lif*c*hskkkS delaaklval ginavayyrg ldvsviptsg dvvvvatdal mtgytgdfds vid*cnt*c*vtq tvdfsldptf tietitltlpqd aysrtqrrgr tgrgkpgiyr fvapgerpsg mfdssvl*cec* ydagcawyel tpaettvrlr aymntpglpv cqdhlefweg vftglthida hflsqtkqsg enlpylvayq atv*c*araqap ppswdqmwk*c* lirlkptlhg ptpllyrlga vqneitlthp vtkyimtcms adlevvt (SEQ ID NO: 121) |

TABLE 1-continued

Antigen
designation | Antigen Sequence
---|---
A3 | Any combination of mutations of any of A-W in combination with one, two, three, four or five of the mutations shown in X, Y, Z, A1, and A2.

Production of HCV NS3 Antigens

The NS3 antigen molecules of the present invention are generally produced recombinantly. The recombinant production of various HCV antigens has been described. See, e.g., Houghton et al., U.S. Pat. No. 5,350,671; Chien et al., J. Gastroent. Hepatol. (1993) 8:S33-39; Chien et al., International Publication No. WO 93/00365; Chien, D. Y., International Publication No. WO 94/01778. Given that the present invention describes specific NS3 antigens for use in HCV detection assays and given that techniques for recombinant production of HCV antigens are known to those of skill in the art, such techniques may now be used to advantageously produce antigens for improved immunoassays.

Simply by way of providing a general description for such recombinant production, the skilled person would understand that polynucleotides encoding NS3 HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) Nature 292:756; Nambair et al. (1984) Science 223:1299; and Jay et al. (1984) J. Biol. Chem. 259:6311.

Thus, particular nucleotide sequences can be obtained from vectors harboring the desired sequences (including the mutations that are described herein) or synthesized completely or in part using various oligonucleotide synthesis techniques known in the art, such as site-directed mutagenesis and polymerase chain reaction (PCR) techniques where appropriate. See, e.g., Sambrook, supra; see also, Jayaraman et al. (1991) Proc. Natl. Acad. Sci. USA 88:4084-4088. Additionally, oligonucleotide directed synthesis (Jones et al. (1986) Nature 54:75-82), oligonucleotide directed mutagenesis of pre-existing nucleotide regions (Riechmann et al. (1988) Nature 332:323-327 and Verhoeyen et al. (1988) Science 239:1534-1536), and enzymatic filling-in of gapped oligonucleotides using T4 DNA polymerase (Queen et al. (1989) Proc. Natl. Acad. Sci. USA 86:10029-10033) can be used under the invention to provide molecules having altered or enhanced antibody-binding capabilities, and/or reduced immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) EMBO J. 4:761), the enhancer/promoter derived from the long terminal repeat (LTR) of the Rous Sarcoma Virus (Gorman et al. (1982) Proc. Natl. Acad. Sci. USA 79:6777) and elements derived from human CMV (Boshart et al. (1985) Cell 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

The molecules can be expressed in a wide variety of systems, including insect, mammalian, bacterial, viral and yeast expression systems, all well known in the art.

For example, insect cell expression systems, such as baculovirus systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., Yeast Genetic Engineering (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences that encode the NS3 antigens of the present invention can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

Immunodiagnostic Reagents

In particular embodiments, the NS3 antigens described above are contemplated for use as immunodiagnostic reagents. It is shown herein that the antigens of the present invention have increased stability, and increased immunoreactivity with NS3 antibodies as compared to C33 antigen. Immunodiagnostic reagents of the invention will be comprised of the above-described antigen polypeptides comprising an epitope that is immunoreactive with an antibody that specifically binds to the NS3 region of HCV either alone or in combination with other isolated or purified polypeptides comprising one or more epitopes that is immunoreactive with an antibody that specifically binds to another portion of HCV including but not limited to the NS3 region of HCV, the core antigen of HCV, the NS4 region of HCV or combinations thereof. The polypeptides of which the immunodiagnostic reagent is comprised can be, but need not necessarily be, coated on a solid support such as for example, a microparticle, (e.g., magnetic particle), bead, test tube, microtiter plate, cuvette, membrane, scaffolding molecule, film, filter paper, disc or chip. In this regard, where the immunodiagnostic reagent comprises the NS3 antigens of the present invention in combination with additional antigens, the antigens of the present invention and the additional antigens can be co-coated on the same solid support or can be on separate solid supports (the terms "solid support" and "solid phase" are used interchangeably herein). When the antigens are co-coated on the same solid support, preferably the NS3 antigens of the present invention and the additional antigens are co-coated in a ratio of about 1:2 to about 1:6, wherein, when the NS3 antigens of the present invention and the additional antigens are co-coated on the same solid support in a ratio of about 1:2, the concentration of the NS3 antigens of the present invention is at least about 40 µg/mL and the concentration of the additional antigens is at least about 80 µg/mL.

Notably, the immunodiagnostic reagent will include the antigens of the invention labeled with a detectable label or labeled with a specific partner that allows capture or detection. For example, the labels may be a detectable label, such as a fluorophore, radioactive moiety, enzyme, biotin/avidin label, chromophore, chemiluminescent label, or the like. Such labels are described in further detail infra.

Kits

Still further provided is a kit comprising an immunodiagnostic reagent comprising an antigen of the present invention and instructions for the use of the immunodiagnostic reagent in an immunoassay for the detection of anti-HCV antibodies. For example, the kit can comprise instructions for assaying the test sample for anti-HCV antibody by immunoassay. While preferred embodiments employ chemiluminescent microparticle immunoassays for assaying the test sample, it should be understood that the antigens of the present invention may be used in any other immunoassay known to those of skill in the art for determining the presence of HCV antibodies in a test sample. The instructions can be in paper form or computer-readable form, such as a disk, CD, DVD, or the like. Alternatively or additionally, the kit can comprise a calibrator or control, e.g., purified, and optionally lyophilized, anti-HCV antibody, and/or at least one container (e.g., tube, microtiter plates or strips, which can be already coated with an immunodiagnostic reagent) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying anti-HCV antibody.

Any antibodies, which are provided in the kit, such as anti-IgG antibodies and anti-IgM antibodies, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. It should be understood that in the immunodiagnostic reagent the NS3 antigens of the invention may be detectably labeled, the additional antigens also may be detectably labeled and any antibodies provided in kit for use along with such reagents also may be detectably labeled.

If desired, the kit can contain a solid support phase, such as a magnetic particle, bead, test tube, microtiter plate, cuvette, membrane, scaffolding molecule, film, filter paper, disc or chip.

Method of Determining the Presence, Amount or Concentration of Anti-HCV Antibodies in a Test Sample The present disclosure provides a method for determining the presence, amount or concentration of anti-HCV antibodies in a test sample. Any suitable assay known in the art can be used in such a method as long as such an assay uses one or more of the NS3 antigens of the present invention. Examples include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc.

In specific embodiment of the immunoassays, the recombinant NS3 antigens may be used as capture reagents (e.g., by using reagents in which the amino—or carboxy-terminal of the antigen comprises a biotin tag) or as a detection (conjugate) reagents in which the antigens of the invention are either directly or indirectly detectably labeled, e,g, with acridinium. Indirect labeling requires the use of for example, acridinylated BSA (or similar detectable moiety) covalently coupled to the free thiol of unpaired cysteine residues within the NS3 protein via SMCC-type linker. To facilitate such indirect labeling certain of the antigens of the present invention have been further modified to include additional cysteine residues at the C-terminus. In additional embodiments, the inventors have found that inclusion of two cysteine residues at the C-terminus of the helicase antigen can facilitate direct labeling of the antigen.

Typically, immunoassays are performed in 1-step or 2-step format. Solid phase reagents for capture of immune complexes formed in solution in the 1-step assay include anti-biotin monoclonal antibody, streptavidin or neutravidin or other biotin binding moeities.

In a SELDI-based immunoassay, a capture reagent that specifically binds anti-HCV-antibody is attached to the surface of a mass spectrometry probe, such as a pre-activated protein chip array. The anti-HCV antibody is then specifically captured on the biochip (in the present invention, such capture may be accomplished using one or more of the antigens of the present invention), and the captured anti-HCV antibody is detected by mass spectrometry. Alternatively, the anti-HCV antibody can be eluted from the capture reagent and detected by traditional MALDI (matrix-assisted laser desorption/ionization) or by SELDI.

A chemiluminescent microparticle immunoassay, in particular one employing the ARCHITECT® automated analyzer (Abbott Laboratories, Abbott Park, Ill.), is an example of a preferred immunoassay in which the antigens of the present invention may readily be employed. An agglutination assay, such as a passive hemagglutination assay, also can be used. In an agglutination assay an antigen-antibody reaction is detected by agglutination or clumping. In a passive hemagglutination assay, erythrocytes are coated with the antigen and the coated erythrocytes are used in the agglutination assay.

Methods well-known in the art for collecting, handling and processing urine, blood, serum and plasma, and other body fluids, are used in the practice of the present disclosure, for instance, when the polypeptides according to the present disclosure are employed as immunodiagnostic reagents and/or in an anti-HCV antibody immunoassay kit. The test sample can comprise further moieties in addition to the polypeptide of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform).

The pretreatment reagent can be any reagent appropriate for use with the immunoassay and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a pretreatment reagent the assay is rendered more sensitive by disruption of preformed/preexisting immune complexes or viral particles in the test sample. Such a pretreatment step comprises removing any interfering analyte binding protein by addition of the pretreatment agent to the test sample. In such an assay, the supernatant of the mixture absent any binding protein is used in the assay, proceeding directly to the antibody capture step.

In some other embodiments, use of the pretreatment does not require such a separation step. The entire mixture of test sample and pretreatment reagent are contacted with a labeled specific binding partner for anti-HCV antibody, such as an antigen of the present invention that has been labeled. The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 methylene glycol) is still present (or remains) in the test sample mixture during capture.

In a heterogeneous format, after the test sample is obtained from a subject, a first mixture is prepared. The mixture contains the test sample being assessed for anti-HCV antibodies and a first specific binding partner, wherein the first specific binding partner and any anti-HCV antibodies contained in the test sample form a first specific binding partner-anti-HCV antibody complex. Preferably, the first specific binding partner is an NS3 antigen of the present invention, preferably any one or more of the antigens shown in Table 1 and in the Examples herein above.

The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

After the mixture containing the first specific binding partner-anti-HCV antibody complex is formed, any unbound anti-HCV antibody is removed from the complex using any technique known in the art. For example, the unbound anti-HCV antibody can be removed by washing. Desirably, however, the first specific binding partner is present in excess of any anti-HCV antibody present in the test sample, such that all anti-HCV antibody that is present in the test sample is bound by the first specific binding partner.

After any unbound anti-HCV antibody is removed, a second specific binding partner is added to the mixture to form a first specific binding partner-anti-HCV antibody-second specific binding partner complex. The second specific binding partner is preferably a combination of an anti-IgG antibody and an anti-IgM antibody. Moreover, also preferably, the second specific binding partner is labeled with or contains a detectable label as described above.

Any suitable detectable label as is known in the art can be used. For example, the detectable label can be a radioactive label (such as $^{3}H$, $^{125}I$, $^{35}S$, $^{14}C$, $^{32}P$, and $^{33}P$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2.sup.nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-anti-HCV antibody complexes form. Alternatively, if a second specific binding partner is used and the second specific binding partner is detectably labeled with an acridinium compound, detectably labeled first specific binding partner-anti-HCV antibody-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of anti-HCV antibody is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of anti-HCV antibody in the sample can be quantified. Specifically, the amount of anti-HCV antibody in the sample is proportional to the intensity of the signal generated. The amount of anti-HCV antibody present can be quantified by comparing the amount of light generated to a standard curve for anti-HCV antibody or by comparison to a reference standard. The standard curve can be generated using serial dilutions or solutions of known concentrations of anti-HCV antibody by mass spectroscopy, gravimetric methods, and other techniques known in the art.

Anti-HCV antibody immunoassays can be conducted using any suitable format known in the art. Generally speaking, a sample being tested for (for example, suspected of containing) anti-HCV antibodies can be contacted with a capture antigen and at least one detection antibody (which can be a second detection antibody or a third detection antibody), such as labeled anti-IgG and anti-IgM antibodies, either simultaneously or sequentially and in any order. For example, the test sample can be first contacted with at least one capture antigen and then (sequentially) with at least one detection antibody. Alternatively, the test sample can be first contacted with at least one detection antibody and then (sequentially) with at least one capture antibody. In yet another alternative, the test sample can be contacted simultaneously with a capture antigen and a detection antibody.

In the sandwich assay format, a sample suspected of containing anti-HCV antibodies (or a fragment thereof) is first brought into contact with an at least one first capture antigen under conditions that allow the formation of a first capture antigen/anti-HCV antibody complex. If more than one capture antigen is used, multiple first capture antigen/anti-HCV antibody complexes are formed. In a sandwich assay, the antigen(s), preferably, the at least one capture antigen, is/are used in molar excess amounts of the maximum amount of anti-HCV antibodies expected in the test sample. For example, from about 5 µg to about 1 mg of antigen per mL of buffer (e.g., microparticle coating buffer) can be used.

Competitive inhibition immunoassays, which are often used to measure small analytes, comprise sequential and classic formats. In a sequential competitive inhibition immunoassay a capture antigen (i.e., a polypeptide, and preferably a pair of polypeptides, as described herein) to an antibody of interest (i.e., an anti-HCV antibody) is coated onto a well of a microtiter plate. When the sample containing the antibody of interest is added to the well, the antibody of interest binds to the capture antigen. After washing, a known amount of labeled (e.g., biotin or horseradish peroxidase (HRP)) antibody is added to the well. A substrate for an enzymatic label is necessary to generate a signal. An example of a suitable substrate for HRP is 3,3',5,5'-tetramethylbenzidine (TMB). After washing, the signal generated by the labeled antibody is measured and is inversely proportional to the amount of antibody in the sample. In a classic competitive inhibition immunoassay antigen for an antibody of interest is coated onto a well of a microtiter plate. However, unlike the sequential competitive inhibition immunoassay, the sample containing the antibody of interest (i.e., an anti-HCV antibody) and the labeled antibody are added to the well at the same. Any antibody in the sample competes with labeled antibody for binding to the capture antigen. After washing, the signal generated by the labeled analyte is measured and is inversely proportional to the amount of analyte in the sample.

Optionally, prior to contacting the test sample with the at least one capture antigen (for example, the first capture antigen), the at least one capture antigen can be bound to a solid support, which facilitates the separation of the first antigen/anti-HCV antibody complex from the test sample. The substrate to which the capture antigen is bound can be any suitable solid support or solid phase that facilitates separation of the capture antigen-anti-HCV antibody complex from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen to the substrate results; alternatively, a chemical coupling agent or other means can be used to bind covalently the antigen to the substrate, provided that such binding does not interfere with the ability of the antigen to bind to anti-HCV antibodies.

Alternatively, the anti-HCV antibody from the test sample can be bound with microparticles, which have been previously coated with antigen. If desired, one or more capture reagents, such as a pair of polypeptides as described herein, each of which can be bound by an anti-HCV antibody, can be attached to solid phases in different physical or addressable locations (e.g., such as in a biochip configuration (see, e.g., U.S. Pat. No. 6,225,047, Intl Pat. App. Pub. No. WO 99/51773; U.S. Pat. No. 6,329,209; Intl Pat. App. Pub. No. WO 00/56934, and U.S. Pat. No. 5,242,828). If the capture reagent is attached to a mass spectrometry probe as the solid support, the amount of anti-HCV antibodies bound to the probe can be detected by laser desorption ionization mass spectrometry. Alternatively, a single column can be packed with different beads, which are derivatized with the one or more capture reagents, thereby capturing the anti-HCV antibody in a single place (see, antibody derivatized, bead-based technologies, e.g., the xMAP technology of Luminex (Austin, Tex.)).

After the test sample being assayed for anti-HCV antibodies is brought into contact with at least one capture antigen (for example, the first capture antigen), the mixture is incubated in order to allow for the formation of a first antigen (or multiple antigen)-anti-HCV antibody (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antigen/anti-HCV antibody complex, the complex is then contacted with at least one detection antibody (under conditions which allow for the formation of a (first or multiple) capture antigen/anti-HCV antibody/second antibody detection complex). The at least one detection antibody can be the second, third, fourth, etc. antibodies used in the immunoassay. If the capture antigen/anti-HCV antibody complex is contacted with more than one detection antibody, then a (first or multiple) capture antigen/anti-HCV antibody/(multiple) detection antibody complex is formed. As with the capture antigen (e.g., the first capture antigen), when the at least second (and subsequent) detection antibody is brought into contact with the capture antigen/anti-HCV antibody complex, a period of incubation under conditions similar to those described above is required for the formation of the (first or multiple) capture antigen/anti-HCV antibody/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antigen/anti-HCV antibody/(second or multiple) detection antibody complex. Any detectable label known in the art can be used (see discussion above, including Polak and Van Noorden (1997) and Haugland (1996)).

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The (first or multiple) capture antigen/anti-HCV antibody/(second or multiple) detection antibody complex can be, but does not have to be, separated from the remainder of the test sample prior to quantification of the label. For example, if the at least one capture antigen (e.g., the first capture antigen) is bound to a solid support, such as a well or a bead, separation can be accomplished by removing the fluid (of the test sample) from contact with the solid support. Alternatively, if the at least first capture antigen is bound to a solid support, it can be simultaneously contacted with the anti-HCV antibody-containing sample and the at least one second detection antibody to form a first (multiple) antigen/anti-HCV antibody/second (multiple) antibody complex, followed by removal of the fluid (test sample) from contact with the solid support. If the at least one first capture antigen is not bound to a solid support, then the (first or multiple)

capture antigen/anti-HCV antibody/(second or multiple) detection antibody complex does not have to be removed from the test sample for quantification of the amount of the label.

After formation of the labeled capture antigen/anti-HCV antibody/detection antibody complex (e.g., the first capture antigen/anti-HCV antibody/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of anti-HCV antibody in the test sample is determined by use of a standard curve that has been generated using serial dilutions of anti-HCV antibody of known concentration. Other than using serial dilutions of anti-HCV antibodies, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

Commercially available anti-HCV antibodies as well as anti-IgG and anti-IgM antibodies can be used in the methods of assay and kits thereof. Commercially available antibodies include those available from Abnova (Walnut, Calif., and Taiwan) and GenWay Biotech, Inc. (San Diego, Calif.). See, also, European Pat. App. EP2099825 A2 regarding the preparation of anti-HCV antibodies.

Any suitable control composition can be used in the anti-HCV antibody immunoassays. The control composition generally comprises anti-HCV antibodies and any desirable additives.

Thus, in view of the above, a method of determining the presence, amount, or concentration of anti-HCV antibodies in a test sample is provided. The method comprises assaying the test sample for anti-HCV antibodies by an assay:
  (i) employing an immunodiagnostic reagent comprising at least an isolated or purified polypeptide comprising a recombinant NS3 antigen of the present invention, and at least one detectable label, and comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies. The method can comprise the following steps:
    (i) contacting the test sample with the immunodiagnostic reagent comprising one of more recombinant NS3 antigens of the present invention so as to form first specific binding partner/anti-HCV antibody complex with HCV antibodies that may be present in the test sample,
    (ii) contacting the first specific binding partner/anti-HCV antibody complexes with at least one detectably labeled second specific binding partner for anti-HCV antibody (e.g., anti-IgG antibody and anti-IgM antibody or polypeptides as described herein) so as to form first specific binding partner/anti-HCV antibody/second specific binding partner complexes, and
    (iii) determining the presence, amount or concentration of anti-HCV antibodies in the test sample by detecting or measuring the signal generated by the detectable label in the first specific binding partner/anti-HCV antibody/second specific binding partner complexes formed in (ii).

Alternatively, the method can comprise the following steps:
    (i) contacting the test sample with the immunodiagnostic reagent comprising one of more recombinant NS3 antigens of the present invention and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one detectably labeled second specific binding partner compete with each other to form first specific binding partner/anti-HCV antibody complexes and first specific binding partner/second specific binding partner complexes, respectively, and
    (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The recombinant NS3 antigens of which the immunodiagnostic reagent is comprised can be coated on microparticles. In this regard, the NS3 antigens of which the immunodiagnostic reagent is comprised can be co-coated on the same microparticles as additional HCV antigens. When the polypeptides of which the immunodiagnostic reagent is comprised are co-coated on the same microparticles (e.g., a microparticle suspension containing 4% solids (4% weight/volume microparticles or 4 gr microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified NS3 antigen of the present invention (e.g., those described in Table 1) is at least about 40 µg/mL and the concentration of the other isolated or purified polypeptide is at least about 80 µg/mL. If the test sample was obtained from a patient, the method may further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

Also, in view of the above, a method of determining the presence, amount, or concentration of anti-HCV antibodies in a test sample is provided. The method comprises assaying the test sample for anti-HCV antibodies by an assay:
(i) employing: an immunodiagnostic reagent comprising at least one NS3 antigen of the presented invention at least one detectable label, and
(ii) comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies. The method can comprise the following steps:
   (i) contacting the test sample with the immunodiagnostic reagent comprising at least one recombinant NS3 antigen of the present invention so as to form first specific binding partner/anti-HCV antibody complexes,
   (ii) contacting the first specific binding partner/anti-HCV antibody complexes with at least one detectably labeled second specific binding partner for anti-HCV antibody (e.g., anti-IgG antibody and anti-IgM antibody or polypeptides as described herein) so as to form first specific binding partner/anti-HCV antibody/second specific binding partner complexes, and
   (iii) determining the presence, amount or concentration of anti-HCV antibodies in the test sample by detecting or measuring the signal generated by the detectable label in the first specific binding partner/anti-HCV antibody/second specific binding partner complexes formed in (ii). Alternatively, the method can comprise the following steps:
   (i) contacting the test sample with the immunodiagnostic reagent comprising at least one recombinant NS3 antigen of the present invention and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one second specific binding partner compete with each other to form first specific binding partner/anti-HCV antibody complexes and a first specific binding partner/second specific binding partner complexes, respectively, and
   (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The polypeptides of which the immunodiagnostic reagent is comprised can be coated on microparticles. In this regard, the polypeptides of which the immunodiagnostic reagent is comprised can be co-coated on the same microparticles. When the polypeptides of which the immunodiagnostic reagent is comprised are co-coated on the same microparticles (e.g., a microparticle suspension containing 4% solids (4% weight/volume microparticles or 4 gr microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified polypeptide comprising the recombinant NS3 antigen of the present invention is at least about 40 µg/mL and the concentration of the other isolated or purified polypeptide is at least about 80 µg/mL. If the test sample was obtained from a patient, the method can further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a test sample for anti-HCV antibodies. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., preeclampsia or cardiovascular disease) or with particular indicia can be made. Typically, the predetermined level is obtained with assays of reference subjects (or populations of subjects).

In particular, with respect to a predetermined level as employed for monitoring disease progression and/or treatment, the amount or concentration of anti-HCV antibodies may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for anti-HCV antibodies is defined in accordance with standard practice. Because the levels of anti-HCV antibodies in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable hepatitis, for example, and a "normal" (sometimes termed "control") patient or population is/are one(s) that exhibit(s) no detectable hepatitis, for example. Furthermore, given that anti-HCV antibodies are not routinely found at a high level in the majority of the human population, a "normal subject" can be considered an individual with no substantial detectable increased or elevated amount or concentration of anti-HCV antibodies, and a "normal" (sometimes termed "control") patient or population is/are one(s) that exhibit(s) no substantial detectable increased or elevated amount or concentration of anti-HCV antibodies. An "apparently normal subject" is one in which anti-HCV antibodies has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, hepatitis, for example, as defined herein.

Accordingly, the methods described herein also can be used to determine whether or not a subject has or is at risk of developing hepatitis. Specifically, such a method can comprise the steps of:

(a) determining the concentration or amount in a test sample from a subject of anti-HCV antibodies (e.g., using the methods described herein, or methods known in the art); and (b) comparing the concentration or amount of anti-HCV antibodies determined in step (a) with a predetermined level, wherein, if the concentration or amount of anti-HCV antibodies determined in step (a) is favorable with respect to a predetermined level, then the subject is determined not to have or be at risk for hepatitis. However, if the concentration or amount of anti-HCV antibodies determined in step (a) is unfavorable with respect to the predetermined level, then the subject is determined to have or be at risk for hepatitis.

Additionally, provided herein is method of monitoring the progression of disease in a subject. Optimally the method comprising the steps of:

(a) determining the concentration or amount in a test sample from a subject of anti-HCV antibodies;

(b) determining the concentration or amount in a later test sample from the subject of anti-HCV antibodies; and (c) comparing the concentration or amount of anti-HCV antibodies as determined in step (b) with the concentration or amount of anti-HCV antibodies determined in step (a), wherein if the concentration or amount determined in step (b) is unchanged or is unfavorable when compared to the concentration or amount of anti-HCV antibodies determined in step (a), then the disease in the subject is determined to have continued, progressed or worsened. By comparison, if the concentration or amount of anti-HCV antibodies as determined in step (b) is favorable when compared to the concentration or amount of anti-HCV antibodies as determined in step (a), then the disease in the subject is determined to have discontinued, regressed or improved Optionally, the method further comprises comparing the concentration or amount of anti-HCV antibodies as determined in step (b), for example, with a predetermined level. Further, optionally the method comprises treating the subject with one or more pharmaceutical compositions for a period of time if the comparison shows that the concentration or amount of anti-HCV antibodies as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of anti-HCV antibodies is determined (e.g., using the methods described herein or as known in the art). After the concentration or amount of anti-HCV antibodies is determined, optionally the concentration or amount of anti-HCV antibodies is then compared with a predetermined level. If the concentration or amount of anti-HCV antibodies as determined in the first test sample is lower than the predetermined level, then the subject is not treated with one or more pharmaceutical compositions. However, if the concentration or amount of anti-HCV antibodies as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of anti-HCV antibodies is determined in the second or subsequent test sample is determined (e.g., using the methods described herein or as known in the art). The concentration or amount of anti-HCV antibodies as determined in each of the second and subsequent test samples is then compared with the concentration or amount of anti-HCV antibodies as determined in the first test sample (e.g., the test sample that was originally optionally compared to the predetermined level). If the concentration or amount of anti-HCV antibodies as determined in step (c) is favorable when compared to the concentration or amount of anti-HCV antibodies as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of anti-HCV antibodies as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's anti-HCV antibodies level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from hepatitis will benefit from treatment. In particular, the disclosure relates to HCV companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, hepatitis is a candidate for therapy. Generally, the subject is one who has experienced some symptom of hepatitis or who has actually been diagnosed as having, or being at risk for, hepatitis and/or who demonstrates an unfavorable concentration or amount of anti-HCV antibodies or a fragment thereof, as described herein.

The method optionally comprises an assay as described herein, where analyte is assessed before and following treatment of a subject with one or more pharmaceutical compositions (e.g., particularly with a pharmaceutical related to a mechanism of action involving HCV), with immunosuppressive therapy, or by immunoabsorption therapy, with anti-angiogenic therapy, or where analyte is assessed following such treatment and the concentration or the amount of analyte is compared against a predetermined level. An unfavorable concentration of amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

Adaptation of Kit and Method

The kit (or components thereof), as well as the method of determining the concentration of anti-HCV antibodies in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., antigen) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is exemplary. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing anti-HCV antibody is added to the holding chamber of the test cartridge and the cartridge is inserted into the I-STAT® reader. After the detection antibody has dissolved into the sample, a pump element within the cartridge forces the sample into a conduit containing the chip. Here it is oscillated to promote formation of the sandwich between the capture antigen, anti-HCV antibody, and the labeled detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of anti-HCV antibody in the sample by means of an embedded algorithm and factory-determined calibration curve.

The methods and kits as described herein encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, and U.S. patent application Ser. No. 12/650,241, improved signal generation may be obtained, e.g., in an I-STAT® cartridge format, using a nucleic acid sequence linked to the signal antibody as a signal amplifier.

EXAMPLES

Example 1

Cloning and Expression of HCV NS3 9NB49H

The nucleotide sequence (Seq ID 1) encoding amino acids 1192-1457 of HCV (Seq ID 2) was codon optimized for E. coli expression and cloned into a modified pET32a vector wherein the sequence encoding a thioredoxin fusion protein was eliminated, and replaced with Methionine (M). In addition, a carboxy-terminal hexahistidine tag (SEQ ID NO: 122) was included to facilitate purification via immobilized metal affinity chromatography (IMAC). E. coli BL21 (DE3) cells were transformed with purified plasmid DNA and transformants screened. The resulting plasmid was designated p9NB49H and the protein expressed therefrom was designated as 9NB49H.

Protein expression was achieved by culturing the p9NB49H-transformed E. coli BL21(DE3) cells in terrific broth (TB) medium. Cells were grown in shake flasks to an OD600 nm of 0.50 and then induced with 1 mM IPTG and grown at 25-37° C. for approximately three hours until an OD600 nm of approximately 3.5 was obtained. Cells were harvested by centrifugation, and suspended in lysis buffer (50 mM KPO4, 300 mM KCl, 5 mM Imidazole, pH 8.0) supplemented with protease inhibitors. The cell suspension was frozen and thawed, benzonase was added, and the cells were lysed by sonication on ice. The lysate was divided into soluble and insoluble fractions by centrifugation. SDS-PAGE revealed that the NS3 9NB49H protein was present in the soluble fraction. IMAC purification was performed on the lysate soluble fraction using the Native IMAC Buffer Kit and Profinity IMAC cartridge (BioRad) according to the manufacture's protocol. Buffer exchange of the purified protein into PBS was accomplished by a desalting column or by dialysis. All buffers used throughout the purification procedure contained 20 mM beta-mercaptoethanol (β-ME).

Example 2

Cloning and Expression of HCV NS3 Nbt-9NB49H

The nucleotide sequence encoding the NS3 9NB49H protein described in Example 1 was subcloned into a modified pET32a plasmid wherein the open reading frame encodes an amino-terminal biotinylation tag (MSGLNDIFEAQKIEWHE (SEQ ID NO: 96)) with a GSGSNSM-linker sequence (SEQ ID NO: 97) upstream of the NS3-encoding sequence followed by a carboxyl-terminal hexahistidine tag (SEQ ID NO: 122) followed by a stop codon. The resulting plasmid was designated pNbt-9NB49H. The biotinylation tag, described by Beckett et al. (Protein Science, 8(4):921-929, 1999) permits site-specific biotin incorporation via a biotin ligase enzyme encoded by the E. coli BirA gene. E. coli BL21 (DE3) cells were co-transformed with the pNbt-9NB49H expression plasmid and a second plasmid (pBirAcm) expressing the biotin ligase under control of an IPTG inducible promoter. Cells were grown in shake flasks at 37° C. in Terrific Broth with biotin added to 0.050 mM final concentration to an OD600 nm of 0.50 and then induced with 1 mM IPTG and grown at 25° C. overnight. Cells were then collected via centrifugation and resuspended in lysis buffer and sonicated to disrupt the cells. In some instances, to further ensure a high level of site-specific biotinylation, ATP and biotin were added to the lysed cells (3 mM and 0.25 mM final concentrations, respectively) and incubated at room temperature for 2 hours. Recombinant protein was then purified via IMAC as described in Example 1.

Example 3

Cloning and Expression of HCV NS3 9NB49H-Cbt

The nucleotide sequence encoding the NS3 9NB49H protein described in Example 1, was subcloned into a modified pET32a vector wherein the open reading frame encodes N-terminal methionine followed by NS3 followed by a GSGSG-linker (SEQ ID NO: 98) and a hexahistidine tag (SEQ ID NO: 122) followed by a GG- linker and the biotinylation tag (GLNDIFEAQKIEWHE (SEQ ID NO: 99)) and finally the stop codon. The resulting plasmid was designated p9NB49H-Cbt. Protein expression and biotinylation was performed as described in Examples 1 and 2.

Example 4

Cloning and Expression of HCV NS3 9NB49H-Cbt Mutants

The nucleotide sequence encoding 9NB49H-Cbt described in Example 3 was site-specifically mutated to substitute cysteine codons with serine codons. Positions mutated are described in the table below wherein codon (amino acid) number of the HCV polyprotein sequence is based on that described by Kuiken et al. (Hepatology, 2006, 44(5):1355-1361). Recombinant protein expression, purification, and biotinylation were performed as described in Examples 1 and 2.

TABLE 1

| Cysteine Position in HCV Polyprotein | Cysteine Position in NS3 | Cysteine number in 9NB49H | Plasmid designation | Expressed protein designation | Seq ID# (nucleotide, amino acid) |
|---|---|---|---|---|---|
| C1305 | C279 | C1 | p9NB49H-Cbt-C1S | 9NB49H-Cbt-C1S | 3, 4 |
| C1315 | C289 | C2 | p9NB49H-Cbt-C2S | 9NB49H-Cbt-C2S | 5, 6 |
| C1318 | C292 | C3 | p9NB49H-Cbt-C3S | 9NB49H-Cbt-C3S | 7, 8 |
| C1394 | C368 | C4 | p9NB49H-Cbt-C4S | 9NB49H-Cbt-C4S | 9, 10 |
| C1400 | C374 | C5 | p9NB49H-Cbt-C5S | 9NB49H-Cbt-C5S | 11, 12 |

TABLE 1-continued

| Cysteine Position in HCV Polyprotein | Cysteine Position in NS3 | Cysteine number in 9NB49H | Plasmid designation | Expressed protein designation | Seq ID# (nucleotide, amino acid) |
|---|---|---|---|---|---|
| C1305, C1315, C1318 | C279, C289, C292 | C1, C2, C3 | p9NB49H-Cbt-C1-3S | 9NB49H-Cbt-C1-3S | 13, 14 |
| C1394, C1400 | C368, C374 | C4, C5 | p9NB49H-Cbt-C4-5S | 9NB49H-Cbt-C4-5S | 15, 16 |
| C1305, C1315, C1318, C1394, C1400 | C279, C289, C292, C368, C374 | C1, C2, C3, C4, C5 | p9NB49H-Cbt-C1-5S | 9NB49H-Cbt-C1-5S | 17, 18 |

Example 5

Cloning and Expression of HCV NS3h and Variants Thereof

Recombinant HCV NS3 helicase variants were constructed by using the same amino terminus expressed by p9NB49H (i.e. amino acids 1192-1215 of the HCV polyprotein) fused to various regions of the HCV NS3 helicase as described in the table below and as shown in FIG. 1. Nucleotide sequences encoding the helicase constructs were cloned into a modified pET32a vector (minus thioredoxin fusion) with either a carboxyl-terminal GSGSG-hexahistidine tag (SEQ ID NO: 100) as described in Example 1 or a carboxyl-terminal GSGSG-hexahistidine-GG-biotinylation tag (SEQ ID NO: 101) as described in Example 2. Any construct containing the 3$^{rd}$ domain of the NS3 helicase comprises a carboxyl-terminal SGSGSG-hexahistidine tag (SEQ ID NO: 102), or a carboxyl-terminal SGSGSG-hexahistidine-GG-biotinylation tag (SEQ ID NO: 103). Protein expression with or without biotinylation and purification were performed as described in Examples 1 and 2.

TABLE 2

| Region of HCV Polyprotein | Region of HCV NS3 | Plasmid Designation | Expressed Protein Designation | Seq ID# (nucleotide, amino acid) |
|---|---|---|---|---|
| 1192-1657 | 166-631 | pNS3h(±Cbt) | NS3h (helicase) (±Cbt) | 19, 20 |
| 1192-1356 | 166-330 | pNS3-d1(±Cbt) | d1(±Cbt) | 21, 22 |
| 1192-1215 & 1357-1457 | 166-189 & 331-431 | pNS3-d2(±Cbt) | d2(±Cbt) | 23, 24 |
| 1192-1215 & 1512-1657 | 166-189 & 486-631 | pNS3-d3(±Cbt) | d3(±Cbt) | 25, 26 |
| 1192-1215 & 1357-1657 | 166-189 & 331-631 | pNS3-d2d3(±Cbt) | d2 + d3(±Cbt) | 27, 28 |
| 1192-1215 & 1357-1510 | 166-189 & 331-484 | pNS3-d2ext(±Cbt) | d2ext(±Cbt) | 29, 30 |
| 1192-1510 | 166-484 | pNS3-d1d2ext(±Cbt) | d1 + d2ext(±Cbt) | 31, 32 |
| 1192-1215 & 1458-1657 | 166-189 & 432-631 | pNS3-extd3(±Cbt) | extd3(±Cbt) | 33, 34 |

Example 6

Cloning and Expression of Full-length HCV NS3 Helicase Variants

The plasmid encoding the full-length NS3h (helicase) protein described in Example 5 (pNS3h-Cbt) was site-specifically mutagenized using standard methods to produce mutant clones wherein selected codons were replaced (i.e. substituted) as described in the table below.

TABLE 3

| Amino Acid of HCV Polyprotein | Amino Acid of HCV NS3 | NS3h mutant designation | Seq ID NO (nucleotide, amino acid) |
|---|---|---|---|
| K1236 | K210 | K46N | 35, 36 |
| S1237 | S211 | S47A | 37, 38 |
| T1238 | T212 | T48E | 39, 40 |
| Y1267 | Y241 | Y77S | 41, 42 |
| D1316 | D290 | D126N | 43, 44 |
| E1317 | E291 | E127Q | 45, 46 |
| C1318 | C292 | C3S | 47, 48 |
| H1319 | H293 | H129A | 49, 50 |
| C1400 | C374 | C5S | 51, 52 |
| T1445 | T419 | T255G | 53, 54 |
| Q1486 | Q460 | Q296H | 55, 56 |
| R1490 | R464 | R300A | 57, 58 |
| R1493 | R467 | R303K | 59, 60 |
| C1525 | C499 | C10S | 61, 62 |
| W1527 | W501 | W337A | 63, 64 |
| C1551 | C525 | C11S | 65, 66 |
| C1648 | C622 | C14S | 67, 68 |
| H1319 + R1490 | H293 + R464 | H129A + R300A | 69, 70 |
| C1318 + C1400 | C292 + C374 | C3S + C5S | 71, 72 |
| C1318 + C1525 | C292 + C499 | C3S + C10S | 73, 74 |
| C1318 + C1551 | C292 + C525 | C3S + C11S | 75, 76 |
| C1318 + C1648 | C292 + C622 | C3S + C14S | 77, 78 |
| P1256 + C1318 + C1400 | P230 + C292 + C374 | P66Q + C3S + C5S | 79, 80 |

The resulting constructs possessed a carboxyl-terminal SGSGSG-hexahistidine-GG-linker-biotinylation tag (SEQ ID NO: 103) as described in Example 5. Protein expression and biotinylation was performed by co-transformation of E. coli BL21 (DE3) cells with individual NS3 helicase-Cbt mutant plasmids and pBirAcm as described in Example 3. Purification was performed as described in Examples 1 and 2.

Example 7

Cloning and Expression of HCV NS3 Helicase Variants with Modified C-termini

The plasmid encoding the full-length NS3h (helicase) protein described in Example 5 (pNS3h) was modified downstream of the region encoding NS3h (HCV aa 1192-1657) to include sequences encoding in-frame a SGSGSG-linked octahistidine tag (SEQ ID NO: 104) followed by additional HCV NS3 helicase sequences as described in the table below, followed by a stop codon.

| Added HCV NS3 sequence | Numbering of added HCV polyprotein sequence | Plasmid Designation | Expressed Protein Designation | Seq ID# (nucleotide, amino acid) |
|---|---|---|---|---|
| GGCSGGA (SEQ ID NO: 82) | 1303-1309 | pNS3h-XC1 | NS3h-XC1 | 81, 82 |
| DECHSTD (SEQ ID NO: 84) | 1316-1322 | pNS3h-XC2 | NS3h-XC2 | 83, 84 |
| SKKKCDE (SEQ ID NO: 86) | 1396-1402 | pNS3h-XC3 | NS3h-XC3 | 85, 86 |

Protein expression was performed following transformation of *E. coli* BL21(DE3) cells with the individual modified NS3h plasmids (-XC1, -XC2, or -XC3) as described in Example 1. Protein purification of the C-terminally modified NS3h proteins was performed as described in Example 1.

Example 8

Fermentation, Protein Expression and Purification

The NS3 recombinant proteins (e.g. 9NB49H or NS3h or variants thereof) were expressed in *E. coli* BL21(DE3) cells cultured in 10L fermenters. An 120 mL seed culture grown in a shake flask containing Superbroth (SB) Media (rich media with glycerol as a carbon source) was used to inoculate a 10L fermenter containing SB media. Cells were grown at 37° C. until an optical density at 600 nm of 8-12 was reached. Protein expression was induced by adding isopropyl β-D-1-thiogalactopyranoside (IPTG) to a final concentration of 1 mM. The culture was then grown an additional 4 hours at 25-37° C. Cells were then harvested from the fermenter and then passed through a hollow fiber membrane filter to concentrate the harvest from the starting volume of 10L to 1-2 liters. The concentrated cells were then pelleted via centrifugation, the supernatant removed, and the resulting pellets were stored at −80° C. until used for protein purification.

In vivo biotinylation of recombinant HCV NS3 proteins containing either an amino-terminal or carboxyl-terminal biotinylation tag sequence (see Examples 2 and 3) was achieved by conducting fermentation as described above except that biotin was added to a final concentration of 0.05 mM at the time of induction. The culture was then grown an additional 4 hours at 25-37° C. and processed as described in the above paragraph.

Frozen *E. coli* cell pellets containing expressed soluble HCV NS3 recombinant antigens were thawed then resuspended in chilled lysis buffer (40 mM $NaPO_4$, 300 mM NaCl, 1.5 mM $MgCl_2$, 5% Glycerol, 5 mM beta-mercaptoethanol, pH 7.2) followed by lysis via continuous flow sonication at 0° C. for 45 minutes. After centrifugation to remove insoluble material, GE nickel sepharose Fast Flow resin was added to the supernatant and incubated overnight at 2-8° C. (shaking at 125 rpm). The resin containing bound antigen was then washed under mild vacuum with wash buffer (40 mM $NaPO_4$, pH 7.2, 500 mM NaCl, 1 mM EDTA, 20 mM imidizole, 5 mM beta-mercaptoethanol) and bound antigen was eluted using buffer containing 40 mM $NaPO_4$, 150 mM NaCl, 1 mM EDTA, 500 mM imidizole, 10 mM DTT, pH 7.2. The antigen was further purified via anion exchange chromatography as follows: antigen was bound to a GE Q HP anion exchange resin in 20 mM Tris pH 8.4, followed by gradient elution with 20 mM Tris, pH 8.4, 1 M NaCl, 5 mM EDTA. The eluted protein was then desalted using a GE Sephadex G25 column into final buffer containing 10 mM Phosphate, 150 mM NaCl, 5 mM EDTA, pH 7.2. The purified NS3 protein was stored at −70° C.

Example 9

Preparation of Acridinium-Bovine Serum Albumin (Acr-BSA)

A 30% solution (300 mg/mL) of bovine serum albumin (BSA) containing 0.1% sodium azide as preservative was purchased from a commercial source (Proliant Biologicals, Ankeny, Iowa). One milliliter (300 mg) of the 30% BSA solution was diluted with 2.0 mL of 0.1M PBS pH 8.0, transferred to a 0.5-3.0 mL Slide-A-Lyzer dialysis cassette (ThermoFisher, Waltham, Mass.) and dialyzed against 0.1M PBS pH 8.0 (2 exchanges, 600 mL/exchange) overnight at 2-8° C. The concentration of the dialyzed BSA solution was 97.1 mg/mL based on UV absorbance at 280 nm. Two hundred milligrams (2.060 mL, 3.0 umol, 1.0 mol equivalent) of the 97.1 mg/mL BSA solution was added to an amber glass vial containing 10.181 mL of 0.1M PBS pH 8.0. To this mixture was added 39 mg (1.092 mL, 45 umol, 15.0 mol equivalent) of SPSP-acridinium active ester in DMF [N,N-dimethylformamide. The reaction vial was capped; the solution was mixed by stirring at 350 rpm for 30 min, and then placed at room temperature overnight (20-26h). After incubation, free acridinium and aggregates were removed chromatographically (Sephacryl HR S-200 column, GE Healthsciences, Pa.) using 0.01M PBS/0.1% CHAPS pH 6.3 running buffer. Fractions corresponding to monomeric Acr-BSA conjugate were pooled and characterized by UV spectrophotometry (240-600 nm scan). Absorbance values at 280 nm and 370 nm were used to determine protein concentration and to calculate incorporation of acridinium per BSA molecule. The calculated protein concentration was 6.779 mg/mL with an average number of 6.2 acridiniums per BSA molecule.

Example 10

Preparation of Acridinium-BSA-9NB49H Conjugate

Preparation of Maleimide-Activated Acr-BSA. Acr-BSA (Example 8; 13.5 milligrams, 202 nmoles, 1.0 mol equivalent) 1.99 mL in PBS/0.1% CHAPS pH 6.3 was added to an amber glass vial and treated with 0.254 mL of 0.4M phosphate/8 mM EDTA/1.6% CHAPS pH 7.4 to adjust reaction pH to 7.4. To the homogeneous solution was added 0.040 mL (0.35 mg, 4.0 mole equivalents) of a fresh 0.02M aqueous solution of Succinimidyl 4-(N maleimidomethyl)-cyclohexane-1-carboxylate (Sulfo-SMCC, Pierce Chemical Co., Rockford, Ill.). The reaction vial was capped; the solution was stirred for 20 min without foaming and then allowed to incubate statically at room temperature for 60-90 minutes in the dark. The reaction mixture was desalted to remove unincorporated sulfo-SMCC by applying to a Zeba spin column (Pierce, Rockford, Ill.) pre-equilibrated with 0.1M PBS/0.1% CHAPS/5 mM EDTA pH 6.7. The absorbance of the eluted Acr-BSA-Mal reagent was measured at 280 and 370 nm to estimate protein concentration. The calculated protein concentration was 6.28 mg/mL. The Acr-BSA-Mal was used immediately in the conjugation of HCV NS3 antigen.

Conjugation of Recombinant 9NB49H to Acr-BSA-Mal. Acr-BSA-Mal (5.6 milligrams, 84 nmoles, 2.0 mole equivalents) in 0.789 mL of 0.1M PBS/0.1% CHAPS/5 mM EDTA pH 6.7 was added to a polypropylene tube. To this was added 1.2 mg (1.3 mL, 42 nmoles, 1.0 mol equivalent) of recombinant 9NB49H antigen in 0.01M PBS/5 mM EDTA pH 7.2. The solution was stirred for 30 min without foaming, and then allowed to incubate statically at room temperature overnight in dark. The conjugate was purified either at this stage or after carboxymethylation of 9NB49H free cysteines. In the case of carboxymethylation, the crude conjugate solution was treated with 0.270 mL of 0.5M phosphate buffer pH 11.0 to adjust pH to 8.0. The mixture was stirred for 5 min, then 0.94 mg (0.020 mL, 120 mole equivalents) of a fresh 0.25M iodoacetic (IAA) solution in 1N NaOH or 0.25M aqueous iodoacetaminde (IAM) was added under mixing to effect 9NB49H free Cys-carboxymethylation. The mixture was reacted statically at room temperature and dark for 60 min, and then passed thru a PD10 column equilibrated in 0.01M PBS/0.1% CHAPS/5 mM EDTA pH 6.3 (3.0 mL elution volume).

The Acr-BSA-9NB49H conjugate protein concentration was determined from the 280 nm absorbance of the conjugate after subtracting the 280 nm absorbance contributed by the Acr-BSA. The absorbance of a 1% (w/v) solution of 9NB49H of 0.52 was used to calculate the protein concentration. The 9NB49H concentration calculated as described was 0.406 mg/mL.

Example 11

Preparation of Acridinium-BSA-NS3h Conjugate

Preparation of (LC)Maleimide-Activated Acr-BSA. Acr-BSA (Example 8; 3.0 mg, 0.443 mL, 45 nmol, or 1.0 mol equivalent) in PBS/0.1% CHAPS pH 6.3 was added to an amber glass vial and treated with 0.058 ml of 0.4M phosphate/8 mM EDTA/1.6% CHAPS pH 7.4 buffer to adjust the reaction pH to 7.4. To the homogeneous solution was added 0.018 mL (0.080 mg, 180 nmoles, 4.0 mol equivalent) of a fresh 0.01M solution of Succinimidyl 4-(N-maleimidomethyl)cyclohexane-1-carboxy-(6-amidocaproate) (Lon Chain or LC-SMCC, Pierce Chemical Co., Rockford, Ill.) in dimethylsulfoxide (DMSO, Sigma Aldrich, St Louis, Mo.). The reaction vial was capped; the solution was stirred for 20 min without foaming and then allowed to incubate statically at room temperature for 60 minutes in dark. The reaction mixture was desalted to remove unincorporated LC-SMCC by applying to a Zeba spin column (Pierce, Rockford, Ill.) pre-equilibrated with 0.1M PBS/0.1% CHAPS/5 mM EDTA pH 6.7. The absorbance of the eluted Acr-BSA-Mal reagent was measured at 280 and 370 nm to estimate protein concentration. The calculated protein concentration was 5.25 mg/mL. The Acr-BSA-(LC)Mal was used immediately in the next conjugation step.

Conjugation of Recombinant NS3h to Acr-BSA-(LC)Mal. 1.20 mL (3.12 mg) of a 2.6 mg/mL solution of NS3h in 0.025M phosphate/0.25M NaCl/5 mM beta-mercaptoethanol/5 mM EDTA pH 8.0 was passed through a PD10 desalting column to remove the beta-mercaptoethanol. The NS3h protein was eluted with 2.5 mL of 0.01M PBS/5 mM EDTA pH 7.2 and the concentration of the eluent was calculated to be 2.9 mg/mL by absorbance at 280 nm. To a polypropylene tube were added 1.56 mg (0.297 mL, 23.4 nmoles, 2.0 mol equivalent) of Acr-BSA-(LC)Mal in 0.1M PBS/0.1% CHAPS/5 mM EDTA pH 6.7 followed by 0.60 mg (0.518 mL, 11.7 nmoles, 1.0 mol equivalent) of recombinant NS3h antigen in 0.01M PBS/5 mM EDTA pH 7.2. The solution was stirred for 30 min without foaming, and then allowed to incubate statically at room temperature overnight in dark. To the conjugate solution was added 0.093 mL of 0.5M phosphate buffer pH 11.0 to adjust mixture pH to 8.0. The mixture was stirred for 5 min, then 0.56 mg (0.012 mL, 120 mole equivalent) of a fresh 0.25M iodoacetic (IAA, Thermofisher Scientific, Waltham, Mass.) solution in 1N NaOH was added under mixing to effect NS3 free Cys-carboxymethylation. The mixture was reacted statically at room temperature and dark for 60 min, the final volume adjusted to 1.0 ml with 0.080 mL of 0.01M PBS/0.1% CHAPS/5 mM EDTA pH 6.3 and passed thru a PD10 column equilibrated in 0.01M PBS/0.1% CHAPS/5 mM EDTA pH 6.3 (2.5 mL elution volume). The desalted conjugate was next purified by SEC chromatography (TosoHaas G3000SWxl column, Toso Bioscience LLC, King of Prussia, Pa.) to remove undesired aggregates. The Acr-BSA-NS3h conjugate protein concentration was determined from the 280 nm absorbance of the conjugate after subtracting the 280 nm absorbance contributed by the Acr-BSA. The absorbance of a 1% (w/v) solution of NS3h of 0.95 was used to calculate the protein concentration.

Example 12

Automated Magnetic Microparticle-Based Immunoassays

The HCV NS3-derived proteins were tested for their ability to detect anti-HCV NS3 antibodies using an automated immunoanalyzer that utilizes paramagnetic microparticles and chemiluminescent conjugates (ARCHITECT® system; Abbott Laboratories; see "Bulk Reagent Random-Access Analyzer: ARCHITECT i2000" Frank A. Quinn, pages 363-367. In The Immunoassay Handbook, Third Edition, edited by David Ward, Nature Publishing Group, London, UK; U.S. Pat. No. 5,795,784 and U.S. Pat. No. 5,856,194). Assay formats examined included a 2-step format or a 1-step format. Assays can generally be described as comprising two formats: 2-step and 1-step (also described as 'pseudo' 1-step). In the 2-step format, human samples, assay specific diluent buffer and recombinant antigen coated paramagnetic microparticles are mixed into a reaction vessel, vortexed, and incubated for 18 min, wherein antibodies directed against the recombinant antigen are captured by the microparticles. Following this incubation, the microparticle/immune complexes are sequestered at the side of the reaction vessel using a magnet and the reaction supernatant is removed. The microparticles are then washed with water/detergent solution. In the second step, antibodies from the sample bound to the microparticles are detected by suspension and incubation (4 min) of the particles in buffer containing acridinium-labeled conjugate. The conjugate may be an acridinium-labeled antibody directed against human immunoglobulin(s) or an acridinium-labeled recombinant antigen. Incubation with conjugate is followed by a second wash step and finally an activation of the acridinium and simultaneous measurement of light output, which is proportional to the amount of conjugate bound onto the microparticles.

In the 1-step format, human samples, recombinant antigen coated paramagnetic microparticles and an assay specific diluent buffer containing a conjugate comprised of acridinium-labeled recombinant antigen were mixed into a reaction vessel. Following an 18-minute incubation, wherein antibodies directed against the recombinant antigen were simultaneously captured by the magnetic microparticles and bound to the acridinium-labeled recombinant antigen. Subsequently, the microparticle/immune complexes were sequestered at the side of the reaction vessel using a magnet and washed with a water/detergent mixture. Particles were then released from the vessel wall and suspended in diluent and incubated for 4 minutes. Incubation was followed by a second wash step and finally an activation of the acridinium and simultaneous measurement of light output, which was proportional to the amount of conjugate bound onto the microparticles.

Biotin-Capture Immunoassays. Biotin capture mediated immunoassays on the Architect analyzer used biotinylated NS3 protein (e,g, Nbt or Cbt as described in Example 2-6, or NS3 protein to which biotin has been coupled by chemical means in a non-site-specific manner) and a biotin capture protein (e.g. avidin, Streptavidin, Neutravidin, or anti-biotin antibody) coated paramagnetic particles. In this format, immune complexes formed between NS3 antibodies present in the sample and biotinyl-NS3 were captured onto the microparticle surface via the biotin capture protein immobilized onto the microparticle surface. A conjugate consisting of an acridinylated NS3 recombinant antigen can be added to the first step or the second step (i.e. following the capture step) to detect captured anti-NS3. Alternatively, an anti-human antibody acridinium conjugate can be added to the second step to detect captured anti-NS3.

Example 13

Immunoassay Formats covalently coupled to recombinant HCV NS3 antigen in a suitable buffer of pH 6.3) and 50 uL of paramagnetic microparticles coated with an HCV NS3 recombinant antigen in a suitable buffer of pH 6.6 containing reducing agent where indicated were mixed into a reaction vessel, vortexed, and incubated for 18 min. Following incubation, the microparticles were sequestered at the side of the reaction vessel using a magnet and the reaction supernatant was removed. The microparticles were subsequently washed with water/detergent solution. Antibodies present in the samples and captured on the microparticles were retained during the washing. In the second step, immediately following washing, 50 uL assay specific wash buffer was added to the reaction vessel, which was vortexed and then incubated for 4 minutes. Following incubation, the microparticles were sequestered at the side of the reaction vessel using a magnet and the reaction supernatant removed. The microparticles were subsequently washed with water/detergent solution. Washed particles were suspended in a basic-hydrogen peroxide containing solution to activate the acridinium with simultaneous measurement of light output (in relative light units or RLU), which is proportional to the amount of conjugate bound onto the microparticles.

Assay Format 2: Indirect 2-Step. In the first step, 10 uL sample, 90 uL assay specific diluent buffer and 50 uL of HCV NS3 coated paramagnetic microparticles (contained in a suitable buffer of pH 6.6 containing reducing agent) were

| | | The following assay formats were used: | | | |
|---|---|---|---|---|---|
| | | Reagents added in Step 1 | | | |
| Assay Format | Assay Name | Assay specific diluent buffer | Microparticle | Sample | Reagents added in Step 2 |
| 1 | Direct 1-step | Acr-BSA-NS3 | NS3 | Human plasma | Buffer |
| 2 | Indirect 2-step | Buffer only | NS3 | Human plasma | anti-Hu conjugate |
| 3 | Direct 1-Step/Capture on the Fly | NS3-biotin, Acr-BSA-NS3 | Streptavidin | Human plasma | Buffer |
| 4 | Direct 2-Step | Buffer only | NS3 | Human plasma | Acr-BSA-NS3 |
| 5 | Indirect 2-Step/Capture on the Fly | NS3-biotin | Streptavidin | Human plasma | anti-Hu conjugate |

The following human specimens were used:

Negative control sample is recalcified nonreactive human plasma (nonreactive for HBsAg, and negative for anti HCV, HIV-1 RNA or HIV-1 Ag, anti HIV 1/HIV-2 and anti-HTLV-I/HTLV-II).

Positive control sample known as 'Panel B' is a human recalcified human plasma sample reactive for a single anti-HCV marker as determined by Chiron RIBA HCV 3.0 SIA (2+ or greater c33 band intensity and nonreactive for other bands). This panel is diluted in recalcified nonreactive human plasma (nonreactive for HBsAg, and negative for anti HCV, HIV-1 RNA or HIV-1 Ag, anti HIV 1/HIV-2 and anti-HTLV-I/HTLV-II) containing disodium-EDTA and sodium azide.

A panel of commercially available human blood samples, referred to as seroconversion panels, was obtained from SeraCare (Gaithersburg, Md.) and Zeptometrix (Franklin, Mass.). Each seroconversion panel consists of serial blood samples obtained from an HCV infected individual.

Assay Format 1: Direct 1-Step. In the first step, 50 uL of human sample, 50 uL of conjugate (acridinium-labeled BSA mixed into a reaction vessel, vortexed, and incubated for 18 min. Following this incubation, the microparticles were sequestered at the side of the reaction vessel using a magnet while the reaction supernatant was removed. The microparticles were subsequently washed with water/detergent solution. Antibodies present in the samples and captured on the microparticles were retained during the washing step(s). In the second step, immediately following washing, 50 uL acridinium-labeled anti-human IgG (10 ng/mL) and IgM (1 ng/mL) mouse monoclonal antibodies in conjugate diluent was added to the reaction vessel, which was vortexed and then allowed to incubate for 4 minutes. Following incubation, the microparticles were sequestered at the side of the reaction vessel using a magnet and the reaction supernatant removed. The microparticles were subsequently washed with water/detergent solution. Washed particles were suspended in a basic-hydrogen peroxide containing solution to activate the acridinium with simultaneous measurement of light output (in relative light units or RLU), which is proportional to the amount of conjugate bound by the microparticles.

Assay Format 3: Direct 1-Step/Capture on the Fly. In the first step, 110 uL human sample, 50 to 90 uL conjugate (biotinylated recombinant HCV NS3 capture antigen, and acridinium-labeled BSA covalently coupled to recombinant HCV NS3 antigen in a suitable buffer of pH 6.3) and 50 uL of paramagnetic microparticles coated with streptavidin in particle diluent (a suitable buffer of pH 6.6 containing reducing agent) were mixed into a reaction vessel, vortexed, and incubated for 18 min. Following this incubation, the microparticles were sequestered at the side of the reaction vessel using a magnet while the reaction supernatant was removed. The microparticles were subsequently washed with water/detergent solution. Antibodies present in the samples and captured on the microparticles were retained during the washing step(s). In the second step, immediately following washing, an additional 50 uL assay specific wash buffer was added to the reaction vessel, which was vortexed and allowed to incubate for 4 minutes. Following incubation, the microparticles were sequestered at the side of the reaction vessel using a magnet and the reaction supernatant removed. The microparticles were subsequently washed with water/detergent solution. Washed particles were suspended in a basic-hydrogen peroxide containing solution to activate the acridinium with simultaneous measurement of light output (in relative light units or RLU), which is proportional to the amount of conjugate bound onto the microparticles.

Assay Format 4: Direct 2-Step. In the first step, 110 uL of sample, 90 uL assay specific diluent buffer (pH 8.4), and 50 uL of paramagnetic microparticles with immobilized HCV NS3 antigen in particle diluent (pH 6.6 with/without reducing agent as indicated) were mixed into a reaction vessel, vortexed, and incubated for 18 min. Antigen was immobilized onto particles by (a) covalent coupling using EDAC or (b) binding to immobilized streptavidin via biotin covalently linked to the antigen. Following this incubation, the microparticles were sequestered at the side of the reaction vessel using a magnet while the reaction supernatant was removed. The microparticles were subsequently washed with water/detergent solution. Antibodies present in the samples and captured on the microparticles were retained during the washing step(s). In the second step, immediately following washing, 50 uL acridinium-labeled BSA coupled to recombinant HCV NS3 antigen in conjugate diluent buffer was added to the reaction vessel, vortexed and then allowed to incubate for 4 minutes. Following incubation, the microparticles were sequestered at the side of the reaction vessel using a magnet and the reaction supernatant removed. The microparticles were subsequently washed with water/detergent solution. Washed particles were suspended in a basic-hydrogen peroxide containing solution to activate the acridinium with simultaneous measurement of light output (in relative light units or RLU), which is proportional to the amount of conjugate bound onto the microparticles.

Assay Format 5: Indirect 2-Step/Capture on the Fly. In the first step, 10 uL sample, 90 uL specimen diluent buffer containing biotinylated recombinant HCV NS3 antigen, and 50 uL paramagnetic microparticles coated with streptavidin in suitable buffer of pH 6.6 containing reducing agent were mixed into a reaction vessel, vortexed, and incubated for 18 min. Following this incubation, the microparticles were sequestered at the side of the reaction vessel using a magnet while the reaction supernatant was removed. The microparticles were subsequently washed with water/detergent solution. Antibodies present in the samples and captured on the microparticles were retained during the washing step(s). In the second step, immediately following washing, 50 uL conjugate (acridinium-labeled anti-human IgG (10 ng/mL) and acridinium-labeled IgM (1 ng/mL) mouse monoclonal antibodies was added to the reaction vessel, which was vortexed and then incubated for 4 minutes. Following incubation, the microparticles were sequestered at the side of the reaction vessel using a magnet and the reaction supernatant removed. The microparticles were subsequently washed with water/detergent solution. Washed particles were suspended in a basic-hydrogen peroxide containing solution to activate the acridinium with simultaneous measurement of light output (in relative light units or RLU), which is proportional to the amount of conjugate bound onto the microparticles.

Example 14

Immunoreactivity of 9NB49H and Cys-to-Ser Mutants

The relative immunoreactivity of the 9NB49H recombinant and mutants thereof was measured in the presence and absence of reducing agents. Assays were performed using various assay formats as described in Example 13 using a known anti-HCV NS3 positive plasma pool (Panel B) and an HCV antibody negative normal human serum. Results shown in the table below are expressed as signal-to-negative ratio (S/N). Substitution of cysteine 3 with serine improved the sensitivity of assay format 2 compared to the wild-type 9NB49H. Substitution of cysteine 4 with serine improved the sensitivity in assay format 3 compared to the wild-type 9NB49H. Substitution of cysteines 1 or 2 with serine had the largest negative impact to sensitivity in all 4 assay formats. Substitution of cysteine 3 with serine reduced the differences observed between the presence or absence of reducing agents in assay formats 2, 3 and 4. Assay format 3 (Direct 1-Step/Capture on the Fly) exhibited the greatest overall sensitivity regardless of the HCV protein used. Substitution of cysteine 3 with serine reduced the influence of reducing agent in assay format 3 while maintaining sensitivity.

| Protein | Panel B S/N In the Presence of Reducing Agents Assay Format | | | | % Difference of Panel B S/N In the Absence of Reducing Agents Assay Format | | | |
|---|---|---|---|---|---|---|---|---|
| | 1 | 2 | 3 | 4 | 1 | 2 | 3 | 4 |
| 9NB49H-Cbt | 304.4 | 15.2 | 334.4 | 170.8 | −43% | 19% | −38% | −29% |
| 9NB49H-Cbt-C1-3S | 20.8 | 4.5 | 17.2 | 5.2 | −18% | 2% | −8% | −12% |
| 9NB49H-Cbt-C4-5S | 245.8 | 14.3 | 322.0 | 153.2 | −40% | 6% | −39% | −30% |
| 9NB49H-Cbt-C1-5S | 26.0 | 1.1 | 7.4 | 4.7 | −7% | 2% | −37% | −13% |
| 9NB49H-Cbt-C1S | 74.7 | 12.0 | 217.1 | 97.8 | −34% | 0% | −63% | −59% |
| 9NB49H-Cbt-C2S | 21.3 | 4.5 | 107.8 | 17.9 | −47% | 4% | −20% | −13% |
| 9NB49H-Cbt-C3S | 184.1 | 19.0 | 313.7 | 104.6 | −39% | 14% | −14% | −5% |
| 9NB49H-Cbt-C4S | nd | 14.3 | 340.5 | 145.2 | nd | 17% | −34% | −33% |
| 9NB49H-Cbt-C5S | 261.9 | 14.8 | 255.4 | 108.7 | −48% | 22% | −55% | −56% | nd: not determined

The % difference of Panel B S/N was calculated as:

(Panel B S/N in the absence of reducing agent −
Panel B S/N in the presence of reducing agent) × 100
─────────────────────────────────────────────
(Panel B S/N in the presence of reducing agent)

Example 15

Seroconversion Sensitivity of HCV 9NB49H-Cbt vs. 9NB49H-Cbt-C3S

As shown in Example 14, Assay Format 3 (Direct 1-Step/Capture on the Fly) exhibited the greatest overall sensitivity as measured by S/N value obtained by testing an HCV antibody positive plasma pool. In addition, the 9NB49H mutant wherein the $3^{rd}$ cysteine residue was substituted with serine demonstrated the greatest resistance to reducing agent. The relative sensitivity of the wild type and C3S mutant was determined by using the Direct 1-Step/Capture on the Fly assay method (Format 3) and testing seroconversion panels from human individuals infected with HCV (Panels 919 and 6228). A S/N of 10.0 was used as a cutoff for positivity; hence, samples with S/N≥10.0 are considered to be reactive, samples with S/N<10.0 are considered to be non-reactive. Seropositive samples from each seroconversion panel are indicated by a (+) and nonreactive by (−). Panel B was used as a positive control. Results are shown in the table below. The 9NB49H-C3S-Cbt protein resulted in generally higher S/N values and also detected additional panel members as positive compared to the wild type protein.

|  | Bleed Date | ARCHITECT Anti-HCV (LN 6C37) | 9NB49H-Cbt | | 9NB49H-Cbt-C3S | |
|---|---|---|---|---|---|---|
| Panel B | N/A | 47.8 | 187.9 | | 251.3 | |
| 919-1 | 31-Dec-99 | 9.6 | 13.3 | + | 24.5 | + |
| 919-2 | 7-Jan-00 | 9.1 | 13.2 | + | 24.3 | + |
| 919-3 | 12-Jan-00 | 9.4 | 13.1 | + | 23.2 | + |
| 919-4 | 25-Jan-00 | nd | 15.6 | + | 28.7 | + |
| 919-5 | 28-Jan-00 | 95.5 | 269.5 | + | 450.2 | + |
| 919-6 | 1-Feb-00 | 210.1 | 89.1 | + | 241.3 | + |
| 919-7 | 1-Apr-00 | 196.5 | 61.4 | + | 152.9 | + |
| 6228-1 | 20-Nov-96 | 0.7 | 1.0 | − | 0.7 | − |
| 6228-2 | 22-Nov-96 | 0.6 | 0.9 | − | 1.0 | − |
| 6228-3 | 27-Nov-96 | 0.9 | 1.1 | − | 0.8 | − |
| 6228-4 | 29-Nov-96 | 0.6 | 0.8 | − | 1.0 | − |
| 6228-5 | 4-Dec-96 | 0.8 | 0.8 | − | 0.7 | − |
| 6228-6 | 6-Dec-96 | 0.6 | 0.8 | − | 0.8 | − |
| 6228-7 | 11-Dec-96 | 1.7 | 0.9 | − | 0.8 | − |
| 6228-8 | 14-Dec-96 | 1.7 | 1.0 | − | 0.9 | − |
| 6228-9 | 18-Dec-96 | 17.6 | 6.2 | − | 12.3 | + |
| 6228-10 | 21-Dec-96 | 63.2 | 10.2 | + | 19.3 | + |
| 6228-11 | 26-Dec-96 | 90.1 | 9.2 | − | 16.3 | + |
| 6228-12 | 28-Dec-96 | 96.2 | 11.3 | + | 16.4 | + |

Example 16

Seroconversion Sensitivity of the NS3h Domain Variants

To identify domains of the HCV NS3 helicase protein (NS3h) contributing to immunoreactivity among HCV infected individuals, a collection of recombinant proteins was made as described in Example 5. These site-specifically biotinylated proteins were used in Assay Format 5 (Indirect 2-Step/Capture on the Fly, Example 13) to measure their immunoreactivity by using an HCV positive control human plasma pool (Panel B) and a set of seroconversion panels from human individuals infected with HCV (Panels 6224, 6228 and 9044). A S/N of 10.0 was used as a cutoff for positivity; hence, samples with S/N≥10.0 are considered to be reactive, samples with S/N<10.0 are considered to be non-reactive. Panel B was used as a positive control. Results expressed as S/N ratios are shown in the table below. NS3h-Cbt-C3S resulted in the greatest seroconversion sensitivity (most reactive bleeds) followed by the NS3h-Cbt protein. NS3h-Cbt-C3S resulted in 2-15 fold greater S/N, depending on the panel member, as compared to 9NB49H-Cbt. NS3h-Cbt resulted in 3-10 fold greater S/N, depending on the panel member, as compared to 9NB49H-Cbt. The NS3h-dl-Cbt antigen exhibited 2-fold greater S/N, depending on the panel member, as compared to 9NB49H-Cbt despite the fact the 9NB49H is inclusive of the region expressed as d1-Cbt.

| Panel Member | Bleed Date | ARCHITECT Anti-HCV (LN 6C37) | NS3h-Cbt Domain Variant 9NB49H-Cbt | d1-Cbt | d2-Cbt | d2ext | d1d2ext | NS3h | NS3h-C3S |
|---|---|---|---|---|---|---|---|---|---|
| Panel B | N/A | 47.8 | 5.7 | 7.5 | 1.7 | 1.7 | 5.6 | 25.9 | 35.3 |
| 6224-01 | 28-Oct-96 | 1.1 | 0.9 | 0.9 | 0.9 | 0.8 | 0.8 | 0.9 | 1.0 |
| 6224-02 | 31-Oct-96 | 1.1 | 0.6 | 0.7 | 0.7 | 0.7 | 0.6 | 0.7 | 0.7 |
| 6224-03 | 4-Nov-96 | 1.5 | 0.7 | 0.7 | 0.7 | 0.7 | 0.7 | 1.9 | 2.4 |
| 6224-04 | 8-Nov-96 | 2.6 | 0.8 | 0.8 | 0.7 | 0.7 | 0.8 | 8.2 | 12.0 |
| 6224-05 | 16-Nov-96 | 30.3 | 2.8 | 4.9 | 0.7 | 0.7 | 3.3 | 24.6 | 33.0 |
| 6224-06 | 19-Nov-96 | 51.6 | 4.8 | 8.3 | 0.6 | 0.7 | 5.2 | 29.6 | 39.9 |
| 6228-01 | 20-Nov-96 | 0.7 | 0.9 | 1.0 | 1.0 | 1.0 | 1.0 | 1.0 | 0.9 |
| 6228-02 | 22-Nov-96 | 0.6 | 0.8 | 0.9 | 0.9 | 0.9 | 0.9 | 1.0 | 1.0 |
| 6228-03 | 27-Nov-96 | 0.9 | 1.0 | 1.0 | 1.0 | 1.0 | 1.0 | 1.1 | 1.0 |
| 6228-04 | 29-Nov-96 | 0.6 | 0.9 | 0.9 | 0.9 | 0.9 | 0.9 | 0.9 | 0.8 |
| 6228-05 | 4-Dec-96 | 0.8 | 1.0 | 1.0 | 1.1 | 1.1 | 1.1 | 1.1 | 1.0 |

-continued

| Panel Member | Bleed Date | ARCHITECT Anti-HCV (LN 6C37) | NS3h-Cbt Domain Variant | | | | | | |
|---|---|---|---|---|---|---|---|---|---|
| | | | 9NB49H-Cbt | d1-Cbt | d2-Cbt | d2ext | d1d2ext | NS3h | NS3h-C3S |
| 6228-06 | 6-Dec-96 | 0.6 | 0.9 | 1.0 | 0.9 | 0.9 | 1.0 | 1.0 | 0.9 |
| 6228-07 | 11-Dec-96 | 1.7 | 1.0 | 1.1 | 1.0 | 1.0 | 1.1 | 1.4 | 1.5 |
| 6228-08 | 14-Dec-96 | 1.7 | 1.0 | 1.0 | 1.0 | 1.0 | 1.0 | 1.3 | 1.6 |
| 6228-09 | 18-Dec-96 | 17.6 | 1.9 | 3.2 | 1.1 | 1.1 | 1.9 | 8.4 | 12.9 |
| 6228-10 | 21-Dec-96 | 63.2 | 4.7 | 10.2 | 1.0 | 1.0 | 4.1 | 23.8 | 34.4 |
| 6228-11 | 26-Dec-96 | 90.1 | 6.2 | 15.2 | 1.2 | 1.1 | 6.1 | 31.9 | 42.4 |
| 6228-12 | 28-Dec-96 | 96.2 | 7.1 | 16.5 | 1.0 | 1.0 | 7.4 | 32.0 | 42.1 |
| 9044-01 | 14-Apr-97 | 1.0 | 1.8 | 1.8 | 1.8 | 1.8 | 1.9 | 1.9 | 1.8 |
| 9044-02 | 18-Apr-97 | 0.9 | 1.7 | 1.6 | 1.6 | 1.7 | 1.6 | 1.7 | 1.5 |
| 9044-03 | 1-May-97 | 1.1 | 1.7 | 1.9 | 1.9 | 1.8 | 1.9 | 2.0 | 2.1 |
| 9044-04 | 5-May-97 | 12.2 | 2.4 | 3.3 | 1.8 | 1.9 | 2.5 | 11.8 | 17.7 |
| 9044-05 | 9-May-97 | 68.5 | 6.3 | 13.9 | n/a | 2.7 | 6.6 | 29.3 | 39.3 |
| 9044-06 | 13-May-97 | 102.8 | 11.5 | 22.4 | 3.0 | 3.3 | 14.0 | 36.3 | 49.7 |

Example 17

Relative Immunoreactivity of 9NB49H, NS3h and NS3h-C3S

To identify which combinations of NS3 protein provided the highest antibody detection assay sensitivity, various combinations of HCV NS3 recombinant proteins were examined by using Assay Format 3 (Direct 1-Step/Capture on the Fly, Example 13). HCV NS3 proteins were labeled with Acr-BSA (acridinium-labeled BSA) and/or used as site-specifically biotinylated capture proteins (i.e. possessing C-terminally biotinylated tags or Cbt). The latter were examined at three different concentrations. HCV positive control human plasma pool (Panel B) was used as a positive control and a normal human plasma pool known to be negative for HCV antibodies was used as the negative control. Results are shown in the table below and are expressed in relative light units (RLU). All combinations of HCV NS3 proteins detected antibodies present in the positive control sample, however, the combination of NS3h-Cbt and Acr-BSA-NS3h exhibited the highest sensitivity.

| Conjugate Protein | Capture Protein | Capture Protein Concentration (ng/mL) | Negative Control RLUs | Panel B RLUs | Panel B S/N |
|---|---|---|---|---|---|
| Acr-BSA-9NB49H | 9NB49H-Cbt | 150 | 731.0 | 150719.7 | 206.2 |
| | | 450 | 792.0 | 148570.0 | 187.6 |
| | | 600 | 827.7 | 144933.0 | 175.1 |
| | NS3h-Cbt | 150 | 612.0 | 178788.7 | 292.1 |
| | | 450 | 661.0 | 184932.3 | 279.8 |
| | | 600 | 616.7 | 172940.7 | 280.4 |
| | NS3h-C3S-Cbt | 150 | 654.0 | 160863.3 | 246.0 |
| | | 450 | 793.7 | 170080.3 | 214.3 |
| | | 600 | 780.3 | 163621.7 | 209.7 |
| Acr-BSA-NS3h | 9NB49H-Cbt | 150 | 1100.7 | 35869.3 | 32.6 |
| | | 450 | 1306.0 | 34948.7 | 26.8 |
| | | 600 | 1464.3 | 32539.3 | 22.2 |
| | NS3h-Cbt | 150 | 969.0 | 281975.3 | 291.0 |
| | | 450 | 1103.3 | 395540.7 | 358.5 |
| | | 600 | 1127.7 | 440955.0 | 391.0 |
| | NS3h-Cbt-C3S | 150 | 1047.0 | 233363.0 | 222.9 |
| | | 450 | 1086.7 | 343993.7 | 316.6 |
| | | 600 | 1243.7 | 377309.3 | 303.4 |

Example 18

Seroconversion Sensitivity of 9NB49H, NS3h and NS3h-C3S

The various combinations of NS3 recombinant antigens were examined for their ability to detect antibodies among individual serum samples from a set of seroconversion panels from HCV infected individuals. Data was generated by using Assay Format 3 (Direct 1-step/Capture-on-the-Fly, Example 13). An S/N of 10.0 was used as a cutoff for positivity; hence, samples with S/N≥10.0 are considered to be reactive, samples with S/N<10.0 are considered to be non-reactive. Panel B was used as a positive control. Results expressed as S/N ratios are shown in the table below. The assay using Acr-BSA-NS3h and NS3h-Cbt resulted in the greatest seroconversion sensitivity, i.e. most reactive panel members detected with the highest S/N value.

| Panel Member | Bleed Date | ARCHITECT Anti-HCV (LN 6C37) | Acr-BSA-9NB49H | | | Acr-BSA-NS3h | | |
|---|---|---|---|---|---|---|---|---|
| | | | 9NB49H-Cbt | NS3h-Cbt | NS3h-Cbt-C3S | 9NB49H-Cbt | NS3h-Cbt | NS3h-Cbt-C3S |
| PNLB | N/A | 47.8 | 159.3 | 235.6 | 174.1 | 10.4 | 261.9 | 191.8 |
| 6224-01 | 28-Oct-96 | 1.1 | 0.9 | 1.0 | 1.0 | 1.0 | 1.1 | 1.1 |
| 6224-02 | 31-Oct-96 | 1.1 | 1.6 | 1.5 | 1.0 | 1.2 | 1.1 | 1.1 |
| 6224-03 | 4-Nov-96 | 1.5 | 1.2 | 1.1 | 1.1 | 1.2 | 1.9 | 2.2 |
| 6224-04 | 8-Nov-96 | 2.6 | 5.7 | 6.1 | 5.6 | 1.4 | 25.5 | 25.1 |
| 6224-05 | 16-Nov-96 | 30.3 | 40.3 | 50.2 | 32.4 | 3.1 | 379.9 | 279.1 |
| 6224-06 | 19-Nov-96 | 51.6 | 36.5 | 51.0 | 31.7 | 3.4 | 450.0 | 322.2 |
| 6228-01 | 20-Nov-96 | 0.7 | 1.1 | 1.0 | 0.9 | 1.2 | 1.0 | 1.1 |
| 6228-02 | 22-Nov-96 | 0.6 | 1.3 | 1.0 | 1.0 | 1.3 | 1.1 | 1.2 |
| 6228-03 | 27-Nov-96 | 0.9 | 0.9 | 1.1 | 1.0 | 1.3 | 1.0 | 1.1 |
| 6228-04 | 29-Nov-96 | 0.6 | 1.0 | 1.1 | 1.0 | 1.1 | 1.0 | 1.0 |
| 6228-05 | 4-Dec-96 | 0.8 | 0.9 | 1.1 | 0.9 | 1.3 | 1.0 | 1.1 |
| 6228-06 | 6-Dec-96 | 0.6 | 1.1 | 1.0 | 1.0 | 1.2 | 1.0 | 1.1 |
| 6228-07 | 11-Dec-96 | 1.7 | 1.1 | 1.1 | 1.0 | 1.1 | 1.2 | 1.2 |
| 6228-08 | 14-Dec-96 | 1.7 | 1.1 | 1.1 | 1.1 | 1.2 | 1.4 | 1.3 |
| 6228-09 | 18-Dec-96 | 17.6 | 11.5 | 17.3 | 12.8 | 5.5 | 41.1 | 34.6 |
| 6228-10 | 21-Dec-96 | 63.2 | 11.8 | 37.2 | 29.2 | 9.0 | 253.8 | 183.9 |
| 6228-11 | 26-Dec-96 | 90.1 | 10.8 | 42.6 | 32.5 | 8.8 | 303.9 | 212.2 |
| 6228-12 | 28 Dec-96 | 96.2 | 11.6 | 46.5 | 32.7 | 8.9 | 337.7 | 245.4 |
| 9044-01 | 14-Apr-97 | 1.0 | 1.1 | 1.0 | 1.0 | 1.2 | 1.1 | 1.0 |
| 9044-02 | 18-Apr-97 | 0.9 | 1.1 | 1.1 | 1.0 | 1.3 | 1.1 | 1.1 |
| 9044-03 | 1-May-97 | 1.1 | 1.4 | 1.5 | 1.3 | 1.3 | 1.1 | 1.1 |
| 9044-04 | 5-May-97 | 12.2 | 14.3 | 8.8 | 6.2 | 5.6 | 21.5 | 20.1 |
| 9044-05 | 19-May-97 | 68.5 | 90.1 | 59.8 | 44.1 | 25.4 | 261.0 | 189.5 |
| 9044-06 | 13-May-97 | 102.8 | 149.0 | 104.6 | 65.3 | 40.1 | 331.0 | 238.2 |

Example 19

Relative Immunoreactivity of NS3h Variants

To compare the relative immunoreactivity of the NS3h variants described in Example 6 for human anti-NS3 antibodies, the following method was used to control for potential differences in streptavidin microparticle capture of biotinylated NS3 proteins. The method uses Assay Format 5 as described in Example 13 wherein the purified NS3 recombinant antigens to be tested were diluted in specimen diluent buffer to the same protein concentration prior to testing. The same set of diluted antigens are tested in two assays, both using Assay Format 5, in which the NS3 protein captured by the streptavidin microparticle in the first assay step is tested/interrogated by (a) anti-HCV NS3 positive human plasma pool known to contain antibodies directed to NS3 (i.e. Panel B, as described in Example 14) and (b) an anti-NS3 mouse monoclonal antibody directed against an amino-terminal linear epitope whose sequence is present and conserved among the NS3 recombinant proteins and variants thereof (i.e. 9NB49H and NS3h). The amount of anti-NS3 human antibody bound was determined by using an acridinylated anti-Human IgG conjugate. The amount of anti-NS3 monoclonal antibody bound to the particle was determined by the same assay format but, the anti-human IgG conjugate was replaced with an anti-mouse polyclonal antibody raised in goat and labeled with acridinium. The ratio of RLU's between the two assays provides a means for normalization of the anti-NS3 human antibody immunoreactivity relative to the amount of NS3 recombinant antigen on the paramagnetic microparticles. Normalized immunoreactivity is calculated by dividing the RLU's from the anti-Human assay by 33×log 10 of the RLU's from the anti-mouse assay. This transformation of the data allowed for a direct linear correlation between the two assays to be established.

Results of an experiment using 150 ng/mL of each recombinant protein are shown in the table below. Normalized results are shown relative to either 9NB49H or NS3h. All NS3h variants exhibit higher reactivity for Panel B compared to 9NB49H. Some NS3h variants exhibit greater relative immunoreactivity compared to the wild type NS3h suggesting that certain mutations to residues known to be involved in ATPase or ATP binding can result in an NS3h with greater immunoreactivity. Mutation of Cys14 to Ser, either alone or in combination with another mutation, results in a much lower immunoreactivity of NS3h.

| NS3-Cbt Protein (Mutant) | Relative to 9NB49H | Relative to NS3h |
|---|---|---|
| 9NB49H | 1.00 | 0.43 |
| NS3h | 2.35 | 1.00 |
| E127Q | 3.04 | 1.30 |
| D126N | 2.81 | 1.20 |
| R303K | 2.71 | 1.16 |
| H129A + R300A | 2.69 | 1.15 |
| S47A | 2.58 | 1.10 |
| R300A | 2.52 | 1.07 |
| T48E | 2.49 | 1.06 |
| Y77S | 2.44 | 1.04 |
| T255G | 2.28 | 0.97 |
| K46N | 2.27 | 0.97 |
| H129A | 2.23 | 0.95 |
| W337A | 2.23 | 0.95 |
| C5S | 3.07 | 1.31 |
| C11S | 2.98 | 1.27 |
| C3S + C5S | 2.76 | 1.17 |
| P66Q + C3S + C5S | 2.75 | 1.17 |
| C10S | 2.66 | 1.13 |
| C3S + C11S | 2.56 | 1.09 |
| C3S + C10S | 2.17 | 0.93 |
| C3S + C14S | 1.36 | 0.58 |
| C14S | 1.21 | 0.52 |

Example 20

Relative Sensitivity of the Direct vs. Indirect Labeling of the NS3h Protein

NS3h recombinant antigen was labeled 'indirectly', i.e. via conjugation of acridinium-labeled-BSA to cysteinyl-thiol as described in Example 11 or 'directly' by using acridinium-maleimide as described in Example 11.

Data was generated by using Assay Format 5 (Direct 2-step/Capture-on-the Fly) as described in Example 13. An S/N of 10.0 was used as a cutoff for positivity; hence, samples with S/N≥10.0 are considered to be reactive, samples with S/N<10.0 are considered to be non-reactive. Panel B was used as a positive control. Results are shown in the table below.

Use of the direct labeling method results in conjugate with greatly reduced ability to detect HCV NS3 antibodies as compared to the indirectly labeled NS3h conjugate.

| Labeling Method | Direct | Indirect |
|---|---|---|
| Negative Control RLUs | 5474.7 | 477.0 |
| Panel B RLUs | 3266.7 | 309120.0 |
| Panel B S/N | 0.6 | 648.1 |

The invention claimed is:

1. A recombinant HCV NS3 antigen comprising a NS3 helicase sequence that comprises each of domains I, II, and III of said helicase, wherein said antigen has increased immunoreactivity against HCV antibodies from test sample as compared to C33 antigen, wherein said recombinant HCV NS3 antigen comprises one or more of the characteristics selected from the group consisting of:
diminished ATP-binding activity as compared to the ATP-binding activity of wild-type NS3 helicase;
diminished ATPase activity as compared to wild-type NS3 helicase; and
increased redox stability as compared to the redox stability of wild-type NS3 helicase,
wherein said wild-type HCV NS3 helicase comprises the amino acid sequence of SEQ ID NO: 87, wherein the C33 antigen corresponds to positions 1192-1457 of SEQ ID NO: 88, and
wherein said antigen comprises the amino acid sequence of SEQ ID NO:87 comprising at least one of the following mutations:
(a) a mutation of one or more cysteine residues to a corresponding serine residue, the one or more cysteine residues selected from the group consisting of C368, C374, C499, and C525 of wild-type HCV NS3 protein which correspond to C203, C209, C334, and C360 of SEQ ID NO: 87, wherein the wild-type HCV NS3 protein comprises the sequence of SEQ ID NO: 87; or
(b) a mutation that diminishes ATP binding or diminishes ATPase activity comprising a replacement of one or more of the amino acid residues with any other amino acid residue, the one or more of the amino acid residues selected from the group consisting of S211, T212, Y241, and T419 of wild-type HCV NS3 protein which correspond to S46, T47, Y76, and T254 of SEQ ID NO: 87.

2. The recombinant HCV NS3 antigen of claim 1, wherein said antigen further comprises addition of at least one cysteine residue to the C-terminal end of said NS3 helicase.

3. The recombinant HCV NS3 antigen of claim 1, wherein said mutation comprises a replacement of one or more of the amino acid residues with any other amino acid residue, the one or more of the amino acid residues selected from the group consisting of S211, T212, Y241, and T419 of wild-type HCV NS3 protein which correspond to S46, T47, Y76, and T254 of SEQ ID NO: 87.

4. The recombinant HCV NS3 antigen of claim 1, wherein said mutation comprises a mutation of one or more of the cysteine residues selected from the group consisting of C368, C374, C499, and C525 of wild-type HCV NS3 protein which correspond to C203, C209, C334, and C360 of SEQ ID NO:87.

5. The recombinant HCV NS3 antigen of claim 4, wherein said antigen further comprises addition of at least one cysteine residue to the C-terminus end of said NS3 helicase.

6. The recombinant HCV NS3 antigen of claim 3, wherein said antigen further comprises addition of at least one cysteine residue to the C-terminus end of said NS3 helicase.

7. The recombinant HCV NS3 antigen of claim 6, wherein said addition of a cysteine residue to the C-terminal end of said NS3 helicase comprises addition of a sequence selected from the group consisting of GGCSGGA (SEQ ID NO: 82), DECHSTD (SEQ ID NO: 84), and SKKKCDE (SEQ ID NO: 86) to the C-terminal end of said NS3 helicase, optionally further comprising conjugation to a signal generating moiety.

8. A recombinant HCV NS3 antigen comprising a NS3 helicase sequence that comprises each of domains I, II, and III of said helicase, wherein said antigen has increased immunoreactivity against HCV antibodies from test sample as compared to C33 antigen, wherein said recombinant HCV NS3 antigen comprises one or more of the characteristics selected from the group consisting of:
diminished ATP-binding activity as compared to the ATP-binding activity of wild-type NS3 helicase;
diminished ATPase activity as compared to wild-type NS3 helicase; and
increased redox stability as compared to the redox stability of wild-type NS3 helicase,
wherein said wild-type HCV NS3 helicase comprises the amino acid sequence of SEQ ID NO: 87, wherein the C33 antigen corresponds to positions 1192-1457 of SEQ ID NO: 88, and
wherein said antigen comprises the amino acid sequence of SEQ ID NO:87 comprising at least one mutation that diminishes ATP binding or diminishes ATPase activity and is a replacement of one or more of the amino acid residues with any other amino acid residue, the one or more of the amino acid residues selected from the group consisting of K210, S211, T212, Y241, D290, E291, H293, T419, Q460, R464, R467, and W501 of wild-type HCV NS3 protein which correspond to K45, S46, T47, Y76, D125, E126, H198, T254, Q295, R299, R302, and W366 of SEQ ID NO:87 wherein the wild-type HCV NS3 protein comprises the sequence of SEQ ID NO: 87,
wherein said antigen further comprises addition of at least one cysteine residue to the C-terminal end of said NS3 helicase, and
wherein said addition of at least one cysteine residue to the C-terminal end of said NS3 helicase comprises addition of a sequence selected from the group consisting of GSGSGHHHHHHHHGGCSGGARSGC (SEQ ID NO: 89);
GSGSGHHHHHHHHDECHSTDRSGC (SEQ ID NO: 90); and
GSGCGHHHHHHHHGGCSGGA (SEQ ID NO: 91), optionally further comprising conjugation to a signal generating moiety.

9. The recombinant HCV NS3 antigen of claim 6, wherein said antigen further comprises a histidine tag.

10. The recombinant HCV NS3 antigen of claim 9, wherein said histidine tag is located between the C-terminus of SEQ ID NO:87 and the N-terminus of said added sequence.

11. The recombinant HCV NS3 antigen claim 1, wherein said antigen is biotinylated either at the N-terminus, the C-terminus or at a site specific biotinylation distal from the C or N terminus of said antigen.

12. An isolated nucleic acid encoding a recombinant HCV antigen of claim 1.

13. An expression vector comprising an isolated nucleic acid of claim 12.

14. A host cell transformed or transfected with an expression vector of claim 13.

15. An immunodiagnostic reagent comprising the recombinant HCV antigen of claim 1.

16. The immunodiagnostic reagent of claim 15, further comprising a solid support.

17. The immunodiagnostic reagent of claim 15, wherein said recombinant antigen is detectably labeled with a fluorescent label.

18. A kit comprising an immunodiagnostic reagent of claim 15 and further comprising an additional isolated HCV antigen comprising an epitope that is immunoreactive with an anti-HCV antibody.

19. The kit of claim 18, wherein said recombinant HCV NS3 antigen and said additional HCV antigen are either co-coated on the same solid phase, or are each coated on a separate solid phase.

20. The kit of claim 19, further comprising antibodies for detection of human antibodies.

21. The kit of claim 19, further comprising anti-HCV antibodies, optionally comprising a detectable label.

22. An immunoassay method of determining the presence of anti-HCV antibodies in a test sample, comprising contacting said test sample with an immunodiagnostic agent of claim 15 under conditions to allow a complex to from between said recombinant HCV NS3 antigen and said anti-HCV antibodies in said test sample, and detecting the presence of said complex, wherein presence of said complex is indicative of anti-HCV antibodies in said test sample.

23. The immunoassay method of claim 22, wherein said detection of said complex formation is detected by determining binding of labeled anti-human antibodies to said complex, wherein said anti-human antibodies are labeled with a fluorescent label.

24. The immunoassay method of claim 22, wherein the recombinant HCV NS3 antigen is coated on microparticles.

25. The immunoassay method of claim 22, wherein said method further comprises assaying said test sample to determine the presence of antibodies against HCV core antigen, optionally wherein said recombinant HCV NS3 antigen and said HCV core antigen are co-coated on the same microparticle or are coated on separate microparticles.

26. The immunoassay method of claim 25, wherein the test sample was obtained from a patient and the method further comprises diagnosing, prognosticating, or assessing the efficacy of a therapeutic/prophylactic treatment of the patient, wherein, if the method further comprises assessing the efficacy of a therapeutic/prophylactic treatment of the patient, the method optionally further comprises modifying the therapeutic/prophylactic treatment of the patient as needed to improve efficacy.

27. The immunoassay method of claim 25, wherein the method is adapted for use in an automated system or a semi-automated system.

28. The recombinant HCV NS3 antigen of claim 1, wherein said recombinant HCV NS3 antigen comprises increased redox stability as compared to the redox stability of wild-type NS3 helicase.

29. The recombinant HCV NS3 antigen of claim 8, wherein said antigen further comprises a mutation of one or more of the cysteine residues to any other amino acid, the one or more of the cysteine residues selected from the group consisting of C292, C368, C374 C499, and C525 of wild-type HCV NS3 protein which correspond to C127, C203, C209, C334, and C360 of SEQ ID NO: 87.

* * * * *

SEQUENCE LISTING

```
<160> NUMBER OF SEQ ID NOS: 122

<210> SEQ ID NO 1
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gctgttgact ttatcccggt tgaaaatctc gagactacta tgcgttctcc ggttttcact        60
gacaactctt ctccgccggt tgttccgcag tctttccagg ttgctcacct gcatgctccg       120
actggttctg gtaaatctac taaagttcca gctgcttacg ctgctcaggg ttacaaagtt       180
ctggttctga accgtctgt tgctgctact ctgggtttcg gcgcctacat gtctaaagct        240
cacggtatcg acccgaacat tcgtactggt gtacgtacta tcactactgg ttctccgatc       300
acttactcta cttacggtaa attcctggct gacggtggtt gctctggtgg tgcttacgat       360
atcatcatct gcgacgaatg ccactctact gacgctactt ctatcctggg tatcggtacc       420
gttctggacc aggctgaaac tgcaggtgct cgtctggttg ttctggctac tgctactccg       480
ccgggttctg ttactgttcc gcacccgaac atcgaagaag ttgctctgtc gactactggt       540
gaaatcccgt tctacggtaa agctatcccg ctcgaggtta tcaaaggtgg tcgtcacctg       600 atttctctgcc actctaaaaa aaaatgcgac gaactggctg ctaagcttgt tgctctgggt       660
atcaacgctg ttgcttacta ccgtggtctg gacgtttctg ttatcccgac ttctggtgac       720
gttgttgttg tggccactga cgctctgatg actggttaca ctggtgactt cgactctgtt       780
atcgattgca acacttgc                                                     798

<210> SEQ ID NO 2
<211> LENGTH: 266
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 2

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265
```

<210> SEQ ID NO 3
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggta gctctggtgg tgcttacgat     360
```

```
atcatcatct gcgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgc                                                  798
```

<210> SEQ ID NO 4
<211> LENGTH: 266
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 4

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Ser Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265
```

<210> SEQ ID NO 5
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| gctgttgact | ttatcccggt | tgaaaatctc | gagactacta | tgcgttctcc | ggttttcact | 60 |
| gacaactctt | ctccgccggt | tgttccgcag | tctttccagg | ttgctcacct | gcatgctccg | 120 |
| actggttctg | gtaaatctac | taagttcca | gctgcttacg | ctgctcaggg | ttacaaagtt | 180 |
| ctggttctga | acccgtctgt | tgctgctact | ctgggtttcg | gcgcctacat | gtctaaagct | 240 |
| cacggtatcg | acccgaacat | tcgtactggt | gtacgtacta | tcactactgg | ttctccgatc | 300 |
| acttactcta | cttacggtaa | attcctggct | gacggtggtt | gctctggtgg | tgcttacgat | 360 |
| atcatcatca | gcgacgaatg | ccactctact | gacgctactt | ctatcctggg | tatcggtacc | 420 |
| gttctggacc | aggctgaaac | tgcaggtgct | cgtctggttg | ttctggctac | tgctactccg | 480 |
| ccgggttctg | ttactgttcc | gcacccgaac | atcgaagaag | ttgctctgtc | gactactggt | 540 |
| gaaatcccgt | tctacggtaa | agctatcccg | ctcgaggtta | tcaaaggtgg | tcgtcacctg | 600 |
| attttctgcc | actctaaaaa | aaaatgcgac | gaactggctg | ctaagcttgt | tgctctgggt | 660 |
| atcaacgctg | ttgcttacta | ccgtggtctg | gacgtttctg | ttatcccgac | ttctggtgac | 720 |
| gttgttgttg | tggccactga | cgctctgatg | actggttaca | ctggtgactt | cgactctgtt | 780 |
| atcgattgca | acacttgc | | | | | 798 |

<210> SEQ ID NO 6
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Ser Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

-continued

```
Pro Gly Ser Val Thr Val Pro His Pro Asn Ile Glu Glu Val Ala Leu
            165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
        210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265
```

<210> SEQ ID NO 7
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
gctgttgact ttatcccggt tgaaaatctc gagactacta tgcgttctcc ggttttcact    60
gacaactctt ctccgccggt tgttccgcag tctttccagg ttgctcacct gcatgctccg   120
actggttctg gtaaatctac taaagttcca gctgcttacg ctgctcaggg ttacaaagtt   180
ctggttctga accgtctgt tgctgctact ctgggtttcg cgcctacat gtctaaagct    240
cacggtatcg acccgaacat tcgtactggt gtacgtacta tcactactgg ttctccgatc   300
acttactcta cttacggtaa attcctggct gacggtggtt gctctggtgg tgcttacgat   360
atcatcatct gcgacgaaag ccactctact gacgctactt ctatcctggg tatcggtacc   420
gttctggacc aggctgaaac tgcaggtgct cgtctggttg ttctggctac tgctactccg   480
ccgggttctg ttactgttcc gcacccgaac atcgaagaag ttgctctgtc gactactggt   540
gaaatcccgt tctacggtaa agctatcccg ctcgaggtta tcaaaggtgg tcgtcacctg   600
attttctgcc actctaaaaa aaaatgcgac gaactggctg ctaagcttgt tgctctgggt   660
atcaacgctg ttgcttacta ccgtggtctg gacgtttctg ttatcccgac ttctggtgac   720
gttgttgttg tggccactga cgctctgatg actggttaca ctggtgactt cgactctgtt   780
atcgattgca acacttgc                                                 798
```

<210> SEQ ID NO 8
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
```

```
                35                  40                  45
Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                 85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Ser His
                115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
                260                 265
```

<210> SEQ ID NO 9
<211> LENGTH: 798
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 9

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct      240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttcagcc actctaaaaa aaaatgcgac gaactggctg ctaagcttgt tgctctgggt     660
atcaacgctg ttgcttacta ccgtggtctg gacgtttctg ttatcccgac ttctggtgac     720
```
gttgttgttg tggccactga cgctctgatg actggttaca ctggtgactt cgactctgtt     780
atcgattgca acacttgc                                                   798

<210> SEQ ID NO 10
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 11
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gctgttgact ttatcccggt tgaaaatctc gagactacta tgcgttctcc ggttttcact     60

```
gacaactctt ctccgccggt tgttccgcag tctttccagg ttgctcacct gcatgctccg    120
actggttctg gtaaatctac taaagttcca gctgcttacg ctgctcaggg ttacaaagtt    180
ctggttctga accgtctgt tgctgctact ctgggtttcg gcgcctacat gtctaaagct    240
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaggtgg tcgtcacctg    600 attttctgcc actctaaaaa aaaaagcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgc                                                  798
```

<210> SEQ ID NO 12
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Ser Asp Glu Leu Ala Ala Lys Leu Val Ala Leu Gly Ile Asn Ala Val
    210                 215                 220
```

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 13
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taagttccag ctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggta gctctggtgg tgcttacgat     360
atcatcatca gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgc                                                   798

<210> SEQ ID NO 14
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Ser Ser Gly Gly Ala Tyr Asp Ile Ile Ile Ser Asp Glu Ser His
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
        210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 15
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg cgcctacat gtctaaagct      240 cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600 atttttcagcc actctaaaaa aaaaagcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgc                                                    798

<210> SEQ ID NO 16
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
            195                 200                 205

Ser Asp Glu Leu Ala Ala Lys Leu Val Ala Leu Gly Ile Asn Ala Val
        210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 17
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gctgttgact ttatcccggt tgaaaatctc gagactacta tgcgttctcc ggttttcact    60
gacaactctt ctccgccggt tgttccgcag tctttccagg ttgctcacct gcatgctccg   120
actggttctg gtaaatctac taaagttcca gctgcttacg ctgctcaggg ttacaaagtt   180
ctggttctga cccgtctgt tgctgctact ctgggtttcg gcgcctacat gtctaaagct   240
cacggtatcg acccgaacat tcgtactggt gtacgtacta tcactactgg ttctccgatc   300
acttactcta cttacggtaa attcctggct gacggtggta gctctggtgg tgcttacgat   360
atcatcatca gcgacgaaag ccactctact gacgctactt ctatcctggg tatcggtacc   420
gttctggacc aggctgaaac tgcaggtgct cgtctggttg ttctggctac tgctactccg   480

```
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttcagcc actctaaaaa aaaaagcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgc                                                  798
```

<210> SEQ ID NO 18
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Ser Ser Gly Gly Ala Tyr Asp Ile Ile Ser Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
        195                 200                 205

Ser Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 19
<211> LENGTH: 1401
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 19

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aacgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccccggtc actaaatca ttatgacttg catgagcgca    1380
gacctggaag tggtgacttc c                                              1401
```

<210> SEQ ID NO 20
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala

-continued

```
                65                  70                  75                  80
        His Gly Ile Asp Pro Asn Ile Arg Thr Gly Val Arg Thr Ile Thr Thr
                            85                  90                  95
        Gly Ser Pro Ile Thr Tyr Ser Thr Tyr Gly Lys Phe Leu Ala Asp Gly
                        100                 105                 110
        Gly Cys Ser Gly Gly Ala Tyr Asp Ile Ile Cys Asp Glu Cys His
                    115                 120                 125
        Ser Thr Asp Ala Thr Ser Ile Leu Gly Ile Gly Thr Val Leu Asp Gln
                130                 135                 140
        Ala Glu Thr Ala Gly Ala Arg Leu Val Val Leu Ala Thr Ala Thr Pro
        145                 150                 155                 160
        Pro Gly Ser Val Thr Val Pro His Pro Asn Ile Glu Glu Val Ala Leu
                        165                 170                 175
        Ser Thr Thr Gly Glu Ile Pro Phe Tyr Gly Lys Ala Ile Pro Leu Glu
                        180                 185                 190
        Val Ile Lys Gly Gly Arg His Leu Ile Phe Cys His Ser Lys Lys Lys
                    195                 200                 205
        Cys Asp Glu Leu Ala Ala Lys Leu Val Ala Leu Gly Ile Asn Ala Val
                210                 215                 220
        Ala Tyr Tyr Arg Gly Leu Asp Val Ser Val Ile Pro Thr Ser Gly Asp
        225                 230                 235                 240
        Val Val Val Val Ala Thr Asp Ala Leu Met Thr Gly Tyr Thr Gly Asp
                        245                 250                 255
        Phe Asp Ser Val Ile Asp Cys Asn Thr Cys Val Thr Gln Thr Val Asp
                        260                 265                 270
        Phe Ser Leu Asp Pro Thr Phe Thr Ile Glu Thr Ile Thr Leu Pro Gln
                    275                 280                 285
        Asp Ala Val Ser Arg Thr Gln Arg Arg Gly Arg Thr Gly Arg Gly Lys
                290                 295                 300
        Pro Gly Ile Tyr Arg Phe Val Ala Pro Gly Glu Arg Pro Ser Gly Met
        305                 310                 315                 320
        Phe Asp Ser Ser Val Leu Cys Glu Cys Tyr Asp Ala Gly Cys Ala Trp
                        325                 330                 335
        Tyr Glu Leu Thr Pro Ala Glu Thr Thr Val Arg Leu Arg Ala Tyr Met
                        340                 345                 350
        Asn Thr Pro Gly Leu Pro Val Cys Gln Asp His Leu Glu Phe Trp Glu
                    355                 360                 365
        Gly Val Phe Thr Gly Leu Thr His Ile Asp Ala His Phe Leu Ser Gln
                370                 375                 380
        Thr Lys Gln Ser Gly Glu Asn Leu Pro Tyr Leu Val Ala Tyr Gln Ala
        385                 390                 395                 400
        Thr Val Cys Ala Arg Ala Gln Ala Pro Pro Ser Trp Asp Gln Met
                        405                 410                 415
        Trp Lys Cys Leu Ile Arg Leu Lys Pro Thr Leu His Gly Pro Thr Pro
                        420                 425                 430
        Leu Leu Tyr Arg Leu Gly Ala Val Gln Asn Glu Ile Thr Leu Thr His
                    435                 440                 445
        Pro Val Thr Lys Tyr Ile Met Thr Cys Met Ser Ala Asp Leu Glu Val
                450                 455                 460
        Val Thr Ser
        465

<210> SEQ ID NO 21
```

<211> LENGTH: 495
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttact                                                      495
```

<210> SEQ ID NO 22
<211> LENGTH: 165
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe Gln
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr
                165
```

<210> SEQ ID NO 23
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
gctgttgact ttatcccggt tgaaaatctc gagactacta tgcgttctcc ggttttcact      60
gacaactctt ctgttccgca cccgaacatc gaagaagttg ctctgtcgac tactggtgaa     120
atcccgttct acggtaaagc tatcccgctc gaggttatca aggtggtcg tcacctgatt      180
ttctgccact ctaaaaaaaa atgcgacgaa ctggctgcta agcttgttgc tctgggtatc     240
aacgctgttg cttactaccg tggtctggac gtttctgtta cccgacttc tggtgacgtt      300
gttgttgtgg ccactgacgc tctgatgact ggttacactg gtgacttcga ctctgttatc     360
gattgcaaca cttgc                                                     375
```

<210> SEQ ID NO 24
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ala Val Asp Phe Ile Pro Val Glu Asn Leu Glu Thr Thr Met Arg Ser
1               5                   10                  15

Pro Val Phe Thr Asp Asn Ser Ser Val Pro His Pro Asn Ile Glu Glu
            20                  25                  30

Val Ala Leu Ser Thr Thr Gly Glu Ile Pro Phe Tyr Gly Lys Ala Ile
        35                  40                  45

Pro Leu Glu Val Ile Lys Gly Gly Arg His Leu Ile Phe Cys His Ser
    50                  55                  60

Lys Lys Lys Cys Asp Glu Leu Ala Ala Lys Leu Val Ala Leu Gly Ile
65                  70                  75                  80

Asn Ala Val Ala Tyr Tyr Arg Gly Leu Asp Val Ser Val Ile Pro Thr
                85                  90                  95

Ser Gly Asp Val Val Val Ala Thr Asp Ala Leu Met Thr Gly Tyr
            100                 105                 110

Thr Gly Asp Phe Asp Ser Val Ile Asp Cys Asn Thr Cys
        115                 120                 125
```

<210> SEQ ID NO 25
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gctgttgact ttatcccggt tgaaaatctc gagactacta tgcgttctcc ggttttcact      60
gacaactctt ctttcgatag ctctgttctg tgtgagtgtt atgacgcggg ttgcgcgtgg     120
tacgaactga ctccggctga aactactgta cgcctgcgtg catacatgaa tacgccgggt     180
ctgccggtgt gtcaagacca cctggaattt gggaaggtg tctttactgg cctgacccat      240
atcgacgcac actttctgtc ccagactaaa cagtctggtg aaaacctgcc gtacctggtg     300
gcgtatcaag ccactgtgtg cgcccgtgcg caggcgccgc accgagctg ggaccaaatg      360
tggaagtgcc tgatccgtct gaaaccgacc ctgcacggtc cgacgccact gctgtaccgc     420
ctgggtgcag tgcagaacga aatcacgctg acgcacccgg tcactaaata cattatgact     480
```
tgcatgagcg cagacctgga agtggtgact tcc         513

<210> SEQ ID NO 26
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Val Asp Phe Ile Pro Val Glu Asn Leu Glu Thr Thr Met Arg Ser
1               5                   10                  15

Pro Val Phe Thr Asp Asn Ser Ser Phe Asp Ser Ser Val Leu Cys Glu
            20                  25                  30

Cys Tyr Asp Ala Gly Cys Ala Trp Tyr Glu Leu Thr Pro Ala Glu Thr
        35                  40                  45

Thr Val Arg Leu Arg Ala Tyr Met Asn Thr Pro Gly Leu Pro Val Cys
    50                  55                  60

Gln Asp His Leu Glu Phe Trp Glu Gly Val Phe Thr Gly Leu Thr His
65                  70                  75                  80

Ile Asp Ala His Phe Leu Ser Gln Thr Lys Gln Ser Gly Glu Asn Leu
                85                  90                  95

Pro Tyr Leu Val Ala Tyr Gln Ala Thr Val Cys Ala Arg Ala Gln Ala
            100                 105                 110

Pro Pro Pro Ser Trp Asp Gln Met Trp Lys Cys Leu Ile Arg Leu Lys
        115                 120                 125

Pro Thr Leu His Gly Pro Thr Pro Leu Leu Tyr Arg Leu Gly Ala Val
    130                 135                 140

Gln Asn Glu Ile Thr Leu Thr His Pro Val Thr Lys Tyr Ile Met Thr
145                 150                 155                 160

Cys Met Ser Ala Asp Leu Glu Val Val Thr Ser
                165                 170

<210> SEQ ID NO 27
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gctgttgact ttatcccggt tgaaaatctc gagactacta tgcgttctcc ggttttcact      60
gacaactctt ctgttccgca cccgaacatc gaagaagttg ctctgtcgac tactggtgaa     120
atcccgttct acggtaaagc tatcccgctc gaggttatca aggtggtcg tcacctgatt      180 ttctgccact ctaaaaaaaa atgcgacgaa ctggctgcta agcttgttgc tctgggtatc     240
aacgctgttg cttactaccg tggtctggac gtttctgtta tcccgacttc tggtgacgtt     300
gttgttgtgg ccactgacgc tctgatgact ggttacactg gtgacttcga ctctgttatc     360
gattgcaaca cttgcgttac tcagaccgta gattttagcc tggacccgac tttcactatc     420
gaaacgatca ccctgccgca ggatgcagtt tcccgtaccc agcgtcgtgg ccgtaccggt     480
cgcggcaaac cgggtattta ccgtttcgtg gcgccgggcg agcgtccatc cggtatgttc     540
gatagctctg ttctgtgtga gtgttatgac gcgggttgcg cgtggtacga actgactccg     600
gctgaaacta ctgtacgcct gcgtgcatac atgaatacgc cgggtctgcc ggtgtgtcaa     660

```
gaccacctgg aattttggga aggtgtcttt actggcctga cccatatcga cgcacacttt    720
ctgtcccaga ctaaacagtc tggtgaaaac ctgccgtacc tggtggcgta tcaagccact    780
gtgtgcgccc gtgcgcaggc gccgccaccg agctgggacc aaatgtggaa gtgcctgatc    840
cgtctgaaac cgaccctgca cggtccgacg ccactgctgt accgcctggg tgcagtgcag    900
aacgaaatca cgctgacgca cccggtcact aaatacatta tgacttgcat gagcgcagac    960
ctggaagtgg tgacttcc                                                  978
```

<210> SEQ ID NO 28
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 28

```
Ala Val Asp Phe Ile Pro Val Glu Asn Leu Glu Thr Thr Met Arg Ser
1               5                   10                  15

Pro Val Phe Thr Asp Asn Ser Ser Val Pro His Pro Asn Ile Glu Glu
            20                  25                  30

Val Ala Leu Ser Thr Thr Gly Glu Ile Pro Phe Tyr Gly Lys Ala Ile
        35                  40                  45

Pro Leu Glu Val Ile Lys Gly Gly Arg His Leu Ile Phe Cys His Ser
    50                  55                  60

Lys Lys Lys Cys Asp Glu Leu Ala Ala Lys Leu Val Ala Leu Gly Ile
65                  70                  75                  80

Asn Ala Val Ala Tyr Tyr Arg Gly Leu Asp Val Ser Val Ile Pro Thr
                85                  90                  95

Ser Gly Asp Val Val Val Ala Thr Asp Ala Leu Met Thr Gly Tyr
            100                 105                 110

Thr Gly Asp Phe Asp Ser Val Ile Asp Cys Asn Thr Cys Val Thr Gln
            115                 120                 125

Thr Val Asp Phe Ser Leu Asp Pro Thr Phe Thr Ile Glu Thr Ile Thr
130                 135                 140

Leu Pro Gln Asp Ala Val Ser Arg Thr Gln Arg Gly Arg Thr Gly
145                 150                 155                 160

Arg Gly Lys Pro Gly Ile Tyr Arg Phe Val Ala Pro Gly Glu Arg Pro
                165                 170                 175

Ser Gly Met Phe Asp Ser Ser Val Leu Cys Glu Cys Tyr Asp Ala Gly
            180                 185                 190

Cys Ala Trp Tyr Glu Leu Thr Pro Ala Glu Thr Thr Val Arg Leu Arg
        195                 200                 205

Ala Tyr Met Asn Thr Pro Gly Leu Pro Val Cys Gln Asp His Leu Glu
    210                 215                 220

Phe Trp Glu Gly Val Phe Thr Gly Leu Thr His Ile Asp Ala His Phe
225                 230                 235                 240

Leu Ser Gln Thr Lys Gln Ser Gly Glu Asn Leu Pro Tyr Leu Val Ala
                245                 250                 255

Tyr Gln Ala Thr Val Cys Ala Arg Ala Gln Ala Pro Pro Ser Trp
            260                 265                 270

Asp Gln Met Trp Lys Cys Leu Ile Arg Leu Lys Pro Thr Leu His Gly
        275                 280                 285

Pro Thr Pro Leu Leu Tyr Arg Leu Gly Ala Val Gln Asn Glu Ile Thr
    290                 295                 300
```

Leu Thr His Pro Val Thr Lys Tyr Ile Met Thr Cys Met Ser Ala Asp
305                 310                 315                 320

Leu Glu Val Val Thr Ser
            325

<210> SEQ ID NO 29
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gctgttgact ttatcccggt tgaaaatctc gagactacta tgcgttctcc ggttttcact      60
gacaactctt ctgttccgca cccgaacatc gaagaagttg ctctgtcgac tactggtgaa    120
atcccgttct acggtaaagc tatcccgctc gaggttatca aggtggtcg tcacctgatt     180 ttctgccact ctaaaaaaaa atgcgacgaa ctggctgcta agcttgttgc tctgggtatc    240
aacgctgttg cttactaccg tggtctggac gtttctgtta cccgacttc tggtgacgtt     300 gttgttgtgg ccactgacgc tctgatgact ggttacactg tgacttcga ctctgttatc     360 gattgcaaca cttgcgttac tcagaccgta gattttagcc tggacccgac tttcactatc    420
gaaacgatca ccctgccgca ggatgcagtt tcccgtaccc agcgtcgtgg ccgtaccggt    480
cgcggcaaac cgggtattta ccgtttcgtg gcgccgggcg agcgtccatc cggt          534

<210> SEQ ID NO 30
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Val Asp Phe Ile Pro Val Glu Asn Leu Glu Thr Thr Met Arg Ser
1               5                   10                  15

Pro Val Phe Thr Asp Asn Ser Ser Val Pro His Pro Asn Ile Glu Glu
            20                  25                  30

Val Ala Leu Ser Thr Thr Gly Glu Ile Pro Phe Tyr Gly Lys Ala Ile
        35                  40                  45

Pro Leu Glu Val Ile Lys Gly Gly Arg His Leu Ile Phe Cys His Ser
    50                  55                  60

Lys Lys Lys Cys Asp Glu Leu Ala Ala Lys Leu Val Ala Leu Gly Ile
65                  70                  75                  80

Asn Ala Val Ala Tyr Tyr Arg Gly Leu Asp Val Ser Val Ile Pro Thr
                85                  90                  95

Ser Gly Asp Val Val Val Ala Thr Asp Ala Leu Met Thr Gly Tyr
            100                 105                 110

Thr Gly Asp Phe Asp Ser Val Ile Asp Cys Asn Thr Cys Val Thr Gln
        115                 120                 125

Thr Val Asp Phe Ser Leu Asp Pro Thr Phe Thr Ile Glu Thr Ile Thr
    130                 135                 140

Leu Pro Gln Asp Ala Val Ser Arg Thr Gln Arg Arg Gly Arg Thr Gly
145                 150                 155                 160

Arg Gly Lys Pro Gly Ile Tyr Arg Phe Val Ala Pro Gly Glu Arg Pro
                165                 170                 175

Ser Gly

<210> SEQ ID NO 31
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

| | | | | | |
|---|---|---|---|---|---|
| gctgttgact | ttatcccggt | tgaaaatctc | gagactacta | tgcgttctcc | ggttttcact | 60 |
| gacaactctt | ctccgccggt | tgttccgcag | tctttccagg | ttgctcacct | gcatgctccg | 120 |
| actggttctg | gtaaatctac | taaagttcca | gctgcttacg | ctgctcaggg | ttacaaagtt | 180 |
| ctggttctga | acccgtctgt | tgctgctact | ctgggtttcg | gcgcctacat | gtctaaagct | 240 |
| cacggtatcg | acccgaacat | tcgtactggt | gtacgtacta | tcactactgg | ttctccgatc | 300 |
| acttactcta | cttacggtaa | attcctggct | gacggtggtt | gctctggtgg | tgcttacgat | 360 |
| atcatcatct | gcgacgaatg | ccactctact | gacgctactt | ctatcctggg | tatcggtacc | 420 |
| gttctggacc | aggctgaaac | tgcaggtgct | cgtctggttg | ttctggctac | tgctactccg | 480 |
| ccgggttctg | ttactgttcc | gcacccgaac | atcgaagaag | ttgctctgtc | gactactggt | 540 |
| gaaatcccgt | tctacggtaa | agctatcccg | ctcgaggtta | tcaaaggtgg | tcgtcacctg | 600 |
| attttctgcc | actctaaaaa | aaaatgcgac | gaactggctg | ctaagcttgt | tgctctgggt | 660 |
| atcaacgctg | ttgcttacta | ccgtggtctg | gacgtttctg | ttatcccgac | ttctggtgac | 720 |
| gttgttgttg | tggccactga | cgctctgatg | actggttaca | ctggtgactt | cgactctgtt | 780 |
| atcgattgca | acacttgcgt | tactcagacc | gtagatttta | gcctggaccc | gactttcact | 840 |
| atcgaaacga | tcaccctgcc | gcaggatgca | gtttcccgta | cccagcgtcg | tggccgtacc | 900 |
| ggtcgcggca | aaccgggtat | ttaccgtttc | gtggcgccgg | cgagcgtcc | atccggt | 957 |

<210> SEQ ID NO 32
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His

```
            115                 120                 125
Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly
305                 310                 315

<210> SEQ ID NO 33
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gctgttgact ttatcccggt tgaaaatctc gagactacta tgcgttctcc ggttttcact      60
gacaactctt ctgttactca gaccgtagat tttagcctgg acccgacttt cactatcgaa     120
acgatcaccc tgccgcagga tgcagtttcc cgtacccagc gtcgtggccg taccggtcgc     180
ggcaaaccgg gtatttaccg tttcgtggcg ccgggcgagc gtccatccgg tatgttcgat     240
agctctgttc tgtgtgagtg ttatgacgcg ggttgcgcgt ggtacgaact gactccggct     300
gaaactactg tacgcctgcg tgcatacatg aatacgccgg gtctgccggt gtgtcaagac     360
cacctggaat tgggaaggt gtctttact ggcctgaccc atatcgacgc acactttctg     420
tcccagacta acagtctgg tgaaaacctg ccgtacctgg tggcgtatca agccactgtg     480
tgcgcccgtg cgcaggcgcc gccaccgagc tgggaccaaa tgtggaagtg cctgatccgt     540
ctgaaaccga ccctgcacgg tccgacgcca ctgctgtacc gcctgggtgc agtgcagaac     600
gaaatcacgc tgacgcaccc ggtcactaaa tacattatga cttgcatgag cgcagacctg     660
gaagtggtga cttcc                                                     675

<210> SEQ ID NO 34
<211> LENGTH: 225
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 34

Ala Val Asp Phe Ile Pro Val Glu Asn Leu Glu Thr Thr Met Arg Ser
1               5                   10                  15

Pro Val Phe Thr Asp Asn Ser Ser Val Thr Gln Thr Val Asp Phe Ser
            20                  25                  30

Leu Asp Pro Thr Phe Thr Ile Glu Thr Ile Thr Leu Pro Gln Asp Ala
        35                  40                  45

Val Ser Arg Thr Gln Arg Arg Gly Arg Thr Gly Arg Gly Lys Pro Gly
    50                  55                  60

Ile Tyr Arg Phe Val Ala Pro Gly Glu Arg Pro Ser Gly Met Phe Asp
65              70                  75                  80

Ser Ser Val Leu Cys Glu Cys Tyr Asp Ala Gly Cys Ala Trp Tyr Glu
                85                  90                  95

Leu Thr Pro Ala Glu Thr Thr Val Arg Leu Arg Ala Tyr Met Asn Thr
            100                 105                 110

Pro Gly Leu Pro Val Cys Gln Asp His Leu Glu Phe Trp Glu Gly Val
        115                 120                 125

Phe Thr Gly Leu Thr His Ile Asp Ala His Phe Leu Ser Gln Thr Lys
    130                 135                 140

Gln Ser Gly Glu Asn Leu Pro Tyr Leu Val Ala Tyr Gln Ala Thr Val
145                 150                 155                 160

Cys Ala Arg Ala Gln Ala Pro Pro Ser Trp Asp Gln Met Trp Lys
                165                 170                 175

Cys Leu Ile Arg Leu Lys Pro Thr Leu His Gly Pro Thr Pro Leu Leu
            180                 185                 190

Tyr Arg Leu Gly Ala Val Gln Asn Glu Ile Thr Leu Thr His Pro Val
        195                 200                 205

Thr Lys Tyr Ile Met Thr Cys Met Ser Ala Asp Leu Glu Val Val Thr
    210                 215                 220

Ser
225

<210> SEQ ID NO 35
<211> LENGTH: 1401
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
gctgttgact ttatcccggt tgaaaatctc gagactacta tgcgttctcc ggttttcact      60
gacaactctt ctccgccggt tgttccgcag tcttttcagg ttgctcacct gcatgctccg     120
actggttctg gtaactctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540

-continued

```
gaaatcccgt tctacggtaa agctatcccg ctcgaggtta tcaaggtggt tcgtcacctg    600
attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg gcgagcgtcc atccggtatg    960
ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcaccccggtc actaaataca ttatgacttg catgagcgca   1380
gacctggaag tggtgacttc c                                             1401
```

<210> SEQ ID NO 36
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Asn Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205
```

```
Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr Ser
465

<210> SEQ ID NO 37
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaagcgac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
```

```
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                             1401
```

<210> SEQ ID NO 38
<211> LENGTH: 467
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 38

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ala Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190
```

```
Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
450                 455                 460

Val Thr Ser
465

<210> SEQ ID NO 39
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctga aaagttcca gctgcttacg ctgctcaggg ttacaaagtt     180
ctggttctga acccgtctgt tgctgctact ctgggtttcg cgcctacat gtctaaagct     240 cacggtatcg acccgaacat cgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
```

```
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaggtgg tcgtcacctg     600
attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg gcgagcgtcc atccggtatg    960
ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                             1401
```

<210> SEQ ID NO 40
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Glu Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
```

```
                    180                 185                 190
Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
            210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
        450                 455                 460

Val Thr Ser
465

<210> SEQ ID NO 41
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg taaatctac taagttcca gctgcttacg ctgctcaggg ttacaaagtt      180
ctggttctga accgtctgt tgctgctact ctgggtttcg gcgccagcat gtctaaagct      240
cacggtatcg acccgaacat tcgtactggt gtacgtacta tcactactgg ttctccgatc     300
acttactcta cttacggtaa attcctggct gacggtggtt gctctggtgg tgcttacgat     360
```

```
atcatcatct gcgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt ctacggtaa agctatcccg ctcgaggtta tcaaaggtgg tcgtcacctg     600
attttctgcc actctaaaaa aaaatgcgac gaactggctg ctaagcttgt tgctctgggt    660
atcaacgctg ttgcttacta ccgtggtctg gacgtttctg ttatcccgac ttctggtgac   720
gttgttgttg tggccactga cgctctgatg actggttaca ctggtgactt cgactctgtt   780
atcgattgca acacttgcgt tactcagacc gtagatttta gcctggaccc gactttcact   840
atcgaaacga tcaccctgcc gcaggatgca gtttcccgta cccagcgtcg tggccgtacc   900
ggtcgcggca aacgggtat ttaccgtttc gtggcgccgg cgagcgtcc atccggtatg     960 ttcgatagct ctgttctgtg tgagtgttat gacgcgggtt gcgcgtggta cgaactgact   1020
ccggctgaaa ctactgtacg cctgcgtgca tacatgaata cgcccgggtct gccggtgtgt   1080 caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                              1401
```

<210> SEQ ID NO 42
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
        50                  55                  60

Pro Ser Val Ala Ala Thr Leu Gly Phe Gly Ala Ser Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175
```

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 43
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct     240
cacggtatcg acccgaacat tcgtactggt gtacgtacta tcactactgg ttctccgatc     300

```
acttactcta cttacggtaa attcctggct gacggtggtt gctctggtgg tgcttacgat    360
atcatcatct gcaacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaggtgg tcgtcacctg    600 attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg gcgagcgtcc atccggtatg    960
ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg aagtgcctg   1260 atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                              1401
```

<210> SEQ ID NO 44
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asn Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

-continued

```
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
            180                 185                 190
Val Ile Lys Gly Gly Arg His Leu Ile Phe Cys His Ser Lys Lys Lys
        195                 200                 205
Cys Asp Glu Leu Ala Ala Lys Leu Val Ala Leu Gly Ile Asn Ala Val
    210                 215                 220
Ala Tyr Tyr Arg Gly Leu Asp Val Ser Val Ile Pro Thr Ser Gly Asp
225                 230                 235                 240
Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
            275                 280                 285
Asp Ala Val Ser Arg Thr Gln Arg Arg Gly Arg Thr Gly Arg Gly Lys
        290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
            355                 360                 365
Gly Val Phe Thr Gly Leu Thr His Ile Asp Ala His Phe Leu Ser Gln
        370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Ser Trp Asp Gln Met
                405                 410                 415
Trp Lys Cys Leu Ile Arg Leu Lys Pro Thr Leu His Gly Pro Thr Pro
                420                 425                 430
Leu Leu Tyr Arg Leu Gly Ala Val Gln Asn Glu Ile Thr Leu Thr His
            435                 440                 445
Pro Val Thr Lys Tyr Ile Met Thr Cys Met Ser Ala Asp Leu Glu Val
        450                 455                 460
Val Thr Ser
465
```

<210> SEQ ID NO 45
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
```

-continued

```
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgaccagtg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt ctctacggta agctatcccg ctcgaggtta tcaaaggtgg tcgtcacctg    600
attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg cgagcgtcc atccggtatg    960 ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa acctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                             1401
```

<210> SEQ ID NO 46
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Gln Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
```

```
145                 150                 155                 160
Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr Ser
465

<210> SEQ ID NO 47
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
```

```
ctggttctga acccgtctgt tgctgctact ctgggtttcg gcgcctacat gtctaaagct    240
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgacgaaag ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttctgcc actctaaaaa aaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg cgagcgtcc atccggtatg    960 ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg gaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcaccccggtc actaaataca ttatgacttg catgagcgca   1380
gacctggaag tggtgacttc c                                              1401
```

<210> SEQ ID NO 48
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
    130                 135                 140
```

Ala Glu Thr Ala Gly Ala Arg Leu Val Val Leu Ala Thr Ala Pro
145                 150                 155                 160

Pro Gly Ser Val Thr Val Pro His Pro Asn Ile Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 49
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gctgttgact ttatcccggt tgaaaatctc gagactacta tgcgttctcc ggttttcact      60
gacaactctt ctccgccggt tgttccgcag tctttccagg ttgctcacct gcatgctccg     120

```
actggttctg gtaaatctac taaagttcca gctgcttacg ctgctcaggg ttacaaagtt      180
ctggttctga acccgtctgt tgctgctact ctgggtttcg gcgcctacat gtctaaagct      240
cacggtatcg acccgaacat tcgtactggt gtacgtacta tcactactgg ttctccgatc      300
acttactcta cttacggtaa attcctggct gacggtggtt gctctggtgg tgcttacgat      360
atcatcatct gcgacgaatg cgcctctact gacgctactt ctatcctggg tatcggtacc      420
gttctggacc aggctgaaac tgcaggtgct cgtctggttg ttctggctac tgctactccg      480
ccgggttctg ttactgttcc gcacccgaac atcgaagaag ttgctctgtc gactactggt      540
gaaatcccgt tctacggtaa agctatcccg ctcgaggtta tcaaaggtgg tcgtcacctg      600
attttctgcc actctaaaaa aaaatgcgac gaactggctg ctaagcttgt tgctctgggt      660
atcaacgctg ttgcttacta ccgtggtctg gacgtttctg ttatcccgac ttctggtgac      720
gttgttgttg tggccactga cgctctgatg actggttaca ctggtgactt cgactctgtt      780
atcgattgca acacttgcgt tactcagacc gtagatttta gcctggaccc gactttcact      840
atcgaaacga tcaccctgcc gcaggatgca gtttcccgta cccagcgtcg tggccgtacc      900
ggtcgcggca aaccgggtat ttaccgtttc gtggcgccgg cgagcgtcc atccggtatg      960 ttcgatagct ctgttctgtg tgagtgttat gacgcgggtt gcgcgtggta cgaactgact     1020
ccggctgaaa ctactgtacg cctgcgtgca tacatgaata cgcccgggtct gccggtgtgt     1080 caagaccacc tggaattttg ggaaggtgtc tttactggcc tgacccatat cgacgcacac     1140
tttctgtccc agactaaaca gtctggtgaa aacctgccgt acctggtggc gtatcaagcc     1200
actgtgtgcg cccgtgcgca ggcgccgcca ccgagctggg accaaatgtg gaagtgcctg     1260
atccgtctga aaccgaccct gcacggtccg acgccactgc tgtaccgcct gggtgcagtg     1320
cagaacgaaa tcacgctgac gcaccccggtc actaaataca ttatgacttg catgagcgca     1380
gacctggaag tggtgacttc c                                                1401
```

<210> SEQ ID NO 50
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys Ala
        115                 120                 125
```

```
Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
450                 455                 460

Val Thr Ser
465

<210> SEQ ID NO 51
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gctgttgact ttatcccggt tgaaaatctc gagactacta tgcgttctcc ggttttcact      60
```

```
gacaactctt ctccgccggt tgttccgcag tctttccagg ttgctcacct gcatgctccg    120
actggttctg gtaaatctac taaagttcca gctgcttacg ctgctcaggg ttacaaagtt    180
ctggttctga accgtctgt tgctgctact ctgggtttcg gcgcctacat gtctaaagct    240
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttctgcc actctaaaaa aaaaagcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagattta gcctggaccc gactttcact    840
atcgaaacga tcacccctgcc gcaggatgca gtttcccgta cccagcgtcg tggccgtacc    900
ggtcgcggca aaccgggtat ttaccgtttc gtggcgccgg cgagcgtcc atccggtatg    960 ttcgatagct ctgttctgtg tgagtgttat gacgcgggtt gcgcgtggta cgaactgact   1020
ccggctgaaa ctactgtacg cctgcgtgca tacatgaata cgcccgggtct gccggtgtgt   1080 caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg aagtgcctg   1260 atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                              1401

<210> SEQ ID NO 52
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
```

```
            115                 120                 125
Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Ser Asp Glu Leu Ala Ala Lys Leu Val Ala Leu Gly Ile Asn Ala Val
            210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
            290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr Ser
465

<210> SEQ ID NO 53
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
```

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttacg gtggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccccggtc actaaataca ttatgacttg catgagcgca    1380
gacctggaag tggtgacttc c                                              1401
```

<210> SEQ ID NO 54
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110
```

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Gly Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 55
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide -continued

```
<400> SEQUENCE: 55
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600 atttttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccatcgtcg tggccgtacc     900
ggtcgcggca aaccgggtat ttaccgtttc gtggcgccgg cgagcgtcc atccggtatg      960 ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                             1401

<210> SEQ ID NO 56
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95
```

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr His Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 57
<211> LENGTH: 1401
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 57

```
gctgttgact ttatcccggt tgaaaatctc gagactacta tgcgttctcc ggttttcact        60
gacaactctt ctccgccggt tgttccgcag tctttccagg ttgctcacct gcatgctccg       120
actggttctg gtaaatctac taaagttcca gctgcttacg ctgctcaggg ttacaaagtt       180
ctggttctga acccgtctgt tgctgctact ctgggtttcg gcgcctacat gtctaaagct       240
cacggtatcg acccgaacat tcgtactggt gtacgtacta tcactactgg ttctccgatc       300
acttactcta cttacggtaa attcctggct gacggtggtt gctctggtgg tgcttacgat       360
atcatcatct gcgacgaatg ccactctact gacgctactt ctatcctggg tatcggtacc       420
gttctggacc aggctgaaac tgcaggtgct cgtctggttg ttctggctac tgctactccg       480
ccgggttctg ttactgttcc gcacccgaac atcgaagaag ttgctctgtc gactactggt       540
gaaatcccgt tctacggtaa agctatcccg ctcgaggtta tcaaaggtgg tcgtcacctg       600
attttctgcc actctaaaaa aaaatgcgac gaactggctg ctaagcttgt tgctctgggt       660
atcaacgctg ttgcttacta ccgtggtctg gacgtttctg ttatcccgac ttctggtgac       720
gttgttgttg tggccactga cgctctgatg actggttaca ctggtgactt cgactctgtt       780
atcgattgca acacttgcgt tactcagacc gtagatttta gcctggaccc gactttcact       840
atcgaaacga tcaccctgcc gcaggatgca gtttcccgta cccagcgtcg tggcgcgacc       900
ggtcgcggca aaccgggtat ttaccgtttc gtggcgccgg cgagcgtcc atccggtatg        960
ttcgatagct ctgttctgtg tgagtgttat gacgcgggtt gcgcgtggta cgaactgact      1020
ccggctgaaa ctactgtacg cctgcgtgca tacatgaata cgccgggtct gccggtgtgt      1080
caagaccacc tggaattttg ggaaggtgtc tttactggcc tgacccatat cgacgcacac      1140
tttctgtccc agactaaaca gtctggtgaa aacctgccgt acctggtggc gtatcaagcc      1200
actgtgtgcg cccgtgcgca ggcgccgcca ccgagctggg accaaatgtg gaagtgcctg      1260
atccgtctga aaccgaccct gcacggtccg acgccactgc tgtaccgcct gggtgcagtg      1320
cagaacgaaa tcacgctgac gcaccccggtc actaaataca ttatgacttg catgagcgca      1380
gacctggaag tggtgacttc c                                                1401
```

<210> SEQ ID NO 58
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
```

```
                        85                  90                  95
Gly Ser Pro Ile Thr Tyr Ser Thr Tyr Gly Lys Phe Leu Ala Asp Gly
                100                 105                 110
Gly Cys Ser Gly Gly Ala Tyr Asp Ile Ile Cys Asp Glu Cys His
            115                 120                 125
Ser Thr Asp Ala Thr Ser Ile Leu Gly Ile Gly Thr Val Leu Asp Gln
        130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
                180                 185                 190
Val Ile Lys Gly Gly Arg His Leu Ile Phe Cys His Ser Lys Lys Lys
                195                 200                 205
Cys Asp Glu Leu Ala Ala Lys Leu Val Ala Leu Gly Ile Asn Ala Val
                210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
                275                 280                 285
Asp Ala Val Ser Arg Thr Gln Arg Arg Gly Ala Thr Gly Arg Gly Lys
                290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
                355                 360                 365
Gly Val Phe Thr Gly Leu Thr His Ile Asp Ala His Phe Leu Ser Gln
                370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Pro Ser Trp Asp Gln Met
                405                 410                 415
Trp Lys Cys Leu Ile Arg Leu Lys Pro Thr Leu His Gly Pro Thr Pro
                420                 425                 430
Leu Leu Tyr Arg Leu Gly Ala Val Gln Asn Glu Ile Thr Leu Thr His
                435                 440                 445
Pro Val Thr Lys Tyr Ile Met Thr Cys Met Ser Ala Asp Leu Glu Val
                450                 455                 460
Val Thr Ser
465

<210> SEQ ID NO 59
<211> LENGTH: 1401
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 59
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactc tatcctggg tatcggtacc      420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg acgtttctg ttatcccgac ttctggtgac      720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttccgta cccagcgtcg tggccgtacc       900
ggtaaaggca aaccgggtat taccgtttc gtggcgccgg cgagcgtcc atccggtatg        960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401

<210> SEQ ID NO 60
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80
```

His Gly Ile Asp Pro Asn Ile Arg Thr Gly Val Arg Thr Ile Thr Thr
            85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys
            195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Lys Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
    435                 440                 445

Pro Val Thr Lys Tyr Ile Met Thr Cys Met Ser Ala Asp Leu Glu Val
450                 455                 460

Val Thr Ser
465

<210> SEQ ID NO 61
<211> LENGTH: 1401

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggta gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 62
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60
```

```
Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
             85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Ser Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr Ser
465
```

<210> SEQ ID NO 63
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
gctgttgact ttatcccggt tgaaaatctc gagactacta tgcgttctcc ggttttcact       60
gacaactctt ctccgccggt tgttccgcag tctttccagg ttgctcacct gcatgctccg      120
actggttctg gtaaatctac taaagttcca gctgcttacg ctgctcaggg ttacaaagtt      180
ctggttctga acccgtctgt tgctgctact ctgggtttcg gcgcctacat gtctaaagct      240
cacggtatcg acccgaacat tcgtactggt gtacgtacta tcactactgg ttctccgatc      300
acttactcta cttacggtaa attcctggct gacggtggtt gctctggtgg tgcttacgat      360
atcatcatct gcgacgaatg ccactctact gacgctactt ctatcctggg tatcggtacc      420
gttctggacc aggctgaaac tgcaggtgct cgtctggttg ttctggctac tgctactccg      480
ccgggttctg ttactgttcc gcacccgaac atcgaagaag ttgctctgtc gactactggt      540
gaaatcccgt tctacggtaa agctatcccg ctcgaggtta tcaaaggtgg tcgtcacctg      600
attttctgcc actctaaaaa aaaatgcgac gaactggctg ctaagcttgt tgctctgggt      660
atcaacgctt tgcttactac cgtggtctg acgtttctg ttatcccgac ttctggtgac      720
gttgttgttg tggccactga cgctctgatg actggttaca ctggtgactt cgactctgtt      780
atcgattgca acacttgcgt tactcagacc gtagatttta gcctggaccc gacttttcact      840
atcgaaacga tcaccctgcc gcaggatgca gtttcccgta cccagcgtcg tggccgtacc      900
ggtcgcggca aaccgggtat ttaccgtttc gtggcgccgg cgagcgtcc atccggtatg      960
ttcgatagct ctgttctgtg tgagtgttat gacgcgggtt gcgcggcgta cgaactgact     1020
ccggctgaaa ctactgtacg cctgcgtgca tacatgaata cgccgggtct gccggtgtgt     1080
caagaccacc tggaattttg ggaaggtgtc tttactggcc tgacccatat cgacgcacac     1140
tttctgtccc agactaaaca gtctggtgaa aacctgccgt acctggtggc gtatcaagcc     1200
actgtgtgcg cccgtgcgca ggcgccgcca ccgagctggg accaaatgtg gaagtgcctg     1260
atccgtctga aaccgaccct gcacggtccg acgccactgc tgtaccgcct gggtgcagtg     1320
cagaacgaaa tcacgctgac gcacccggtc actaaataca ttatgacttg catgagcgca     1380
gacctggaag tggtgacttc c                                               1401
```

<210> SEQ ID NO 64
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
```

```
            50                  55                  60
Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                     85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys His
                115                 120                 125

Ser Thr Asp Ala Thr Ser Ile Leu Gly Ile Gly Thr Val Leu Asp Gln
                130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
                275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Ala
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
                370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
        450                 455                 460

Val Thr Ser
465
```

<210> SEQ ID NO 65
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtct    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccccggtc actaaataca ttatgacttg catgagcgca    1380
gacctggaag tggtgacttc c                                               1401
```

<210> SEQ ID NO 66
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

```
Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Ser Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460
```

<210> SEQ ID NO 67
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgactag catgagcgca    1380
gacctggaag tggtgacttc c                                                1401
```

<210> SEQ ID NO 68
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

-continued

```
Gln Val Ala His Leu His Ala Pro Thr Gly Ser Gly Lys Ser Thr Lys
             35                  40                  45
Val Pro Ala Ala Tyr Ala Ala Gln Gly Tyr Lys Val Leu Val Leu Asn
 50                  55                  60
Pro Ser Val Ala Ala Thr Leu Gly Phe Gly Ala Tyr Met Ser Lys Ala
 65                  70                  75                  80
His Gly Ile Asp Pro Asn Ile Arg Thr Gly Val Arg Thr Ile Thr Thr
                 85                  90                  95
Gly Ser Pro Ile Thr Tyr Ser Thr Tyr Gly Lys Phe Leu Ala Asp Gly
            100                 105                 110
Gly Cys Ser Gly Gly Ala Tyr Asp Ile Ile Ile Cys Asp Glu Cys His
        115                 120                 125
Ser Thr Asp Ala Thr Ser Ile Leu Gly Ile Gly Thr Val Leu Asp Gln
    130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
            180                 185                 190
Val Ile Lys Gly Gly Arg His Leu Ile Phe Cys His Ser Lys Lys Lys
        195                 200                 205
Cys Asp Glu Leu Ala Ala Lys Leu Val Ala Leu Gly Ile Asn Ala Val
    210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
            260                 265                 270
Phe Ser Leu Asp Pro Thr Phe Thr Ile Glu Thr Ile Thr Leu Pro Gln
        275                 280                 285
Asp Ala Val Ser Arg Thr Gln Arg Arg Gly Arg Thr Gly Arg Gly Lys
    290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
            340                 345                 350
Asn Thr Pro Gly Leu Pro Val Cys Gln Asp His Leu Glu Phe Trp Glu
        355                 360                 365
Gly Val Phe Thr Gly Leu Thr His Ile Asp Ala His Phe Leu Ser Gln
    370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Pro Ser Trp Asp Gln Met
                405                 410                 415
Trp Lys Cys Leu Ile Arg Leu Lys Pro Thr Leu His Gly Pro Thr Pro
            420                 425                 430
Leu Leu Tyr Arg Leu Gly Ala Val Gln Asn Glu Ile Thr Leu Thr His
        435                 440                 445
Pro Val Thr Lys Tyr Ile Met Thr Ser Met Ser Ala Asp Leu Glu Val
```

<210> SEQ ID NO 69
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg cgcctctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggcgcgacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccccggtc actaaataca ttatgacttg catgagcgca    1380
gacctggaag tggtgacttc c                                               1401
```

<210> SEQ ID NO 70
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Ala Val Asp Phe Ile Pro Val Glu Asn Leu Glu Thr Thr Met Arg Ser
 1               5                  10                  15

Pro Val Phe Thr Asp Asn Ser Ser Pro Pro Val Val Pro Gln Ser Phe
```

-continued

```
                20                  25                  30
        Gln Val Ala His Leu His Ala Pro Thr Gly Ser Gly Lys Ser Thr Lys
                 35                  40                  45
        Val Pro Ala Ala Tyr Ala Ala Gln Gly Tyr Lys Val Leu Val Leu Asn
         50                  55                  60
        Pro Ser Val Ala Ala Thr Leu Gly Phe Gly Ala Tyr Met Ser Lys Ala
         65                  70                  75                  80
        His Gly Ile Asp Pro Asn Ile Arg Thr Gly Val Arg Thr Ile Thr Thr
                         85                  90                  95
        Gly Ser Pro Ile Thr Tyr Ser Thr Tyr Gly Lys Phe Leu Ala Asp Gly
                        100                 105                 110
        Gly Cys Ser Gly Gly Ala Tyr Asp Ile Ile Cys Asp Glu Cys Ala
                    115                 120                 125
        Ser Thr Asp Ala Thr Ser Ile Leu Gly Ile Gly Thr Val Leu Asp Gln
                    130                 135                 140
        Ala Glu Thr Ala Gly Ala Arg Leu Val Val Leu Ala Thr Ala Thr Pro
        145                 150                 155                 160
        Pro Gly Ser Val Thr Val Pro His Pro Asn Ile Glu Glu Val Ala Leu
                        165                 170                 175
        Ser Thr Thr Gly Glu Ile Pro Phe Tyr Gly Lys Ala Ile Pro Leu Glu
                    180                 185                 190
        Val Ile Lys Gly Gly Arg His Leu Ile Phe Cys His Ser Lys Lys Lys
                    195                 200                 205
        Cys Asp Glu Leu Ala Ala Lys Leu Val Ala Leu Gly Ile Asn Ala Val
                210                 215                 220
        Ala Tyr Tyr Arg Gly Leu Asp Val Ser Val Ile Pro Thr Ser Gly Asp
        225                 230                 235                 240
        Val Val Val Val Ala Thr Asp Ala Leu Met Thr Gly Tyr Thr Gly Asp
                        245                 250                 255
        Phe Asp Ser Val Ile Asp Cys Asn Thr Cys Val Thr Gln Thr Val Asp
                        260                 265                 270
        Phe Ser Leu Asp Pro Thr Phe Thr Ile Glu Thr Ile Thr Leu Pro Gln
                    275                 280                 285
        Asp Ala Val Ser Arg Thr Gln Arg Arg Gly Ala Thr Gly Arg Gly Lys
                290                 295                 300
        Pro Gly Ile Tyr Arg Phe Val Ala Pro Gly Glu Arg Pro Ser Gly Met
        305                 310                 315                 320
        Phe Asp Ser Ser Val Leu Cys Glu Cys Tyr Asp Ala Gly Cys Ala Trp
                        325                 330                 335
        Tyr Glu Leu Thr Pro Ala Glu Thr Thr Val Arg Leu Arg Ala Tyr Met
                        340                 345                 350
        Asn Thr Pro Gly Leu Pro Val Cys Gln Asp His Leu Glu Phe Trp Glu
                    355                 360                 365
        Gly Val Phe Thr Gly Leu Thr His Ile Asp Ala His Phe Leu Ser Gln
                370                 375                 380
        Thr Lys Gln Ser Gly Glu Asn Leu Pro Tyr Leu Val Ala Tyr Gln Ala
        385                 390                 395                 400
        Thr Val Cys Ala Arg Ala Gln Ala Pro Pro Ser Trp Asp Gln Met
                        405                 410                 415
        Trp Lys Cys Leu Ile Arg Leu Lys Pro Thr Leu His Gly Pro Thr Pro
                    420                 425                 430
        Leu Leu Tyr Arg Leu Gly Ala Val Gln Asn Glu Ile Thr Leu Thr His
                435                 440                 445
```

Pro Val Thr Lys Tyr Ile Met Thr Cys Met Ser Ala Asp Leu Glu Val
    450                 455                 460

Val Thr Ser
465

<210> SEQ ID NO 71
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga cccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaaagcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca cacttgcgt tactcagacc gtagatttta gcctggaccc gactttcact     840
atcgaaacga tcacccctgcc gcaggatgca gtttcccgta cccagcgtcg tggccgtacc     900
ggtcgcggca aaccgggtat ttaccgtttc gtggcgccgg cgagcgtcc atccggtatg     960 ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080 caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401

<210> SEQ ID NO 72
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Val Asp Phe Ile Pro Val Glu Asn Leu Glu Thr Thr Met Arg Ser
1               5                   10                  15

-continued

```
Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Ser His
            115                 120                 125

Ser Thr Asp Ala Thr Ser Ile Leu Gly Ile Gly Thr Val Leu Asp Gln
 130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Ser Asp Glu Leu Ala Ala Lys Leu Val Ala Leu Gly Ile Asn Ala Val
 210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
 275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430
```

Leu Leu Tyr Arg Leu Gly Ala Val Gln Asn Glu Ile Thr Leu Thr His
    435                 440                 445

Pro Val Thr Lys Tyr Ile Met Thr Cys Met Ser Ala Asp Leu Glu Val
    450                 455                 460

Val Thr Ser
465

<210> SEQ ID NO 73
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taagttccag ctgcttacg ctgctcaggg ttacaaagtt      180
ctggttctga cccgtctgt tgctgctact ctgggtttcg cgcctacat gtctaaagct       240 cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgacgaaag ccactctact gacgctactt ctatcctggg tatcggtacc   420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg   600
attttctgcc actctaaaaa aaaatgcgac gaactggctg ctaagcttgt tgctctgggt   660
atcaacgctg ttgcttacta ccgtggtctg gacgtttctg ttatcccgac ttctggtgac   720
gttgttgttg tggccactga cgctctgatg actggttaca ctggtgactt cgactctgtt   780
atcgattgca acacttgcgt tactcagacc gtagatttta gcctggaccc gactttcact   840
atcgaaacga tcaccctgcc gcaggatgca gtttcccgta cccagcgtcg tggccgtacc   900
ggtcgcggca accgggtat ttaccgtttc gtggcgccgg cgagcgtcc atccggtatg      960 ttcgatagct ctgttctgtg tgagtgttat gacgcgggta gcgcgtggta cgaactgact    1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg    1320
cagaacgaaa tcacgctgac gcacccggtc actaaataca ttatgacttg catgagcgca   1380
gacctggaag tggtgacttc c                                               1401

<210> SEQ ID NO 74
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25              30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50              55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
    275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Ser Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
                370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
```

```
                420            425            430
Leu Leu Tyr Arg Leu Gly Ala Val Gln Asn Glu Ile Thr Leu Thr His
            435                440                445
Pro Val Thr Lys Tyr Ile Met Thr Cys Met Ser Ala Asp Leu Glu Val
    450                455                460
Val Thr Ser
465

<210> SEQ ID NO 75
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tgtactggt gtacgtacta tcactactgg ttctccgatc     300
acttactcta cttacggtaa attcctggct gacggtggtt gctctggtgg tgcttacgat     360
atcatcatct gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960 ttcgatagct ctgttctgtg tgagtgttat gacgcgggtt gcgcgtggta cgaactgact    1020
ccggctgaaa ctactgtacg cctgcgtgca tacatgaata cgcccggtct gccggtgagt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg aagtgcctg    1260 atccgtctga aaccgaccct gcacggtccg acgccactgc tgtaccgcct gggtgcagtg    1320
cagaacgaaa tcacgctgac gcaccggtc actaaataca ttatgacttg catgagcgca    1380
gacctggaag tggtgacttc c                                              1401

<210> SEQ ID NO 76
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 76

```
Ala Val Asp Phe Ile Pro Val Glu Asn Leu Glu Thr Thr Met Arg Ser
1               5                   10                  15
Pro Val Phe Thr Asp Asn Ser Ser Pro Val Val Pro Gln Ser Phe
            20                  25                  30
Gln Val Ala His Leu His Ala Pro Thr Gly Ser Gly Lys Ser Thr Lys
                35                  40                  45
Val Pro Ala Ala Tyr Ala Ala Gln Gly Tyr Lys Val Leu Val Leu Asn
    50                  55                  60
Pro Ser Val Ala Ala Thr Leu Gly Phe Gly Ala Tyr Met Ser Lys Ala
65                  70                  75                  80
His Gly Ile Asp Pro Asn Ile Arg Thr Gly Val Arg Thr Ile Thr Thr
                85                  90                  95
Gly Ser Pro Ile Thr Tyr Ser Thr Tyr Gly Lys Phe Leu Ala Asp Gly
            100                 105                 110
Gly Cys Ser Gly Gly Ala Tyr Asp Ile Ile Cys Asp Glu Ser His
            115                 120                 125
Ser Thr Asp Ala Thr Ser Ile Leu Gly Ile Gly Thr Val Leu Asp Gln
    130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
            180                 185                 190
Val Ile Lys Gly Gly Arg His Leu Ile Phe Cys His Ser Lys Lys Lys
        195                 200                 205
Cys Asp Glu Leu Ala Ala Lys Leu Val Ala Leu Gly Ile Asn Ala Val
    210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
            260                 265                 270
Phe Ser Leu Asp Pro Thr Phe Thr Ile Glu Thr Ile Thr Leu Pro Gln
        275                 280                 285
Asp Ala Val Ser Arg Thr Gln Arg Arg Gly Arg Thr Gly Arg Gly Lys
    290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
            340                 345                 350
Asn Thr Pro Gly Leu Pro Val Ser Gln Asp His Leu Glu Phe Trp Glu
        355                 360                 365
Gly Val Phe Thr Gly Leu Thr His Ile Asp Ala His Phe Leu Ser Gln
    370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Pro Ser Trp Asp Gln Met
                405                 410                 415
```

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 77
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

| gctgttgact | ttatcccggt | tgaaaatctc | gagactacta | tgcgttctcc | ggttttcact | 60 |
| gacaactctt | ctccgccggt | tgttccgcag | tctttccagg | ttgctcacct | gcatgctccg | 120 |
| actggttctg | gtaaatctac | taagttcca | gctgcttacg | ctgctcaggg | ttacaaagtt | 180 |
| ctggttctga | acccgtctgt | tgctgctact | ctgggtttcg | cgcctacat | gtctaaagct | 240 |
| cacggtatcg | acccgaacat | tcgtactggt | gtacgtacta | tcactactgg | ttctccgatc | 300 |
| acttactcta | cttacggtaa | attcctggct | gacggtggtt | gctctggtgg | tgcttacgat | 360 |
| atcatcatct | gcgacgaaag | ccactctact | gacgctactt | ctatcctggg | tatcggtacc | 420 |
| gttctggacc | aggctgaaac | tgcaggtgct | cgtctggttg | ttctggctac | tgctactccg | 480 |
| ccgggttctg | ttactgttcc | gcacccgaac | atcgaagaag | ttgctctgtc | gactactggt | 540 |
| gaaatcccgt | tctacggtaa | agctatcccg | ctcgaggtta | tcaaaggtgg | tcgtcacctg | 600 |
| attttctgcc | actctaaaaa | aaaatgcgac | gaactggctg | ctaagcttgt | tgctctgggt | 660 |
| atcaacgctg | ttgcttacta | ccgtggtctg | gacgtttctg | ttatcccgac | ttctggtgac | 720 |
| gttgttgttg | tggccactga | cgctctgatg | actggttaca | ctggtgactt | cgactctgtt | 780 |
| atcgattgca | acacttgcgt | tactcagacc | gtagatttta | gcctggaccc | gactttcact | 840 |
| atcgaaacga | tcaccctgcc | gcaggatgca | gtttcccgta | cccagcgtcg | tggccgtacc | 900 |
| ggtcgcggca | aaccgggtat | ttaccgtttc | gtggcgccgg | gcgagcgtcc | atccggtatg | 960 |
| ttcgatagct | ctgttctgtg | tgagtgttat | gacgcgggtt | gcgcgtggta | cgaactgact | 1020 |
| ccggctgaaa | ctactgtacg | cctgcgtgca | tacatgaata | cgccgggtct | gccggtgtgt | 1080 |
| caagaccacc | tggaatttttg | gaaggtgtc | tttactggcc | tgacccatat | cgacgcacac | 1140 |
| tttctgtccc | agactaaaca | gtctggtgaa | aacctgccgt | acctggtggc | gtatcaagcc | 1200 |
| actgtgtgcg | cccgtgcgca | ggcgccgcca | ccgagctggg | accaaatgtg | gaagtgcctg | 1260 |
| atccgtctga | aaccgaccct | gcacggtccg | acgccactgc | tgtaccgcct | gggtgcagtg | 1320 |
| cagaacgaaa | tcacgctgac | gcacccggtc | actaaataca | ttatgactag | catgagcgca | 1380 |
| gacctggaag | tggtgacttc | c |  |  |  | 1401 |

<210> SEQ ID NO 78
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Ala Val Asp Phe Ile Pro Val Glu Asn Leu Glu Thr Thr Met Arg Ser
 1               5                  10                  15
Pro Val Phe Thr Asp Asn Ser Ser Pro Val Pro Gln Ser Phe
             20                  25                  30
Gln Val Ala His Leu His Ala Pro Thr Gly Ser Gly Lys Ser Thr Lys
         35                  40                  45
Val Pro Ala Ala Tyr Ala Ala Gln Gly Tyr Lys Val Leu Val Leu Asn
     50                  55                  60
Pro Ser Val Ala Ala Thr Leu Gly Phe Gly Ala Tyr Met Ser Lys Ala
 65                  70                  75                  80
His Gly Ile Asp Pro Asn Ile Arg Thr Gly Val Arg Thr Ile Thr Thr
                 85                  90                  95
Gly Ser Pro Ile Thr Tyr Ser Thr Tyr Gly Lys Phe Leu Ala Asp Gly
            100                 105                 110
Gly Cys Ser Gly Gly Ala Tyr Asp Ile Ile Ile Cys Asp Glu Ser His
            115                 120                 125
Ser Thr Asp Ala Thr Ser Ile Leu Gly Ile Gly Thr Val Leu Asp Gln
130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
                180                 185                 190
Val Ile Lys Gly Gly Arg His Leu Ile Phe Cys His Ser Lys Lys Lys
                195                 200                 205
Cys Asp Glu Leu Ala Ala Lys Leu Val Ala Leu Gly Ile Asn Ala Val
210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
            275                 280                 285
Asp Ala Val Ser Arg Thr Gln Arg Arg Gly Arg Thr Gly Arg Gly Lys
        290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
            355                 360                 365
Gly Val Phe Thr Gly Leu Thr His Ile Asp Ala His Phe Leu Ser Gln
        370                 375                 380
Thr Lys Gln Ser Gly Glu Asn Leu Pro Tyr Leu Val Ala Tyr Gln Ala
385                 390                 395                 400
```

-continued

```
Thr Val Cys Ala Arg Ala Gln Ala Pro Pro Ser Trp Asp Gln Met
            405                 410                 415

Trp Lys Cys Leu Ile Arg Leu Lys Pro Thr Leu His Gly Pro Thr Pro
        420                 425                 430

Leu Leu Tyr Arg Leu Gly Ala Val Gln Asn Glu Ile Thr Leu Thr His
            435                 440                 445

Pro Val Thr Lys Tyr Ile Met Thr Ser Met Ser Ala Asp Leu Glu Val
    450                 455                 460

Val Thr Ser
465
```

<210> SEQ ID NO 79
<211> LENGTH: 1401
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 79

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accagtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
atttttctgcc actctaaaaa aaaaagcgac gaactggctg ctaagcttgt tgctctgggt     660
atcaacgctg ttgcttacta ccgtggtctg acgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 80
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Gln Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Ser Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
```

```
                385                 390                 395                 400
Thr Val Cys Ala Arg Ala Gln Ala Pro Pro Ser Trp Asp Gln Met
                        405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
        450                 455                 460

Val Thr Ser
465

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggcggctgca gcggtggcgc g                                                     21

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Cys Ser Gly Gly Ala
1               5

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gatgaatgtc atagcaccga t                                                     21

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Glu Cys His Ser Thr Asp
1               5

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 85
agcaaaaaga aatgcgatga a                                              21

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Lys Lys Lys Cys Asp Glu
1               5

<210> SEQ ID NO 87
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Val Asp Phe Ile Pro Val Glu Asn Leu Glu Thr Thr Met Arg Ser
1               5                  10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp

```
                260             265             270
Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
        450                 455                 460

Val Thr
465

<210> SEQ ID NO 88
<211> LENGTH: 3011
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140
```

-continued

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn

```
                  565                 570                 575
Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Thr Thr Thr Gln Trp
        660                 665                 670

Gln Val Leu Pro Cys Ser Phe Thr Thr Leu Pro Ala Leu Ser Thr Gly
    675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
            725                 730                 735

Met Met Leu Leu Ile Ser Gln Ala Glu Ala Leu Glu Asn Leu Val
        740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
        820                 825                 830

Pro Tyr Tyr Lys Arg Tyr Ile Ser Trp Cys Leu Trp Trp Leu Gln Tyr
    835                 840                 845

Phe Leu Thr Arg Val Glu Ala Gln Leu His Val Trp Ile Pro Pro Leu
850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
            885                 890                 895

Gly Pro Leu Trp Ile Leu Gln Ala Ser Leu Leu Lys Val Pro Tyr Phe
        900                 905                 910

Val Arg Val Gln Gly Leu Leu Arg Phe Cys Ala Leu Ala Arg Lys Met
    915                 920                 925

Ile Gly Gly His Tyr Val Gln Met Val Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
            965                 970                 975

Ser Gln Met Glu Thr Lys Leu Ile Thr Trp Gly Ala Asp Thr Ala Ala
        980                 985                 990
```

```
Cys Gly Asp Ile Ile Asn Gly Leu  Pro Val Ser Ala Arg  Arg Gly Arg
        995                 1000                 1005

Glu Ile Leu Leu Gly Pro Ala  Asp Gly Met Val Ser  Lys Gly Trp
    1010                1015                1020

Arg Leu Leu Ala Pro Ile Thr  Ala Tyr Ala Gln Gln  Thr Arg Gly
    1025                1030                1035

Leu Leu Gly Cys Ile Ile Thr  Ser Leu Thr Gly Arg  Asp Lys Asn
    1040                1045                1050

Gln Val Glu Gly Glu Val Gln  Ile Val Ser Thr Ala  Ala Gln Thr
    1055                1060                1065

Phe Leu Ala Thr Cys Ile Asn  Gly Val Cys Trp Thr  Val Tyr His
    1070                1075                1080

Gly Ala Gly Thr Arg Thr Ile  Ala Ser Pro Lys Gly  Pro Val Ile
    1085                1090                1095

Gln Met Tyr Thr Asn Val Asp  Gln Asp Leu Val Gly  Trp Pro Ala
    1100                1105                1110

Pro Gln Gly Ser Arg Ser Leu  Thr Pro Cys Thr Cys  Gly Ser Ser
    1115                1120                1125

Asp Leu Tyr Leu Val Thr Arg  His Ala Asp Val Ile  Pro Val Arg
    1130                1135                1140

Arg Arg Gly Asp Ser Arg Gly  Ser Leu Leu Ser Pro  Arg Pro Ile
    1145                1150                1155

Ser Tyr Leu Lys Gly Ser Ser  Gly Gly Pro Leu Leu  Cys Pro Ala
    1160                1165                1170

Gly His Ala Val Gly Ile Phe  Arg Ala Ala Val Cys  Thr Arg Gly
    1175                1180                1185

Val Ala Lys Ala Val Asp Phe  Ile Pro Val Glu Asn  Leu Glu Thr
    1190                1195                1200

Thr Met Arg Ser Pro Val Phe  Thr Asp Asn Ser Ser  Pro Pro Val
    1205                1210                1215

Val Pro Gln Ser Phe Gln Val  Ala His Leu His Ala  Pro Thr Gly
    1220                1225                1230

Ser Gly Lys Ser Thr Lys Val  Pro Ala Ala Tyr Ala  Ala Gln Gly
    1235                1240                1245

Tyr Lys Val Leu Val Leu Asn  Pro Ser Val Ala Ala  Thr Leu Gly
    1250                1255                1260

Phe Gly Ala Tyr Met Ser Lys  Ala His Gly Ile Asp  Pro Asn Ile
    1265                1270                1275

Arg Thr Gly Val Arg Thr Ile  Thr Thr Gly Ser Pro  Ile Thr Tyr
    1280                1285                1290

Ser Thr Tyr Gly Lys Phe Leu  Ala Asp Gly Gly Cys  Ser Gly Gly
    1295                1300                1305

Ala Tyr Asp Ile Ile Ile Cys  Asp Glu Cys His Ser  Thr Asp Ala
    1310                1315                1320

Thr Ser Ile Leu Gly Ile Gly  Thr Val Leu Asp Gln  Ala Glu Thr
    1325                1330                1335

Ala Gly Ala Arg Leu Val Val  Leu Ala Thr Ala Thr  Pro Pro Gly
    1340                1345                1350

Ser Val Thr Val Pro His Pro  Asn Ile Glu Glu Val  Ala Leu Ser
    1355                1360                1365

Thr Thr Gly Glu Ile Pro Phe  Tyr Gly Lys Ala Ile  Pro Leu Glu
    1370                1375                1380
```

```
Val Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Ala Thr Asp Ala Leu Met Thr Gly
    1430                1435                1440

Tyr Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Ile Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Met Asn Thr Pro Gly Leu
    1535                1540                1545

Pro Val Cys Gln Asp His Leu Glu Phe Trp Glu Gly Val Phe Thr
    1550                1555                1560

Gly Leu Thr His Ile Asp Ala His Phe Leu Ser Gln Thr Lys Gln
    1565                1570                1575

Ser Gly Glu Asn Leu Pro Tyr Leu Val Ala Tyr Gln Ala Thr Val
    1580                1585                1590

Cys Ala Arg Ala Gln Ala Pro Pro Pro Ser Trp Asp Gln Met Trp
    1595                1600                1605

Lys Cys Leu Ile Arg Leu Lys Pro Thr Leu His Gly Pro Thr Pro
    1610                1615                1620

Leu Leu Tyr Arg Leu Gly Ala Val Gln Asn Glu Ile Thr Leu Thr
    1625                1630                1635

His Pro Val Thr Lys Tyr Ile Met Thr Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Ser Thr Gly Cys Val Val Ile Val
    1670                1675                1680

Gly Arg Val Val Leu Ser Gly Lys Pro Ala Ile Ile Pro Asp Arg
    1685                1690                1695

Glu Val Leu Tyr Arg Glu Phe Asp Glu Met Glu Glu Cys Ser Gln
    1700                1705                1710

His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala
    1730                1735                1740

Glu Val Ile Ala Pro Ala Val Gln Thr Asn Trp Gln Lys Leu Glu
    1745                1750                1755

Thr Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
```

-continued

```
              1775                1780                1785
Ser  Leu  Met  Ala  Phe  Thr  Ala  Ala  Val  Thr  Ser  Pro  Leu  Thr  Thr
     1790                1795                1800

Ser  Gln  Thr  Leu  Leu  Phe  Asn  Ile  Leu  Gly  Gly  Trp  Val  Ala  Ala
     1805                1810                1815

Gln  Leu  Ala  Ala  Pro  Gly  Ala  Ala  Thr  Ala  Phe  Val  Gly  Ala  Gly
     1820                1825                1830

Leu  Ala  Gly  Ala  Ala  Ile  Gly  Ser  Val  Gly  Leu  Gly  Lys  Val  Leu
     1835                1840                1845

Ile  Asp  Ile  Leu  Ala  Gly  Tyr  Gly  Ala  Gly  Val  Ala  Gly  Ala  Leu
     1850                1855                1860

Val  Ala  Phe  Lys  Ile  Met  Ser  Gly  Glu  Val  Pro  Ser  Thr  Glu  Asp
     1865                1870                1875

Leu  Val  Asn  Leu  Leu  Pro  Ala  Ile  Leu  Ser  Pro  Gly  Ala  Leu  Val
     1880                1885                1890

Val  Gly  Val  Val  Cys  Ala  Ala  Ile  Leu  Arg  Arg  His  Val  Gly  Pro
     1895                1900                1905

Gly  Glu  Gly  Ala  Val  Gln  Trp  Met  Asn  Arg  Leu  Ile  Ala  Phe  Ala
     1910                1915                1920

Ser  Arg  Gly  Asn  His  Val  Ser  Pro  Thr  His  Tyr  Val  Pro  Glu  Ser
     1925                1930                1935

Asp  Ala  Ala  Arg  Val  Thr  Ala  Ile  Leu  Ser  Ser  Leu  Thr  Val
     1940                1945                1950

Thr  Gln  Leu  Leu  Arg  Arg  Leu  His  Gln  Trp  Ile  Ser  Ser  Glu  Cys
     1955                1960                1965

Thr  Thr  Pro  Cys  Ser  Gly  Ser  Trp  Leu  Arg  Asp  Ile  Trp  Asp  Trp
     1970                1975                1980

Ile  Cys  Glu  Val  Leu  Ser  Asp  Phe  Lys  Thr  Trp  Leu  Lys  Ala  Lys
     1985                1990                1995

Leu  Met  Pro  Gln  Leu  Pro  Gly  Ile  Pro  Phe  Val  Ser  Cys  Gln  Arg
     2000                2005                2010

Gly  Tyr  Lys  Gly  Val  Trp  Arg  Val  Asp  Gly  Ile  Met  His  Thr  Arg
     2015                2020                2025

Cys  His  Cys  Gly  Ala  Glu  Ile  Thr  Gly  His  Val  Lys  Asn  Gly  Thr
     2030                2035                2040

Met  Arg  Ile  Val  Gly  Pro  Arg  Thr  Cys  Arg  Asn  Met  Trp  Ser  Gly
     2045                2050                2055

Thr  Phe  Pro  Ile  Asn  Ala  Tyr  Thr  Thr  Gly  Pro  Cys  Thr  Pro  Leu
     2060                2065                2070

Pro  Ala  Pro  Asn  Tyr  Thr  Phe  Ala  Leu  Trp  Arg  Val  Ser  Ala  Glu
     2075                2080                2085

Glu  Tyr  Val  Glu  Ile  Arg  Gln  Val  Gly  Asp  Phe  His  Tyr  Val  Thr
     2090                2095                2100

Gly  Met  Thr  Thr  Asp  Asn  Leu  Lys  Cys  Pro  Cys  Gln  Val  Pro  Ser
     2105                2110                2115

Pro  Glu  Phe  Phe  Thr  Glu  Leu  Asp  Gly  Val  Arg  Leu  His  Arg  Phe
     2120                2125                2130

Ala  Pro  Pro  Cys  Lys  Pro  Leu  Leu  Arg  Glu  Glu  Val  Ser  Phe  Arg
     2135                2140                2145

Val  Gly  Leu  His  Glu  Tyr  Pro  Val  Gly  Ser  Gln  Leu  Pro  Cys  Glu
     2150                2155                2160

Pro  Glu  Pro  Asp  Val  Ala  Val  Leu  Thr  Ser  Met  Leu  Thr  Asp  Pro
     2165                2170                2175
```

```
Ser His Ile Thr Ala Glu Ala Ala Gly Arg Arg Leu Ala Arg Gly
    2180            2185                2190

Ser Pro Pro Ser Val Ala Ser Ser Ser Ala Ser Gln Leu Ser Ala
    2195            2200                2205

Pro Ser Leu Lys Ala Thr Cys Thr Ala Asn His Asp Ser Pro Asp
    2210            2215                2220

Ala Glu Leu Ile Glu Ala Asn Leu Leu Trp Arg Gln Glu Met Gly
    2225            2230                2235

Gly Asn Ile Thr Arg Val Glu Ser Glu Asn Lys Val Val Ile Leu
    2240            2245                2250

Asp Ser Phe Asp Pro Leu Val Ala Glu Glu Asp Glu Arg Glu Ile
    2255            2260                2265

Ser Val Pro Ala Glu Ile Leu Arg Lys Ser Arg Arg Phe Ala Gln
    2270            2275                2280

Ala Leu Pro Val Trp Ala Arg Pro Asp Tyr Asn Pro Pro Leu Val
    2285            2290                2295

Glu Thr Trp Lys Lys Pro Asp Tyr Glu Pro Pro Val Val His Gly
    2300            2305                2310

Cys Pro Leu Pro Pro Pro Lys Ser Pro Pro Val Pro Pro Pro Arg
    2315            2320                2325

Lys Lys Arg Thr Val Val Leu Thr Glu Ser Thr Leu Ser Thr Ala
    2330            2335                2340

Leu Ala Glu Leu Ala Thr Arg Ser Phe Gly Ser Ser Ser Thr Ser
    2345            2350                2355

Gly Ile Thr Gly Asp Asn Thr Thr Thr Ser Ser Glu Pro Ala Pro
    2360            2365                2370

Ser Gly Cys Pro Pro Asp Ser Asp Ala Glu Ser Tyr Ser Ser Met
    2375            2380                2385

Pro Pro Leu Glu Gly Glu Pro Gly Asp Pro Asp Leu Ser Asp Gly
    2390            2395                2400

Ser Trp Ser Thr Val Ser Ser Glu Ala Asn Ala Glu Asp Val Val
    2405            2410                2415

Cys Cys Ser Met Ser Tyr Ser Trp Thr Gly Ala Leu Val Thr Pro
    2420            2425                2430

Cys Ala Ala Glu Glu Gln Lys Leu Pro Ile Asn Ala Leu Ser Asn
    2435            2440                2445

Ser Leu Leu Arg His His Asn Leu Val Tyr Ser Thr Thr Ser Arg
    2450            2455                2460

Ser Ala Cys Gln Arg Gln Lys Lys Val Thr Phe Asp Arg Leu Gln
    2465            2470                2475

Val Leu Asp Ser His Tyr Gln Asp Val Leu Lys Glu Val Lys Ala
    2480            2485                2490

Ala Ala Ser Lys Val Lys Ala Asn Leu Leu Ser Val Glu Glu Ala
    2495            2500                2505

Cys Ser Leu Thr Pro Pro His Ser Ala Lys Ser Lys Phe Gly Tyr
    2510            2515                2520

Gly Ala Lys Asp Val Arg Cys His Ala Arg Lys Ala Val Thr His
    2525            2530                2535

Ile Asn Ser Val Trp Lys Asp Leu Leu Glu Asp Asn Val Thr Pro
    2540            2545                2550

Ile Asp Thr Thr Ile Met Ala Lys Asn Glu Val Phe Cys Val Gln
    2555            2560                2565
```

```
Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Thr Lys Leu Pro Leu Ala Val Met Gly Ser Ser Tyr Gly Phe
    2600                2605                2610

Gln Tyr Ser Pro Gly Gln Arg Val Glu Phe Leu Val Gln Ala Trp
    2615                2620                2625

Lys Ser Lys Lys Thr Pro Met Gly Phe Ser Tyr Asp Thr Arg Cys
    2630                2635                2640

Phe Asp Ser Thr Val Thr Glu Ser Asp Ile Arg Thr Glu Glu Ala
    2645                2650                2655

Ile Tyr Gln Cys Cys Asp Leu Asp Pro Gln Ala Arg Val Ala Ile
    2660                2665                2670

Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
    2735                2740                2745

Val Gln Glu Asp Ala Ala Ser Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asp Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ala Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955

Ile Ala Ala Ala Gly Gln Leu Asp Leu Ser Gly Trp Phe Thr Ala
```

```
                    2960                2965                2970

Gly Tyr Ser Gly Gly Asp Ile Tyr His Ser Val Ser His Ala Arg
        2975                2980                2985

Pro Arg Trp Ile Trp Phe Cys Leu Leu Leu Leu Ala Ala Gly Val
        2990                2995                3000

Gly Ile Tyr Leu Leu Pro Asn Arg
        3005                3010

<210> SEQ ID NO 89
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Ser Gly Ser Gly His His His His His His His Gly Gly Cys
1               5                   10                  15

Ser Gly Gly Ala Arg Ser Gly Cys
            20

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Ser Gly Ser Gly His His His His His His His Asp Glu Cys
1               5                   10                  15

His Ser Thr Asp Arg Ser Gly Cys
            20

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ser Gly Cys Gly His His His His His His His Gly Gly Cys
1               5                   10                  15

Ser Gly Gly Ala
            20

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Ser Gly His His His His His His His Gly Gly Cys
1               5                   10                  15

Ser Gly Gly Ala
            20
```

<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Gly Ser Gly His His His His His His His Asp Glu Cys
1               5                   10                  15

His Ser Thr Asp
            20

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Gly Ser Gly His His His His His His His Ser Lys Lys
1               5                   10                  15

Lys Cys Asp Glu
            20

<210> SEQ ID NO 95
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Gly Ser Gly His His His His His His His Ser Lys Lys
1               5                   10                  15

Lys Cys Asp Glu Arg Ser Gly Cys
            20

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met Ser Gly Leu Asn Asp Ile Phe Glu Ala Gln Lys Ile Glu Trp His
1               5                   10                  15

Glu

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ser Gly Ser Asn Ser Met

```
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Gly Ser Gly
1               5

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Leu Asn Asp Ile Phe Glu Ala Gln Lys Ile Glu Trp His Glu
1               5                   10                  15

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ser Gly Ser Gly His His His His His His
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ser Gly Ser Gly His His His His His His Gly Gly
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gly Ser Gly Ser Gly His His His His His His
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 103

Ser Gly Ser Gly Ser Gly His His His His His His Gly Gly
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Gly Ser Gly Ser Gly His His His His His His His His
1               5                   10

<210> SEQ ID NO 105
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Asn Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

-continued

Phe Asp Ser Val Ile Asp Cys Asn Thr Cys Val Gln Thr Val Asp
              260                 265                 270

Phe Ser Leu Asp Pro Thr Phe Thr Ile Glu Thr Ile Thr Leu Pro Gln
              275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
              340                 345                 350

Asn Thr Pro Gly Leu Pro Val Cys Gln Asp His Leu Glu Phe Trp Glu
              355                 360                 365

Gly Val Phe Thr Gly Leu Thr His Ile Asp Ala His Phe Leu Ser Gln
              370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
              420                 425                 430

Leu Leu Tyr Arg Leu Gly Ala Val Gln Asn Glu Ile Thr Leu Thr His
              435                 440                 445

Pro Val Thr Lys Tyr Ile Met Thr Cys Met Ser Ala Asp Leu Glu Val
              450                 455                 460

Val Thr
465

<210> SEQ ID NO 106
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
                20                  25                  30

Gln Val Ala His Leu His Ala Pro Thr Gly Ser Gly Lys Ala Thr Lys
              35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
              100                 105                 110

Gly Cys Ser Gly Gly Ala Tyr Asp Ile Ile Cys Asp Glu Cys His
              115                 120                 125

Ser Thr Asp Ala Thr Ser Ile Leu Gly Ile Gly Thr Val Leu Asp Gln

```
            130                 135                 140
Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 107
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Val Asp Phe Ile Pro Val Glu Asn Leu Glu Thr Thr Met Arg Ser
1               5                   10                  15
```

```
Pro Val Phe Thr Asp Asn Ser Ser Pro Val Pro Gln Ser Phe
            20                  25                  30

Gln Val Ala His Leu His Ala Pro Thr Gly Ser Gly Lys Ser Glu Lys
        35                  40                  45

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
```

```
                    435                 440                 445
Pro Val Thr Lys Tyr Ile Met Thr Cys Met Ser Ala Asp Leu Glu Val
            450                 455                 460

Val Thr
465

<210> SEQ ID NO 108
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
                35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Ser Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320
```

```
Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
            405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr
465

<210> SEQ ID NO 109
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asn Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205
```

Cys Asp Glu Leu Ala Ala Lys Leu Val Ala Leu Gly Ile Asn Ala Val
                210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 110
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr

```
                        85                  90                  95
Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Gln Gln Cys
            115                 120                 125

His Ser Thr Asp Ala Thr Ser Ile Leu Gly Ile Gly Thr Val Leu Asp
            130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
            195                 200                 205

Lys Cys Asp Glu Leu Ala Ala Lys Leu Val Ala Leu Gly Ile Asn Ala
            210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255

Asp Phe Asp Ser Val Ile Asp Cys Asn Thr Cys Val Thr Gln Thr Val
            260                 265                 270

Asp Phe Ser Leu Asp Pro Thr Phe Thr Ile Glu Thr Ile Thr Leu Pro
            275                 280                 285

Gln Asp Ala Val Ser Arg Thr Gln Arg Arg Gly Arg Thr Gly Arg Gly
290                 295                 300

Lys Pro Gly Ile Tyr Arg Phe Val Ala Pro Gly Glu Arg Pro Ser Gly
305                 310                 315                 320

Met Phe Asp Ser Ser Val Leu Cys Glu Cys Tyr Asp Ala Gly Cys Ala
            325                 330                 335

Trp Tyr Glu Leu Thr Pro Ala Glu Thr Thr Val Arg Leu Arg Ala Tyr
            340                 345                 350

Met Asn Thr Pro Gly Leu Pro Val Cys Gln Asp His Leu Glu Phe Trp
            355                 360                 365

Glu Gly Val Phe Thr Gly Leu Thr His Ile Asp Ala His Phe Leu Ser
            370                 375                 380

Gln Thr Lys Gln Ser Gly Glu Asn Leu Pro Tyr Leu Val Ala Tyr Gln
385                 390                 395                 400

Ala Thr Val Cys Ala Arg Ala Gln Ala Pro Pro Pro Ser Trp Asp Gln
            405                 410                 415

Met Trp Lys Cys Leu Ile Arg Leu Lys Pro Thr Leu His Gly Pro Thr
            420                 425                 430

Pro Leu Leu Tyr Arg Leu Gly Ala Val Gln Asn Glu Ile Thr Leu Thr
            435                 440                 445

His Pro Val Thr Lys Tyr Ile Met Thr Cys Met Ser Ala Asp Leu Glu
            450                 455                 460

Val Val Thr
465

<210> SEQ ID NO 111
<211> LENGTH: 466
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 111

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys Ala
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
```

```
385                 390                 395                 400
Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
        450                 455                 460

Val Thr
465

<210> SEQ ID NO 112
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Gly Gly Asp
                245                 250                 255

Phe Asp Ser Val Ile Asp Cys Asn Thr Cys Val Thr Gln Thr Val Asp
            260                 265                 270
```

```
Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
                385                 390                 395                 400

Thr Val Cys Ala Arg Ala Gln Ala Pro Pro Ser Trp Asp Gln Met
                    405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
        450                 455                 460

Val Thr
465

<210> SEQ ID NO 113
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160
```

```
Pro Gly Ser Val Thr Val Pro His Pro Asn Ile Glu Val Ala Leu
            165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys
            195                 200                 205

Cys Asp Glu Leu Ala Ala Lys Leu Val Ala Leu Gly Ile Asn Ala Val
            210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
            245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
            275                 280                 285

Asp Ala Val Ser Arg Thr His Arg Arg Gly Arg Thr Gly Arg Gly Lys
            290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
            325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
            405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr
465

<210> SEQ ID NO 114
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
            20                  25                  30

Gln Val Ala His Leu His Ala Pro Thr Gly Ser Gly Lys Ser Thr Lys
```

-continued

```
            35                  40                  45
Val Pro Ala Ala Tyr Ala Ala Gln Gly Tyr Lys Val Leu Val Leu Asn
 50                  55                  60
Pro Ser Val Ala Ala Thr Leu Gly Phe Gly Ala Tyr Met Ser Lys Ala
 65                  70                  75                  80
His Gly Ile Asp Pro Asn Ile Arg Thr Gly Val Arg Thr Ile Thr Thr
                     85                  90                  95
Gly Ser Pro Ile Thr Tyr Ser Thr Tyr Gly Lys Phe Leu Ala Asp Gly
                    100                 105                 110
Gly Cys Ser Gly Gly Ala Tyr Asp Ile Ile Cys Asp Glu Cys His
                115                 120                 125
Ser Thr Asp Ala Thr Ser Ile Leu Gly Ile Gly Thr Val Leu Asp Gln
130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                    165                 170                 175
Ser Thr Thr Gly Glu Ile Pro Phe Tyr Gly Lys Ala Ile Pro Leu Glu
                180                 185                 190
Val Ile Lys Gly Gly Arg His Leu Ile Phe Cys His Ser Lys Lys Lys
            195                 200                 205
Cys Asp Glu Leu Ala Ala Lys Leu Val Ala Leu Gly Ile Asn Ala Val
210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                    245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
            275                 280                 285
Asp Ala Val Ser Arg Thr Gln Arg Arg Gly Ala Thr Gly Arg Gly Lys
290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                    325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
            355                 360                 365
Gly Val Phe Thr Gly Leu Thr His Ile Asp Ala His Phe Leu Ser Gln
370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Ser Trp Asp Gln Met
                    405                 410                 415
Trp Lys Cys Leu Ile Arg Leu Lys Pro Thr Leu His Gly Pro Thr Pro
                420                 425                 430
Leu Leu Tyr Arg Leu Gly Ala Val Gln Asn Glu Ile Thr Leu Thr His
            435                 440                 445
Pro Val Thr Lys Tyr Ile Met Thr Cys Met Ser Ala Asp Leu Glu Val
450                 455                 460
```

```
Val Thr
465

<210> SEQ ID NO 115
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Lys Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
```

```
                    340                 345                 350
Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
        450                 455                 460

Val Thr
465

<210> SEQ ID NO 116
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220
```

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
            245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Ala
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
450                 455                 460

Val Thr
465

<210> SEQ ID NO 117
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Ser Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr
465

<210> SEQ ID NO 118
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
                35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Ser Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415
```

```
Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
450                 455                 460

Val Thr
465

<210> SEQ ID NO 119
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30      Phe

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Ser His
            115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
```

```
                    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                    325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                    405                 410                 415

Trp Lys Cys Leu Ile Arg Leu Lys Pro Thr Leu His Gly Pro Thr Pro
                    420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
            450                 455                 460

Val Thr
465

<210> SEQ ID NO 120
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
                20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175
```

```
Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 121
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60
```

```
Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
             85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Ser Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
                275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
            450                 455                 460

Val Thr
465
```

```
<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 122

His His His His His His
1               5
```